US010660965B2

(12) United States Patent
Desai et al.

(10) Patent No.: US 10,660,965 B2
(45) Date of Patent: May 26, 2020

(54) METHODS OF ENHANCING DRUG DELIVERY AND EFFECTIVENESS OF THERAPEUTIC AGENTS

(75) Inventors: Neil P. Desai, Pacific Palisades, CA (US); Patrick Soon-Shiong, Culver City, CA (US)

(73) Assignee: Abraxis BioScience, LLC, Summit, NJ (US)

( * ) Notice: Subject to any disclaimer, the term of this patent is extended or adjusted under 35 U.S.C. 154(b) by 41 days.

(21) Appl. No.: 13/073,861

(22) Filed: Mar. 28, 2011

(65) Prior Publication Data

US 2012/0076862 A1   Mar. 29, 2012

Related U.S. Application Data

(60) Provisional application No. 61/318,777, filed on Mar. 29, 2010.

(51) Int. Cl.
| A61K 47/42 | (2017.01) |
| A61K 31/337 | (2006.01) |
| A61K 31/573 | (2006.01) |
| A61K 31/7068 | (2006.01) |
| A61K 45/06 | (2006.01) |
| A61K 9/14 | (2006.01) |

(52) U.S. Cl.
CPC ............ *A61K 47/42* (2013.01); *A61K 31/337* (2013.01); *A61K 31/573* (2013.01); *A61K 31/7068* (2013.01); *A61K 45/06* (2013.01)

(58) Field of Classification Search
CPC .............. A61K 9/5169; A61K 31/337; A61K 31/7064; A61K 31/7068; A61K 31/7088
See application file for complete search history.

(56) References Cited

U.S. PATENT DOCUMENTS

| 5,362,478 A | 11/1994 | Desai et al. |
| 5,439,686 A | 8/1995 | Desai et al. |
| 5,470,571 A | 11/1995 | Herlyn et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,510,118 A | 4/1996 | Bosch et al. |
| 5,512,268 A | 4/1996 | Grinstaff et al. |
| 5,534,270 A | 7/1996 | De Castro |
| 5,558,864 A | 9/1996 | Bendig et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,651,986 A | 7/1997 | Brem et al. |
| 5,662,883 A | 9/1997 | Bagchi et al. |
| 5,665,382 A | 9/1997 | Grinstaff et al. |
| 5,665,383 A | 9/1997 | Grinstaff et al. |
| 5,690,928 A | 11/1997 | Heimbrook et al. |
| 5,733,925 A | 3/1998 | Kunz et al. |
| 5,744,460 A | 4/1998 | Müller et al. |
| 5,859,018 A | 1/1999 | Brown et al. |
| 5,873,904 A | 2/1999 | Ragheb et al. |
| 5,886,026 A | 3/1999 | Hunter et al. |
| 5,916,596 A | 6/1999 | Desai et al. |
| 5,977,163 A | 11/1999 | Li et al. |
| 5,981,568 A | 11/1999 | Kunz et al. |
| 5,994,341 A | 11/1999 | Hunter et al. |
| 5,997,904 A | 12/1999 | Magdassi et al. |
| 6,096,070 A | 8/2000 | Ragheb et al. |
| 6,096,331 A | 8/2000 | Desai et al. |
| 6,143,276 A | 11/2000 | Unger |
| 6,239,124 B1 | 5/2001 | Zenke et al. |
| 6,268,390 B1 | 7/2001 | Kunz |
| 6,306,421 B1 | 10/2001 | Kunz et al. |

(Continued)

FOREIGN PATENT DOCUMENTS

| CA | 2765222 A1 | 8/2006 |
| EP | 0 584 001 A1 | 2/1994 |

(Continued)

OTHER PUBLICATIONS

US 8,968,752 B2, 03/2015, Desai et al. (withdrawn)
Stinchcombe. Nanoparticle albumin-bound paclitaxel: a Novel cremophor-EL-®-free formulation of paclitaxel. Nanomedicine, 2007, vol. 2 (4):415-423 (abstract, 2 pages).*
Bernstein. Docetaxel as an alternative to paclitaxel after acute hypersensitivity reactions. Ann Pharmacother. Nov. 2000, 34(11), pp. 1332-1335 (abstract only).*
Smith. et al. SPARC and CA19-9 as biomarkers in patients with advanced pancreatic cancer treated with nab paclitaxel plus gemcitabine. J. Clinical Oncology, 2008 ASCO Annual Meeting Proceedings, vol. 26, No. 15S (May 20 Supplement), 2008: 15592. (2 pages only).*

(Continued)

*Primary Examiner* — Lakshmi S Channavajjala
(74) *Attorney, Agent, or Firm* — Morrison & Foerster LLP

(57) ABSTRACT

The present invention in one aspect provides methods of enhancing uptake of a therapeutic agent in a target tissue as well as methods of treating a disease (such as cancer) or enhancing effectiveness of treatment with a therapeutic agent in an individual by co-administering a composition comprising nanoparticles comprising albumin and a poorly water soluble drug such as a taxane with the therapeutic agent. The present invention in another aspect provides a method of treatment or a method of selecting patients for treatment of a disease (such as cancer) with the combination of a therapeutic agent and a composition comprising nanoparticles comprising albumin and a poorly water soluble drug such as a taxane based on one or more characteristics of the target tissue that correlates or indicates the capability of getting enhanced therapeutic agent uptake as a result of the co-administration of the taxane nanoparticle composition in the target tissue (referred to as "the drug uptake capability"). Also provided are pharmaceutical compositions, article of manufacture, and kits useful for methods described herein.

12 Claims, No Drawings

(56) References Cited

U.S. PATENT DOCUMENTS

| | | |
|---|---|---|
| 6,506,405 B1 | 1/2003 | Desai et al. |
| 6,515,009 B1 | 2/2003 | Kunz et al. |
| 6,528,067 B1 | 3/2003 | Magdassi et al. |
| 6,537,579 B1 | 3/2003 | Desai et al. |
| 6,544,544 B2 | 4/2003 | Hunter et al. |
| 6,548,531 B2 | 4/2003 | Breimer et al. |
| 6,565,842 B1 | 5/2003 | Desai et al. |
| 6,566,405 B2 | 5/2003 | Weidner et al. |
| 6,569,441 B2 | 5/2003 | Kunz et al. |
| 6,652,884 B2 | 11/2003 | Falciani |
| 6,682,758 B1 | 1/2004 | Tabibi et al. |
| 6,689,803 B2 | 2/2004 | Hunter |
| 6,727,256 B1 | 4/2004 | Carter et al. |
| 6,730,699 B2 | 5/2004 | Li et al. |
| 6,749,868 B1 | 6/2004 | Desai et al. |
| 6,752,803 B2 | 6/2004 | Goldman et al. |
| 6,753,006 B1 | 6/2004 | Desai et al. |
| 6,872,715 B2 | 3/2005 | Santi et al. |
| 6,884,817 B2 | 4/2005 | Li et al. |
| 6,884,879 B1 | 4/2005 | Baca et al. |
| 6,929,818 B2 | 8/2005 | Luthra et al. |
| 7,038,071 B2 | 5/2006 | Lal |
| 7,101,568 B2 | 9/2006 | Dang et al. |
| 7,129,368 B2 | 10/2006 | Lal et al. |
| 7,141,576 B2 | 11/2006 | Lackey et al. |
| 7,232,919 B2 | 6/2007 | Lal |
| 7,332,568 B2 | 2/2008 | Trieu et al. |
| 7,405,208 B2 | 7/2008 | Santi et al. |
| 7,758,891 B2* | 7/2010 | Desai et al. ............ 424/489 |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,007,995 B2 | 8/2011 | Finn et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2* | 3/2012 | Desai et al. ............ 514/776 |
| 8,257,733 B2 | 9/2012 | Desai et al. |
| 8,268,348 B2 | 9/2012 | Desai et al. |
| 8,314,156 B2* | 11/2012 | Desai et al. ............ 514/776 |
| 8,415,304 B2 | 4/2013 | Trieu et al. |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |
| 8,927,019 B2 | 1/2015 | Desai et al. |
| 8,999,396 B2 | 4/2015 | Desai et al. |
| 9,012,518 B2 | 4/2015 | Desai et al. |
| 9,012,519 B2 | 4/2015 | Desai et al. |
| 9,061,014 B2 | 6/2015 | Seward et al. |
| 9,101,543 B2 | 8/2015 | Desai et al. |
| 9,149,455 B2 | 10/2015 | Desai et al. |
| 9,308,180 B2 | 4/2016 | De et al. |
| 9,370,494 B2 | 6/2016 | Yeo et al. |
| 9,393,318 B2 | 7/2016 | Desai et al. |
| 9,399,071 B2 | 7/2016 | Desai et al. |
| 9,399,072 B2 | 7/2016 | Desai et al. |
| 9,446,003 B2 | 9/2016 | Desai et al. |
| 9,511,046 B2 | 12/2016 | Desai et al. |
| 9,561,288 B2 | 2/2017 | Desai et al. |
| 9,585,960 B2 | 3/2017 | Foss et al. |
| 9,597,409 B2 | 3/2017 | Desai et al. |
| 9,675,578 B2 | 6/2017 | Desai et al. |
| 9,724,323 B2 | 8/2017 | Desai et al. |
| 9,820,949 B2 | 11/2017 | Desai et al. |
| 9,855,220 B2 | 1/2018 | Desai et al. |
| 9,884,013 B2 | 2/2018 | Seward et al. |
| 9,962,373 B2 | 5/2018 | Desai |
| 10,076,501 B2 | 9/2018 | Foss et al. |
| 10,258,565 B2 | 4/2019 | Seward |
| 10,328,031 B2 | 6/2019 | Desai |
| 10,413,531 B2 | 9/2019 | Desai |
| 2002/0031505 A1 | 3/2002 | Bissery |
| 2002/0169140 A1 | 11/2002 | Prendergast |
| 2003/0133955 A1 | 7/2003 | Desai et al. |
| 2003/0185894 A1 | 10/2003 | Zenoni et al. |
| 2003/0187062 A1 | 10/2003 | Zenoni et al. |
| 2003/0199425 A1 | 10/2003 | Desai et al. |
| 2003/0216369 A1 | 11/2003 | Rosen et al. |
| 2003/0220354 A1 | 11/2003 | McClure et al. |
| 2004/0033271 A1 | 2/2004 | Lederman |
| 2004/0047835 A1 | 3/2004 | Bianco |
| 2004/0053946 A1 | 3/2004 | Lackey et al. |
| 2004/0126400 A1 | 7/2004 | Iversen et al. |
| 2004/0143004 A1 | 7/2004 | Fargnoli et al. |
| 2004/0167079 A1 | 8/2004 | Tidmarsh |
| 2004/0248781 A1 | 12/2004 | Kerbel |
| 2005/0000900 A1 | 1/2005 | Huang et al. |
| 2005/0002983 A1 | 1/2005 | Johnson, Jr. |
| 2005/0004002 A1 | 1/2005 | Desai et al. |
| 2005/0026893 A1 | 2/2005 | Johnson, Jr. |
| 2005/0032699 A1 | 2/2005 | Holash et al. |
| 2005/0058684 A1 | 3/2005 | Shanley et al. |
| 2005/0095267 A1 | 5/2005 | Campbell et al. |
| 2005/0186208 A1 | 8/2005 | Fyfe et al. |
| 2005/0203174 A1 | 9/2005 | Santi et al. |
| 2006/0003931 A1 | 1/2006 | Eigenbrot, Jr. et al. |
| 2006/0013819 A1 | 1/2006 | Kelsey |
| 2006/0062821 A1 | 3/2006 | Simhambhatla et al. |
| 2006/0135486 A1 | 6/2006 | Owa et al. |
| 2006/0165744 A1 | 7/2006 | Jamil et al. |
| 2006/0188566 A1 | 8/2006 | Liversidge et al. |
| 2006/0199248 A1 | 9/2006 | Trieu et al. |
| 2007/0093547 A1 | 4/2007 | Desai et al. |
| 2007/0116774 A1 | 5/2007 | Desai et al. |
| 2007/0117133 A1 | 5/2007 | Trieu et al. |
| 2007/0129448 A1 | 6/2007 | Desai et al. |
| 2007/0166388 A1 | 7/2007 | Desai et al. |
| 2007/0196361 A1 | 8/2007 | Soon-Shiong et al. |
| 2007/0207196 A1 | 9/2007 | Zhang |
| 2008/0045559 A1 | 2/2008 | Zhang et al. |
| 2008/0063699 A1 | 3/2008 | Teifel et al. |
| 2008/0085902 A1 | 4/2008 | Bold et al. |
| 2008/0146598 A1 | 6/2008 | Bianco |
| 2008/0255035 A1 | 10/2008 | Trieu et al. |
| 2008/0280987 A1 | 11/2008 | Desai et al. |
| 2009/0018078 A1 | 1/2009 | Labhasetwar |
| 2009/0047337 A1 | 2/2009 | Mescheder et al. |
| 2009/0263483 A1 | 10/2009 | Desai et al. |
| 2009/0304805 A1 | 12/2009 | Desai et al. |
| 2010/0048499 A1 | 2/2010 | Desai et al. |
| 2010/0112077 A1 | 5/2010 | Desai et al. |
| 2010/0166869 A1 | 7/2010 | Desai et al. |
| 2010/0183728 A1 | 7/2010 | Desai et al. |
| 2010/0215751 A1 | 8/2010 | Desai et al. |
| 2010/0297243 A1 | 11/2010 | Desai et al. |
| 2011/0052708 A1 | 3/2011 | Soon-Shiong et al. |
| 2011/0118342 A1 | 5/2011 | De et al. |
| 2011/0151012 A1 | 6/2011 | Desai et al. |
| 2011/0165256 A1 | 7/2011 | Desai et al. |
| 2011/0196026 A1 | 8/2011 | De et al. |
| 2012/0004177 A1 | 1/2012 | Desai et al. |
| 2012/0039805 A1* | 2/2012 | Lisanti ............ A61K 31/415 424/9.1 |
| 2012/0070502 A1 | 3/2012 | Desai et al. |
| 2012/0128732 A1 | 5/2012 | Trieu et al. |
| 2012/0177743 A1 | 7/2012 | Desai et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |

(56) References Cited

U.S. PATENT DOCUMENTS

| | | |
|---|---|---|
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079177 A1 | 3/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |
| 2015/0313866 A1 | 11/2015 | Desai et al. |
| 2016/0008330 A1 | 1/2016 | Desai et al. |
| 2016/0015681 A1 | 1/2016 | Desai et al. |
| 2016/0015817 A1 | 1/2016 | Benettaib et al. |
| 2016/0151325 A1 | 6/2016 | Desai et al. |
| 2016/0228401 A1 | 8/2016 | Desai et al. |
| 2016/0374952 A1 | 12/2016 | Yeo et al. |
| 2017/0014373 A1 | 1/2017 | Desai et al. |
| 2017/0020824 A1 | 1/2017 | Desai et al. |
| 2017/0049711 A1 | 2/2017 | Desai et al. |
| 2017/0100344 A1 | 4/2017 | Desai et al. |
| 2017/0105951 A1 | 4/2017 | Desai et al. |
| 2017/0157035 A1 | 6/2017 | Seward et al. |
| 2017/0172975 A1 | 6/2017 | Desai et al. |
| 2017/0181988 A1 | 6/2017 | Desai et al. |
| 2017/0202782 A1 | 7/2017 | Pierce et al. |
| 2017/0224627 A1 | 8/2017 | Foss et al. |
| 2017/0333384 A1 | 11/2017 | Desai et al. |
| 2017/0340599 A1 | 11/2017 | Desai et al. |
| 2018/0015181 A1 | 1/2018 | Desai et al. |
| 2018/0064679 A1 | 3/2018 | Pierce et al. |
| 2018/0133157 A1 | 5/2018 | Desai et al. |
| 2018/0147139 A1 | 5/2018 | Seward et al. |
| 2018/0153820 A1 | 6/2018 | Desai et al. |
| 2018/0153863 A1 | 6/2018 | Desai |
| 2018/0169017 A1 | 6/2018 | Desai et al. |
| 2018/0177770 A1 | 6/2018 | Desai |
| 2018/0177771 A1 | 6/2018 | Desai |
| 2018/0214425 A1 | 8/2018 | Desai |
| 2018/0256551 A1 | 9/2018 | Desai et al. |
| 2018/0266335 A1 | 9/2018 | Zhu |
| 2018/0289620 A1 | 10/2018 | Desai et al. |
| 2018/0374583 A1 | 12/2018 | Goldstein et al. |
| 2019/0022020 A1 | 1/2019 | Desai |
| 2019/0054033 A1 | 2/2019 | Foss |
| 2019/0147986 A1 | 5/2019 | Luo |
| 2019/0167629 A1 | 6/2019 | Desai |
| 2019/0192477 A1 | 6/2019 | Desai |
| 2019/0247357 A1 | 8/2019 | Foss |
| 2019/0307732 A1 | 10/2019 | Desai |

FOREIGN PATENT DOCUMENTS

| | | |
|---|---|---|
| EP | 1 650 220 B1 | 4/2006 |
| EP | 1 862 179 A1 | 12/2007 |
| JP | 2006-524632 A | 11/2006 |
| JP | 2010-509331 A | 3/2010 |
| KR | 10-2007-0114753 | 12/2007 |
| MX | 2012002460 A | 5/2012 |
| TW | 201136584 A | 11/2011 |
| WO | WO-91/15193 A1 | 10/1991 |
| WO | WO-94/18954 A1 | 9/1994 |
| WO | WO-95/03036 A1 | 2/1995 |
| WO | WO-98/14174 A1 | 4/1998 |
| WO | WO-98/14175 A1 | 4/1998 |
| WO | WO-99/00113 A1 | 1/1999 |
| WO | WO-00/06152 A1 | 2/2000 |
| WO | WO-00/64437 A1 | 11/2000 |
| WO | WO-00/71079 A2 | 11/2000 |
| WO | WO-00/71079 A3 | 11/2000 |
| WO | WO-00/71163 A1 | 11/2000 |
| WO | WO-01/34174 A2 | 5/2001 |
| WO | WO-01/34174 A3 | 5/2001 |
| WO | WO-01/76567 A1 | 10/2001 |
| WO | WO-01/89522 A1 | 11/2001 |
| WO | WO-02/24179 A2 | 3/2002 |
| WO | WO-02/24179 A3 | 3/2002 |
| WO | WO-02/056912 A2 | 7/2002 |
| WO | WO-02/056912 A3 | 7/2002 |
| WO | WO-02/076459 A1 | 10/2002 |
| WO | WO-02/087545 A1 | 11/2002 |
| WO | WO-03/008665 A1 | 1/2003 |
| WO | WO-03/096944 A1 | 11/2003 |
| WO | WO-2004/017964 A1 | 3/2004 |
| WO | WO-2004/052401 A2 | 6/2004 |
| WO | WO-2004/052401 A3 | 6/2004 |
| WO | WO-2005/000266 A2 | 1/2005 |
| WO | WO-2005/000266 A3 | 1/2005 |
| WO | WO-2005/000900 A1 | 1/2005 |
| WO | WO-2005/039533 A1 | 5/2005 |
| WO | WO-2005/117952 A2 | 12/2005 |
| WO | WO-2005/117952 A3 | 12/2005 |
| WO | WO-2005/117978 A2 | 12/2005 |
| WO | WO-2005/117978 A3 | 12/2005 |
| WO | WO-2005/117986 A2 | 12/2005 |
| WO | WO-2005/117986 A3 | 12/2005 |
| WO | WO-2006/089290 A1 | 8/2006 |
| WO | WO-2006/090928 A1 | 8/2006 |
| WO | WO-2006/117220 A2 | 11/2006 |
| WO | WO-2006/117220 A3 | 11/2006 |
| WO | WO-2006/124684 A2 | 11/2006 |
| WO | WO-2006/124684 A3 | 11/2006 |
| WO | WO-2007/027819 A2 | 3/2007 |
| WO | WO-2007/027819 A3 | 3/2007 |
| WO | WO-2007/027941 A2 | 3/2007 |
| WO | WO-2007/027941 A3 | 3/2007 |
| WO | WO-2007/059116 A2 | 5/2007 |
| WO | WO-2007/107305 A2 | 9/2007 |
| WO | WO-2007/107305 A3 | 9/2007 |
| WO | WO-2007/148235 A2 | 12/2007 |
| WO | WO-2007/148235 A3 | 12/2007 |
| WO | WO-2008/128169 A1 | 1/2008 |
| WO | WO-2008/027055 A1 | 3/2008 |
| WO | WO-2008/057562 A1 | 5/2008 |
| WO | WO-2008/060651 A2 | 5/2008 |
| WO | WO-2008/060651 A3 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO-2008/150532 A1 | 12/2008 |
| WO | WO-2008/157353 A1 | 12/2008 |
| WO | WO-2009/126175 A1 | 10/2009 |
| WO | WO-2009/126401 A1 | 10/2009 |
| WO | WO-2009/126938 A1 | 10/2009 |
| WO | WO-2009/155659 A1 | 12/2009 |
| WO | WO-2010/068925 A1 | 6/2010 |
| WO | WO-2010/105172 A1 | 9/2010 |
| WO | WO-2010/118365 A1 | 10/2010 |
| WO | WO-2010/121000 A1 | 10/2010 |

(56) References Cited

FOREIGN PATENT DOCUMENTS

| | | |
|---|---|---|
| WO | WO-2011/025838 A1 | 3/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/149451 A1 | 11/2012 |
| WO | WO-2013/090634 A1 | 6/2013 |
| WO | WO-2014/110345 A1 | 7/2014 |
| WO | WO-2014/110408 A1 | 7/2014 |
| WO | WO-2014/110443 A1 | 7/2014 |
| WO | WO-2014/123612 A1 | 8/2014 |
| WO | WO-2014/143613 A1 | 9/2014 |
| WO | WO-2014/151853 A1 | 9/2014 |
| WO | WO-2014/159171 A1 | 10/2014 |

OTHER PUBLICATIONS

Suzouki et al. Impact of caveoli-1 expression on prognosis of pancreatic ductal adenocarcinoma. British Journal of Cancer, 2002, vol. 87, pp. 1140-1144.*
Wittkiewicz et al. Co-expression of fatty acid synthase and caveolin-1 in pancreatic ductal adenocarcinoma Implications for tumor progression and clinical outcome. Cell Cycle 7:19, 3021-3025, Oct. 1, 2008.*
Sunaga et al. Different Roles for Caveolin-1 in the Development of Non-Small Cell Lung Cancer versus Small Cell Lung Cancer. Cancer Research. vol. 64, Issue 12, pp. 4277-4285 (Year: 2004).*
Abou-Alfa, G. K. et al. (Sep. 20, 2006). "Randomized Phase III Study of Exatecan and Gemcitabine Compared with Gemcitabine Alone in Untreated Advanced Pancreatic Cancer," *J. Clin. Oncol.* 24(27):4441-4447.
Abraxis Bioscience, Inc. (Feb. 4, 2009). "ABRAXANE Now Available in Germany and the United Kingdom with Additional EU Countries to follow," Article located at URL http://web.archive.org/web/20090206124408/http://www.nanowerk.com/news/newsid=9156.php, last retrieved on Jul. 20, 2011, one page.
Abraxis Bioscience, Inc. (Mar. 17, 2010). "ABRAXANE Meets Primary Endpoint in Phase 3 Trial for Advanced Non-Small Cell Lung Cancer," Press Release located at http://www.biospace.com/news_print.aspx?NewsEntityId=174173, last visited May 3, 2010, 3 pages total.
Adis Data Information BV. (Aug. 28, 2004). "Paclitaxel [Taxol] and Liposomal Doxorubicin [Caelyx] Cotherapy Appears to be an Effective First-line Treatment in Patients with Metastatic Breast Cancer," *Inpharma* (1452):8.
Albain, K. S. et al. (Sep. 1991). "Survival Determinants in Extensive-Stage Non-Small-Cell Lung Cancer: The Southwest Oncology Group Experience," *J. Clin. Oncol.* 9(9):1618-1626.
Alberola, V. et al. (Sep. 1, 2003). "Cisplatin Plus Gemcitabine versus a Cisplatin-Based Triplet Versus Nonplatinum Sequential Doublets in Advanced Non-Small-Cell Lung Cancer: A Spanish Lung Cancer Group Phase III Randomized Trial," *J. Clin. Oncol.* 21(17):3207-3213.
Alberts, S. R. et al. (Oct. 2005). "PS-341 and Gemcitabine in Patients with Metastatic Pancreatic Adenocarcinoma: a North Central Cancer Treatment Group (NCCTG) Randomized Phase II Study," *Annals of Oncology* 16(10):1654-1661.
Allerton, J. P. et al. (Jun. 20, 2006). "A Phase II Evaluation of the Combination of Paclitaxel Protein-bound and Carboplatin in the First-line Treatment of Advanced Non-small Cell Lung Cancer (NSCLC)," Abstract, 2006 ASCO Annual Meeting Proceedings, Part 1, *J. Clin. Oncol.* 24(18 Suppl.): Abstract No. 7127, located at http://www.asco.org/portal/site/ASCO/template.RAW/menuitem . . . >, last visited on Oct. 1, 2008, one page.
American Cancer Society, (2009). "Cancer Facts and Figures," located at http://www.cancer.org/downloads/STT/500809web.pdf, pp. 1-72.
Anonymous (Oct. 7, 1995). "Chemotherapy in Non-Small Cell Lung Cancer: A Meta-Analysis Using Updated Data on Individual Patients From 52 Randomized Clinical Trials. Non-Small Cell Lung Cancer Collaborative Group," *Br. Med. J.* 311(7010):899-909.
Ashkenas, J. (Mar./Apr. 2003). "The Metronome Ticks On," *Preclinica*, located at <http://www.preclinica.com/default.asp?page=articles&issue=0303>, last visited on Apr. 29, 2007, pp. 1-2.
Belani, C. P. et al. (Aug. 1, 2003). "Multicenter, Randomized Trial for Stage IIIB or IV Non-Small-Cell Lung Cancer Using Weekly Paclitaxel and Carboplatin Followed by Maintenance Weekly Paclitaxel or Observation," *J. Clin. Oncol* .21(15):2933-2939.
Belani, C. P. et al. (Jan. 20, 2008). "Randomized, Phase III Study of Weekly Paclitaxel in Combination With Carboplatin Versus Standard Every-3-Weeks Administration of Carboplatin and Paclitaxel for Patients With Previously Untreated Advanced Non-Small-Cell Lung Cancer," *J. Clin. Oncol.* 26(3):468-473.
Berlin, J. D. et al. (Aug. 1, 2002). "Phase III Study of Gemcitabine in Combination With Fluorouracil Versus Gemcitabine Alone in Patients With Advanced Pancreatic Carcinoma: Eastern Cooperative Oncology Group Trial E2297," *J. Clin. Oncol.* 20(15):3270-3275.
Bertolini, F. et al. (Aug. 1, 2003). "Maximum Tolerable Dose and Low-Dose Metronomic Chemotherapy Have Opposite Effects on the Mobilization and Viability of Circulating Endothelial Progenitor Cells," *Cancer Res.* 63(15):4342-4346.
Bocci, G. et al. (Dec. 1, 2002). "Protracted Low-Dose Effects on Human Endothelial Cell Proliferation and Survival in Vitro reveal a Selective Antiangiogenic Window for Various Chemotherapeutic Drugs," *Cancer Res.* 62:6938-6943.
Bocci, G. et al. (Oct. 28, 2003). "Thrombospondin 1, a Mediator of the Antiangiogenic Effects of Low-dose Metronomic Chemotherapy," *Proc. Nat. Acad. Sci. USA* 100(22):12917-12922.
Bonomi, P. D. et al. (Nov. 1989). "Combination Chemotherapy Versus Single Agents Followed by Combination Chemotherapy in Stage IV Non-Small-Cell Lung Cancer: A Study of the Eastern Cooperative Oncology Group," *J. Clin. Oncol.* 7(11):1602-1613.
Bourgeois, H. et al. (Jun. 2006). "Phase I-II Study of Pegylated Liposomal Doxorubicin Combined With Weekly Paclitaxel as First-Line Treatment in Patients with Metastatic Breast Cancer," *Am. J. Clin. Oncol.* 29(3):267-275.
Bramhall, S. R. et al. (Jul. 15, 2002). "A Double-Blind Placebo-Controlled, Randomised Study Comparing Gemcitabine and Marimastat With Gemcitabine and Placebo as First Line Therapy in Patients With Advanced Pancreatic Cancer," *British J. Cancer* 87(2):161-167.
Bristol-Myers Squibb Company (Rev Jul. 2007). "TAXOL® (Paclitaxel) Injection, (Patient Information Included)," located at http://packageinserts.bms.com/pi/pi_taxol.pdf, last visited May 6, 2010, 55 pages.
Bunn, P. A. Jr. (Aug. 1989). "The Expanding Role of Cisplatin in the Treatment of Non-Small-Cell Lung Cancer," *Semin. Oncol.* 16(4)(Suppl. 6):10-21.
Carmeliet, P. et al. (Sep. 14, 2000). "Angiogenesis in Cancer and Other Diseases," *Nature* 407(6801):249-257.
Carter, D. C. et al. (1994). "Structure of Serum Albumin," Advances in Protein Chemistry. Schumaker, V.N., ed., Academic Press, Inc., San Diego, CA, 45:153-203.
Cascinu, S. et al. (Feb. 2003). "Weekly Gemcitabine and Cisplatin Chemotherapy: A Well-Tolerated but Ineffective Chemotherapeutic Regimen in Advanced Pancreatic Cancer Patients. A report from the Italian Group for the Study of Digestive Tract Cancer (GISCAD)," *Ann. Oncol.* 14(2):205-208.
Cerny, T. et al. (Aug. 1994). "Docetaxel (Taxotere™) is Active in Non-Small-Cell Lung Cancer: A Phase II Trial of the EORTC Early Clinical Trials ECTG)," *Br. J. Cancer* 70(2):384-387.
Chustecka, Z. et al. (Sep. 16, 2008). "New Drug Shows Promise in Pancreatic Cancer in Phase 2 Trial," *Medscape Medical News*, located at htpp://www.medscape.com/viewarticle/580571, last visited on Nov. 19, 2009, 2 pages.
Colucci, G. et al. (Feb. 15, 2002). "Gemcitabine Alone or with Cisplatin for the Treatment of Patients with Locally Advanced

(56) References Cited

OTHER PUBLICATIONS and/or Metastatic Pancreatic Carcinoma: A Prospective, Randomized Phase III Study of the Gruppo Oncologia dell'Italia Meridionale," Cancer 94(4):902-910.

Crinò, L. et al. (Nov. 1999). "Gemcitabine and Cisplatin versus Mitomycin, Ifosfamide, and Cisplatin in Advanced Non-Small-Cell Lung Cancer: A Randomized Phase III Study of the Italian Lung Cancer Project," *J. Clin. Oncol.* 17(11):3522-3530.

Curry, S. et al. (Sep. 1998). "Crystal Structure of Human Serum Albumin Complexed with Fatty Acid Reveals an Asymmetric Distribution of Binding Sites," *Nat. Struct. Biol* 5(9):827-835.

Damascelli, B. et al. (Nov. 15, 2001). "Intraarterial Chemotherapy with Polyoxyethylated Castor Oil Free Paclitaxel, Incorporated in Albumin Nanoparticles (ABI-007)," Cancer 92(10):2592-2602.

Damascelli, B. et al. (Jul. 2003). "A Novel Intraarterial Chemotherapy Using Paclitaxel in Albumin Nanoparticles to Treat Advanced Squamous Cell Carcinoma of the Tongue: Preliminary Findings," AJR 181:253-260.

Dennis, A. et al. (2007). "hERG Channel Trafficking: Novel Targets in Drug-Induced Long QT Syndrome," *Biochem. Soc. Trans.* 35(5):1060-1063.

Depierre, A. et al. (Mar. 1988). "Phase II Study of Navelbine (NVB) in Non Small Cell Lung Cancer (NSCLC)," *Proc. Am. Soc. Clin. Oncol*, 24$^{th}$ Annual Meeting of the American Society of Clinical Oncology (ASCO), May 22-24, 1988, Proceedings of ASCO, New Orleans, Louisiana, vol. 7, p. 201, Abstract No. 778.

Desai, N. et al. (Jul. 2003). "Oral Bioavailability of Paclitaxel in a Novel, Cremophor El-free, Protein-based Nanoparticle Preparation," *Proc. Amer. Assn. for Cancer Res.* 44(2):732, Abstract presented at the 94$^{th}$ Annual Meeting of ASCR, Jul. 11-14, 2003, Washington, Washington, D.C., vol. 44, 2nd edition, Abstract No. 3673, 3 pages.

Desai, N. et al. (Feb. 15, 2006). "Increased Antitumor Activity, Intratumor Paclitaxel Concentrations, and Endothelial Cell Transport of Cremophor-Free, Albumin-Bound Paclitaxel, ABI-007, Compared With Cremophor-Based Paclitaxel," *Clin. Cancer Res.* 12(4):1317-1324.

Desai, N. et al. (Jun. 2009). "SPARC Expression Correlates With Tumor Response to Albumin-Bound Paclitaxel in Head and Neck Cancer Patients," *Translational Oncology* 2(2):59-64.

De Vos, A. I. et al. (Nov. 1997). "Differential Modulation of Cisplatin Accumulation in Leukocytes and Tumor Cell Lines by the Paclitaxel Vehicle Cremophor EL," *Ann. Onc.* 8(11):1145-1150.

Du Bois, A. et al. (1997). "Phase I/II Study of the Combination of Carboplatin and Paclitaxel as First-line Chemotherapy in Patients with Advanced Epithelial Ovarian Cancer," *Ann. Oncol.* 8:355-361.

Di Costanzo, F. et al. (2009). "Targeted Delivery of Albumin Bound Paclitaxel in the Treatment of Advanced Breast Cancer," *OncoTargets and Therapy* 2:179-188.

Dubey, S. et al. (Feb. 2004). "Chemotherapy for Advanced Non-Small Cell Lung Cancer," *Hematol. Oncol. Clin. N. Am.* 18(1):101-114.

Edge, S. B. (eds) et al. (2010). "Lung (Carcinoid Tumors are Included. Sarcomas and Other Rare Tumors are not included)," in Chapter 25 in *AJCC Cancer Staging Manual*, Seventh Edition, American Joint Committee on Cancer, Springer, Chicago, IL, pp. 253-270.

Ellerby, H. M. et al. (Sep. 1999). "Anti-Cancer Activity of Targeted Pro-Apoptotic Peptides," *Nat. Med.* 5(9):1032-1038.

Fehske, K. J. et al. (Jan. 1, 1981). "The Location of Drug Binding Sites in Human Serum Albumin," *Biochemical Pharmacology* 30(7):687-692.

Ficker, E. et al. (Jun. 27, 2003, e-pub. May 29, 2003). "Role of the Cytosolic Chaperones Hsp70 and Hsp90 in Maturation of the Cardiac Potassium Channel hERG," *Circ. Res.* 92:e87-e100.

Ficker, E. et al. (2005). "hERG Channel Trafficking," in *The hERG Cardiac Potassium Channel: Structure, Function and Lonq QT Syndrome*, Wiley, Chichester, (Novartis Foundation Symposium 266), pp. 57-74, 95-99.

Finlayson, J. S. (1980). "Albumin Products," in *Seminars in Thrombosis and Hemostasis*, Mammen, E. F. (ed.), Stratton Intercontinental Medical Book Corporation, New York, NY, vol. VI, No. 2, pp. 85-120.

Fleming, G. F. et al. (Jun. 1, 2004). "Phase III Trial of Doxorubicin Plus Cisplatin With or Without Paclitaxel Plus Filgrastim in Advanced Endometrial Carcinoma: a Gynecologic Oncology Group Study," *J. Clin. Oncol.* 22(11):2159-2166.

Fossella, F. V. et al. (Mar. 1995). "Phase II Study of Docetaxel for Advanced or Metastatic Platinum-Refractory Non-Small-Cell Lung Cancer," *J. Clin. Oncol.* 13(3):645-651.

Fossella, F. et al. (Aug. 15, 2003). "Randomized, Multinational, Phase III Study of Docetaxel Plus Platinum Combinations Versus Vinorelbine Plus Cisplatin for Advanced Non-Small-Cell Lung Cancer: the TAX 326 Study Group," *J. Clin. Oncol.* 21(16):3016-3024.

Fujimoto-Ouchi, K. et al. (Apr. 2001). "Schedule of Dependency of Antitumor Activity in Combination Therapy with Capecitabine/ 5'Deoxy-5-Fluorouridine and Docetaxel in Breast Cancer Models," *Clin. Cancer Res.* 7:1079-1086.

Fulfaro F. et al. (Jul. 15, 2004). "Weekly Paclitaxel (T) and Pegylated Liposomal Doxorubicin (PLD) as First Line Treatment in Metastatic Breast Cancer (MBC) Patients," *J. Clin. Oncol.* 22(14S):535, Abstract No. 704.

Gatzemeier, U. et al. (Jun. 1995). "Phase II Study With Paclitaxel for the Treatment of Advanced Inoperable Non-Small Cell Lung Cancer," *Lung Cancer* 12(Suppl. 2):S101-S106.

Gatzemeier, U. et al. (Oct. 1, 2000). "Phase III Comparative Study of High-Dose Cisplatin Versus a Combination of Paclitaxel and Cisplatin in Patients With Advanced Non-Small-Cell Lung Cancer," *J. Clin. Oncol.* 18(19):3390-3399.

Gelderblom, H. et al. (2001). "Cremophor EL: The Drawbacks and Advantages of Vehicle Selection for Drug Formulation," *Eur. J. Cancer* 37:1590-1598.

Gelderblom, H. et al. (Apr. 2002). "Influence of Cremophor EL on the Bioavailability of Intraperitoneal Paclitaxel," *Clin. Cancer Res.* 8(4):1237-1241.

GEMZAR® (Gemcitabine HCl) for Injection Product Label, (revised May 7, 2007). Description, Eli Lilly and Company, IN 46285, 10 pages.

Gradishar, W. J. et al. (Nov. 1, 2005). "Phase III Trial of Nanoparticle Albumin-Bound Paclitaxel Compared with Polyethylated Castor Oil-Based Paclitaxel in Women With Breast Cancer," *J. Clin. Oncol.* 23(31):7794-7803.

Green, M. R. et al. (Aug. 2006, epub: Jun. 1, 2006). "Abraxane®, A Novel Cremophor®-Free, Albumin-Bound Particle Form of Paclitaxel for the Treatment of Advanced Non-Small-Cell Lung Cancer," *Ann. Oncol.* 17(8):1263-1268.

Grilli, R. et al. (Oct. 1993). "Chemotherapy for Advanced Non-Small-Cell Lung Cancer: How Much Benefit is Enough?" *J. Clin. Oncol.* 11(10):1866-1872.

Hainsworth, J. D. et al. (Jul. 1995). "Paclitaxel by 1-Hour Infusion: An Active Drug in Metastatic Non-Small Cell Lung Cancer," *J. Clin. Oncol.* 13(7):1609-1614.

Harries, M. et al. (Nov. 1, 2005). "Nanoparticle Albumin-Bound Paclitaxel for Metastatic Breast Cancer," *J. Clin. Oncol.* 23(31):7768-7771.

Hauser, C. J. et al. (Jun. 1980). "Oxygen Transport Responses to Colloids and Crystalloids in Critically Ill Surgical Patients," *Surgery, Gynecology and Obstetrics* 150(6):811-816.

Hawkins, M. J. et al. (Jun. 20, 2006). "Dose Escalation Study of Nab-Paclitaxel Followed by Carboplatin as First Line Therapy in Advanced Non Small Cell Lung Cancer (NSCLC)," Abstract from the 2006 *ASCO Annual Meeting Proceedings*, Part 1, *J. Clin. Oncol.* 24(18 Suppl.): Abstract No. 7132 located at http://www.asco.org/ portal/site/ASCO/template.RAW/menuitem . . . >, last visited on Oct. 1, 2008, 2 pages.

Hawkins, M. J. et a. (Jun. 20, 2007). "Study of Three Weekly Nab-Paclitaxel Regimens in Combination With Carboplatin as First-Line Therapy in Advanced Non Small Cell Lung Cancer (NSCLC)," Abstract from the 2007 ASCO Annual Meeting Proceedings, Part 1, *Supplement to J. Clin. Oncol.* 25(18 Suppl.): Abstract No. 7659 now relocated at http://www.asco.org/ascov2/

(56) References Cited

OTHER PUBLICATIONS

Meetings/Abstracts?&vmview=abst_detail_view&confID=47&abstractID=34198, p. 424s, 2 pages.

Hawkins, M. J. et al. (Sep. 2007). "High-Dose 130-Nanometer Albumin-Bound Paclitaxel in Combination with Carboplatin as First-Fine Therapy in Advanced Non-Small Cell Lung Cancer," Poster No. 6563, *Eur. J. Cancer Supplements* 5(4):376-377.

He, X. M. et al. (Jul. 16, 1992). "Atomic Structure and Chemistry of Human Serum Albumin," *Nature* 358(6383):209-215.

Heinemann, V. et al. (Aug. 20, 2006). "Randomized Phase III Trial of Gemcitabine Plus Cisplatin Compared with Gemcitabine Alone in Advanced Pancreatic Cancer," *J. Clin. Oncol.* 24(24):3946-3952.

Herbst, R. S. et al. (Mar. 1, 2004). "Gefitinib in Combination With Paclitaxel and Carboplatin in Advanced Non-Small-Cell Lung Cancer: A Phase III Trial—INTACT 2," *J. Clin. Oncol.* 22(5):785-794.

Herrmann, R. et al. (Jun. 1, 2007). "Gemcitabine Plus Capecitabine Compared with Gemcitabine Alone in Advanced Pancreatic Cancer: A Randomized, Multicenter, Phase III Trial of the Swiss Group for Clinical Cancer Research and the Central European Cooperative Oncology Group," *J. Clin. Oncol.* 25(16):2212-2217.

Hudis, C. et al. (Jan. 1999). "Sequential Dose-Dense Doxorubicin, Paclitaxel, and Cyclophosphamide for Resectable High-Risk Breast Cancer: Feasibility and Efficacy," *J. Clin. Oncol.* 17(1):93-100.

Hudis, C. (Aug. 20, 2005). "Testing Chemotherapy for Breast Cancer: Timing is Everything," *J. Clin. Oncol.* 23(24):5434-5436.

Ibrahim, N. K. et al. (May 2002). "Phase I and Pharmacokinetic Study of ABI-007, a Cremophor-Free, Protein-Stabilized, Nanoparticle Formulation of Paclitaxel," *Clin. Cancer Res.* 8:1038-1044.

Ibrahim, N. K. et al. (Sep. 1, 2005). "Multicenter Phase II Trial of ABI-007, an Albumin-Bound Paclitaxel, in Women With Metastatic Breast Cancer," *J. Clin. Oncol.* 23(25):6019-6026.

Jafar, N. et al. (Apr. 19, 2010). "Caveolin-1 Inhibits Survivin and Increases Sensitivity to Paclitaxel in Breast Cancer Cells," Abstract from the AACR $101^{st}$ Annual Meeting 2010, Meeting held on Monday, Apr. 19, 2010, in Washington D.C., Poster Section 23, Poster Board No. 4, Abstract 2547, one page.

Jimenez, J. J. et al. (Jan. 15, 1992). "Protection from 1-β-D-Arabinofuranosylcytosine-Induced Alopecia by Epidermal Growth Factor and Fibroblast Growth Factor in the Rat Model," *Cancer Res.* 52(2):413-415.

Johnson, D. H. et al. (Jul. 1996). "Paclitaxel Plus Carboplatin in Advanced Non-Small-Cell Lung Cancer: A Phase II Trial," *J. Clin. Oncol.* 14(7):2054-2060.

Jones, C. M. et al. (Oct. 18, 2007). "Targeted Therapies for NSCLC," from US Pharm. 32(10):5-13, full article located at http://www.uspharmacist.com/content/t/oncology/c/10219/, last visited on Nov. 11, 2010, 9 pages.

Jones, V. et al. (2000). "Phase II Study of Weekly Paclitaxel (Taxol) and Liposomal Doxorubicin (Doxil) in Patients with Locally Advanced and Metastatic Breast Cancer," Abstract from the $36^{th}$ ASCO Annual Meeting Proceedings, held in New Orleans, Louisiana, on May 20-23, 2000, *Proc. Amer. Soc. Clin. Oncol.* 19:116a, Abstract No. 451.

Keedy, V. L. et al. (May 20, 2010). "A Phase I Study of Nab-Paclitaxel (Nab-P) With Carboplatin (C) and Thoracic Radiation (TR) in Patients With Locally Advanced NSCLC," Abstract from the 2010 *ASCO Annual Meeting Proceedings*, held in Chicago, IL, on Jun. 4-8, 2010, published in the *Supplement to J. Clin. Oncol.* vol. 28, No. 15S, Part I of II, and also located at http://www.asco.org/ascov2/Meetings/Abstracts?&vmview=abst_detail_view&confID=74&abstractID=48407, Abstract No. e17504, 5 pages.

Kelly, W. K. et al. (Apr. 1993). "Prostate-Specific Antigen as a Measure of Disease Outcome in Metastatic Hormone-Refractory Prostate Cancer," *J. Clin. Oncol.* 11(4):607-615.

Kelly, K. et al. (Jul. 1, 2001). "Randomized Phase III Trial of Paclitaxel Plus Carboplatin Versus Vinorelbine Plus Cisplatin in the Treatment of Patients With Advanced Non-Small-Cell-Lung Cancer: A Southwest Oncology Group Trial," *J. Clin. Oncol.* 19(13):3210-3218.

Kim, B. Y. S. et al. (Dec. 16, 2010). "Nanomedicine," *N. Eng. J. Med.* 363(25):2434-2443.

Kim, S.-O. et al. (2005). "Superior Antitumor Efficacy of Genexol®-PM, a Biodegradable Polymeric Micelle-Based Formulation of Paclitaxel (Genexol®) Compared with Gemzar® (Gemcitabine) and Taxol® in Human Pancreatic Cancer Cells in Vitro and in Vivo," Experimental and Molecular Therapeutics 10: Drug Targeting, *Proc. Amer. Assoc. Cancer Res.*, vol. 46, Abstract No. 1440, 2 pages, located at http://www.aacrmeetingabstracts.org/cgi/content/abstract/2005/1/337-b, last visited on Feb. 22, 2010.

Kim, Y.-N. et al. (2002). "Caveolin-1 Phosphorylation in Human Squamous and Epidermoid Carcinoma Cells: Dependence on ErbB1 Expression and Src Activation," *Exp.Cell Res.* 280:134-147.

Klement, G. et al. (Jan. 2002). "Differences in Therapeutic Indexes of Combination Metronomic Chemotherapy and an Anti-VEGFR-2 Antibody in Multidrug-Resistant Human Breast Cancer Xenografts," *Clin. Cancer. Res.* 8(1):221-232.

Ko, A. et al. (2005, e-pub: Jul. 5, 2005). "Serum CA19-9 Response as a Surrogate for Clinical Outcome in Patients Receiving Fixed-Dose Rate Gemcitabine for Advanced Pancreatic Cancer," *British Journal of Cancer* 93:195-199.

Kolodgie, F. D. et al. (Sep. 3, 2002, epub: Aug. 19, 2002). "Sustained Reduction of in-Stent Neointimal Growth With the Use of a Novel Systemic Nanoparticle Paclitaxel," *Circulation* 106(10):1195-1198.

Kondrateva, A. P. (2001). The Combination of Radiation and Drug Therapies for the Organ Safe Treating of Malignant Tumors, *Modern Oncology* 3(3), located at http://www.consilium-medicum.com/magazines/cm/pediatrics/article/8403, in Russian, with English translation (author translated as A. P. Kondratieff) (from translategoogle.com), 6 pages total.

Kosmidis, P. et al. (Sep. 1, 2002). "Paclitaxel Plus Carboplatin Versus Gemcitabine Plus Paclitaxel in Advanced Non-Small-Cell Lung Cancer: A Phase III Randomized Trial," *J. Clin. Oncol.* 20(17):3578-3585.

Koukourakis, M. I. et al. (Sep. 1, 2003, epub: Sep. 18, 2003). "Enhanced Expression of SPARC/Osteonectin in the Tumor-Associated Stroma of Non-Small Cell Lung Cancer is Correlated With Markers of Hypoxia/Acidity and With Poor Prognosis of Patients," *Cancer Res.* 63(17):5376-5380.

Langer, C. J. et al. (Aug. 1995). "Paclitaxel by 24- or 1-Hour Infusion in Combination with Carboplatin in Advanced Non-Small Cell Lung Cancer: The Fox Chase Cancer Center Experience," *Semin. Oncol.* 22(4-Suppl. 9):18-29.

Langer, C. J. et al. (Dec. 1996). "Combination Paclitaxel (1-Hour) and Carboplatin (AUC 7.5) in Advanced Non-Small Cell Lung Cancer: A Phase II Study by the Fox Chase Cancer Center Network," *Semin. Oncol.* 23(6-Suppl. 16):35-41.

Langer, C. J. et al. (Jun. 2008). "Phase III Trial Comparing Paclitaxel Poliglumex (CT-2103, PPX) in Combination with Carboplatin Versus Standard Paclitaxel and Carboplatin in the Treatment of PS 2 Patients with Chemotherapy-Naïve Advanced Non-Small Cell Lung Cancer," *J. Thorac. Oncol.* 3(6):623-630.

Le Chevalier, T. et al. (Feb. 1994). "Randomized Study of Vinorelbine and Cisplatin Versus Vindesine and Cisplatin versus Vinorelbine Alone in Advanced Non-Small-Cell Lung Cancer: Results of a European Multicenter Trial Including 612 Patients," *J. Clin. Oncol.* 12(2):360-367.

Leong, S.-S. et al. (Feb. 1, 2005, epub: Dec. 20, 2004). "Paclitaxel, Carboplatin, and Gemcitabine in Metastatic Nasopharyngeal Carcinoma: A Phase II Trial Using a Triplet Combination," *Cancer* 103(3):569-575.

Levine, M. N. et al. (Published Ahead of Print on Apr. 30, 2012). "Method to Our Madness or Madness in Our Method? Pitfalls in Trial Methodology," *J. Clin. Oncol.* vol. 30, 3 pages.

Li, C. et al. (Jun. 1, 1998). "Complete Regression of Well-Established Tumors Using a Novel Water-Soluble Poly(L-Glutamic Acid)-Paclitaxel Conjugate," *Cancer Research* 58:2404-2409.

Li, C. et al. (Jul. 2000). "Tumor Irradiation Enhances the Tumor-Specific Distribution of Poly(L-Glutamic Acid)-Conjugated Paclitaxel and Its Antitumor Efficacy," *Clin. Cancer Res.* 6(7):2829-2834.

(56) References Cited

OTHER PUBLICATIONS

Li, C. et al. (May 22, 2008). "Polymer-Drug Conjugates: Recent Development in Clinical Oncology," *Adv. Drug Deliv. Rev.* 60(8):886-898, 24 pages.

Lilenbaum, R. C. et al. (2002). "Single-Agent (SA) Versus Combination Chemotherapy (CC) in Advanced Non-Small Cell Lung Cancer (NSCLC): A CALGB Randomized Trial of Efficacy, Quality of Life (QOL), and Cost-Effectiveness," *Proc. Am. Soc. Clin. Oncol.* Abstract presented at the 2002 *ASCO Annual Meeting Proceeding*, relocated at http://jco.ascopubs.org/content/23/1/190.full, Jun. 2002, vol. 21, Abstract No. 2, 2 pages.

Loehr, M. et al. (2009). "Cationic Liposomal Paclitaxel in Combination with Gemcitabine in Patients with Advanced Pancreatic Cancer: A Phase II Trial," Abstract presented at the 2009 *ASCO Annual Meeting Proceedings* (Post-Meeting Edition), published in *J. Clin. Oncol.* vol. 27, No. 15S, May 20 Supplement, Abstract No. 4526, located http://meeting.ascopubs.org/cgi/content/abstract/27/15S/4526, last visited on Feb. 22, 2010, 2 pages.

Lorenz, W. et al. (Mar. 1977). "Histamine Release in Dogs by Cremophor El® and Its Derivatives: Oxethylated Oleic Acid is the Most Effective Constituent," *Agents and Actions* 7(1):63-67.

Louvet, C. et al. (Mar. 15, 2002). "Gemcitabine combined With Oxaliplatin in Advanced Pancreatic Adenocarcinoma: Final Results of a GERCOR Multicenter Phase II Study," *J. Clin. Oncol.* 20(6):1512-1518.

Louvet, C. et al. (May 20, 2005). "Gemcitabine in Combination with Oxaliplatin Compared with Gemcitabine Alone in Locally Advanced or Metastatic Pancreatic Cancer: Results of a GERCOR and GISCAD Phase III Trial," *J. Clin. Oncol.* 23(15):3509-3516.

Lowry, F. (Nov. 2008). "Drug Combo Shrinks Pancreatic Tumors in Phase I Trial," *GI & Hepatology News*, p. 14.

Lynch, T. Jr. et al. (2005). "Optimizing Chemotherapy and Targeted Agent Combinations in NSCLC," *Lung Cancer* 50 (Suppl. 2):S25-S32.

Lynch, T. J. et al. (Feb. 20, 2010, epub: Jan. 25, 2010). "Cetuximab and First-Line Taxane/Carboplatin Chemotherapy in Advanced Non-Small-Cell Lung Cancer: Results of the Randomized Multicenter Phase III Trial BMS099," *J. Clin. Oncol.* 28(6):911-917.

Maitra, A. et al. (Dec. 10, 2009). "Abstract C246: nab®-Paclitaxel Targets Tumor Stroma and Results, Combined with Gemcitabine, in High Efficacy Against Pancreatic Cancer Models," *Molecular Cancer Therapeutics* 8 (Meeting Abstract Supplement), C246, Abstract presented at the *AACR-NCI-EORTC International Conference on Molecular Targets and Cancer Therapeutics*, held on Nov. 15-19, 2009, Boston, MA, abstract located at http://mct.aacrjournals.org/cgi/content/meeting_abstract/8/12_MeetingAbstracts/C246?sid=2cd1379d-eb9e-4215-94ed-b34b968c25ec, last visited on Feb. 22, 2010, 2 pages.

Mavroudis, D. et al. (2002). "Phase I Study of Paclitaxel (Taxol) and Pegylated Liposomal Doxorubicin (Caelyx) Administered Every 2 Weeks in Patients with Advanced Solid Tumors," *Oncology* 62:216-222.

Micha, J. P. et al. (Feb. 2006, e-pub: Oct. 14, 2005). "Abraxane in the Treatment of Ovarian Cancer: the Absence of Hypersensitivity Reactions," *Gynecol. Oncol.* 100(2):437-438, 2 pages.

Modiano, M. et al. (1999). "Phase I Study of DOXIL® (Pegylated Liposomal Doxorubicin) Plus Escalating Doses of TAXOL® in the Treatment of Patients with Advanced Breast or Gynecologic Malignancies," *Proc. Amer. Soc. Clin. Oncol.*18:220a, Abstract No. 848.

Mondesire, W. H. et al. (Oct. 15, 2004, epub: Oct. 22, 2004). "Targeting Mammalian Target of Rapamycin Synergistically Enhances Chemotherapy-Induced Cytotoxicity in Breast Cancer Cells," *Clin. Cancer Res.* 10(20):7031-7042.

Moore, M. J. et al. (May 20, 2007). "Erlotinib Plus Gemcitabine Compared with Gemcitabine Alone in Patients with Advanced Pancreatic Cancer: A Phase III Trial of the National Cancer Institute of Canada Clinical Trials Group," *J. Clin.Oncol.* 25(15):1960-1966.

Moreno-Aspitia, A. et al. (2005). "Nanoparticle Albumin-bound Paclitaxel (ABI-007): a Newer Taxane Alternative in Breast Cancer," *Future Oncol.* 1(6):755-762.

Moreno-Aspitia, A. et al. (Oct. 2005). "North Central Cancer Treatment Group N0531: Phase II Trial of Weekly Albumin-Bound Paclitaxel (ABI-007, Abraxane®) in Combination with Gemcitabine in Patients with Metastatic Breast Cancer," *Clinical Breast Cancer* 6(4):361-364.

Nasu, Y. et al. (Sep. 1998). "Suppression of Caveolin Expression Induces Androgen Sensitivity in Metastatic Androgen-Insensitive Mouse Prostate Cancer Cells," *Nat. Med.* 4(9):1062-1064.

Ng, S. S. W. et al. (Feb. 1, 2004, e-pub: Feb. 10, 2004). "Taxane-Mediated Antiangiogenesis in Vitro: Influence of Formulation Vehicles and Binding Proteins," *Cancer Res.* 64:821-824.

Nieto, J. et al. (2008). "Metastatic Pancreatic Cancer 2008: Is the Glass Less Empty?" *The Oncologist* 13:562-576.

Novelos Therapeutics, Inc. (2010). "NOV-002, Cancer," located at http://www.novelos.com/html/our_products/BAM_002.htm, last visited on May 6, 2010, 4 pages.

Nyman, D. W. et al. (Nov. 1, 2005). "Phase I and Pharmacokinetics Trial of ABI-007, a Novel Nanoparticle Formulation of Paclitaxel in Patients with Advanced Nonhematologic Malignancies," *J. Clin. Oncol.* 23(31):7785-7793.

Oettle, H. et al. (Oct. 2005, epub: Aug. 8, 2005). "A Phase III Trial of Pemetrexed Plus Gemcitabine Versus Gemcitabine in Patients With Unresectable or Metastatic Pancreatic Cancer," *Annals of Oncology*, 16(10):1639-1645.

Onn, A. et al. (2004). "Treatment of Non-Small-Cell Lung Cancer: A Perspective on the Recent Advances and the Experience with Gefitinib," *Br. J. Cancer* 91(Suppl 2):S11-S17.

O'Reilly, M. S. et al. (Oct. 21, 1994). "Angiostatin: A Novel Angiogenesis Inhibitor That Mediates the Suppression of Metastases by a Lewis Lung Carcinoma," *Cell* 79(2):315-328.

O'Reilly, M. S. et al. (Jan. 24, 1997). "Endostatin: An Endogenous Inhibitor of Angiogenesis and Tumor Growth," *Cell* 88(2):277-285.

O'Shaughnessy, J. A. et al. (2004). "Weekly Nanoparticle Albumin Paclitaxel (Abraxane) Results in Long-Term Disease Control in Patients With Taxane-Refractory Metastatic Breast Cancer," *Breast Cancer Research and Treatment, 27th Annual Charles A. Coltman San Antonio Breast Cancer Symposium*, San Antonio, Texas, Dec. 8-11, 2004, 88(Suppl. 1):S65, Abstract No. 1070.

Paál, K. et al. (2001). "High Affinity Binding of Paclitaxel to Human Serum Albumin," *Eur. J. Biochem.* 268(7):2187-2191.

Paccagnella, A. et al. (Dec. 1996). "Paclitaxel and Carboplatin: A Phase I Study in Advanced Non-Small Cell Lung Cancer," *Semin. Oncol.* 23(6)(Suppl. 16):76-79.

Papyan, A. et al. (2004). "MBT-0206 Enhances the Anti-Tumor Treatment in a Highly Metastatic Human Pancreatic Cancer Mouse Model," *Proc. Amer. Assoc. Cancer Res.* vol. 45, Cellular, Molecular, and Tumor Biology 80: Angiogenesis Inhibitors III, Abstract No. 4104, located at http://aacrmeetingabstracts.org/cgi/content/abstract/2004/1/947-c, last visited Feb. 22, 2010, 2 pages.

Pectasides, D. et al. (2005). "Comparison of Docetaxel and Docetaxel-Irinotecan Combination as Second-Line Chemotherapy in Advanced Non-Small-Cell Lung Cancer: A Randomized Phase II Trial," *Annals of Oncology* 16:294-299.

Perabo, F. G. et al. (Nov.-Dec. 2003). "Preclinical Evaluation of Gemcitabine/Paclitaxel-Interactions in Human Bladder Cancer Lines," *Anticancer Res.* 23(6C):4805-4814, Abstract only located at http://www.ncbi.nlm.nih.gov/pubmed/14981929, last visited on Jan. 11, 2010, one page.

Pirker, R. et al. (May 2, 2009). "Cetuximab Plus Chemotherapy in Patients with Advanced Non-Small-Cell Lung Cancer (FLEX): An Open-Label Randomised Phase III Trial," *Lancet* 373:1525-1531.

Porter, P. L. et al. (Aug. 1995). "Distribution of SPARC in Normal and Neoplastic Human Tissue," *J. Histochem. and Cytochem.* 43(8):791-800.

Raspaglio, G. et al. (Jan. 1, 2005). "Thiocolchicine Dimers: A Novel Class of Topoisomerase-I Inhibitors," *Biochem. Pharmacol.* 69(1):113-121, Abstract only located at http://www.ncbi.nlm.nih.gov/pubmed/15588720, last visited on Jan. 11, 2010, one page.

Reynolds, C. et al. (Jun. 20, 2007). "An Open-Label, Phase II Trial of Nanoparticle Albumin Bound Paclitaxel (Nab-paclitaxel), Carboplatin, and Bevacizumab in First-Line Patients with Advanced Non-squamous Non-Small Cell Lung Cancer (NSCLC)," Abstract from the 2007 *ASCO Annual Meeting Proceedings*, Part 1, *J. Clin. Oncol.*

(56) References Cited

OTHER PUBLICATIONS

25(18 Suppl.): Abstract No. 7610, located at http://www.asco.org/portal/site/ASCO/template.RAW/menuitem . . . , last visited on Oct. 1, 2008, two pages.
Reynolds, C. et al. (Dec. 2009). "Phase II Trial of Nanoparticle Albumin-Bound Paclitaxel, Carboplatin, and Bevacizumab in First-Line Patients With Advanced Nonsquamous Non-Small Cell Lung Cancer," *J. Thoracic Oncol.* 4(12):1537-1543.
Rigas, J. R. (Jun. 2, 2004). "Taxane-Platinum Combinations in Advanced Non-Small Cell Lung Cancer: A Review," *The Oncologist* 9(Suppl. 2):16-23.
Rizvi, N. A. et al. (Jun. 20, 2006). "Phase I/II Study of ABI-007 as First Line Chemotherapy in Advanced Non-Small Cell Lung Cancer (NSCLC)," *J. Clin. Oncol. 2006 ASCO Annual Meeting Proceedings*, Part I, vol. 24, No. 18S, (Jun. 20 Supplement), Abstract located at http://www.asco.org/ascov2/Meetings/Abstracts?&vmview=abst_detail_view&confID=40&abstractID=32992, last visited on Jul. 18, 2012, Abstract No. 7105, 3 pages.
Rizvi, N. A. et al. (Feb. 1, 2008). "Phase I/II Trial of Weekly Intravenous 130-nm Albumin-Bound Paclitaxel as Initial Chemotherapy in Patients with Stage IV Non-Small-Cell Lung Cancer," *J. Clin. Oncol.* 26(4):639-643.
Robert, N. et al. (Dec. 2005). "Pilot Study of Dose Dense Doxorubicin Plus Cyclophosphamide Followed by ABI-007 in Patients with Early Stage Breast Cancer," *Breast Cancer Research and Treatment, Special Issue from the 28$^{th}$ Annual San Antonio Breast Cancer Symposium*, San Antonio, TX, Dec. 8-11, 2005, Abstract—Poster Session II, p. S109, Abstract No. 2073, 3 pages.
Rocha-Lima, C. M. et al. (Sep. 15, 2004). "Irinotecan Plus Gemcitabine Results in No Survival Advantage Compared with Gemcitabine Monotherapy in Patients with Locally Advanced or Metastatic Pancreatic Cancer Despite Increased Tumor Response Rate," *J. Clin. Oncol.* 22(18):3776-3783.
Roche Laboratories, Inc. (Apr. 2006). "Xeloda® (Capecitabine) Tablets Product Insert," 43 pages.
Roe, S. M. et al. (Jan. 28, 1999, e-pub: Jan. 9, 1999). "Structural Basis for Inhibition of the Hsp90 Molecular Chaperone by the Antitumor Antibiotics Radicicol and Geldanamycin," *J. Med. Chem.* 42(2):260-266.
Romond, E. H. et al. (2005). "Combined Analysis of NSABP-B-31 and NCCTG-N9381: Disease-Free and Overall Survival Data," *Breast Cancer Update* 4(6):15-19.
Rosell, R. et al. (2002). "Phase III Randomised Trial Comparing Paclitaxel/Carboplatin with Paclitaxel/Cisplatin in Patients with Advanced Non-Small-Cell Lung Cancer: A Cooperative Multinational Trial," *Ann. Oncol.* 13:1539-1549.
Safran, H. et al. (Sep. 1, 2002). "Gemcitabine, Paclitaxel, and Radiation for Locally Advanced Pancreatic Cancer: A Phase I Trial," *Int. J. Radiation Oncol. Biol. Phys.* 54(1):137-141.
Sandler, A. B. et al. (Jan. 2000). "Phase III Trial of Gemcitabine Plus Cisplatin Versus Cisplatin Alone in Patients with Locally Advanced or Metastatic Non-Small-Cell Lung Cancer," *J. Clin. Oncol.* 18(1):122-130.
Sandler, A. et al. (Dec. 14, 2006). "Paclitaxel-Carboplatin Alone or With Bevacizumab for Non-Small-Cell Lung Cancer," *New Eng. J. Med.* 355(24):2542-2550.
Sausville, E. A. et al. (Oct. 2003). "Clinical Development of 17-Allylamino, 17-Demethoxygeldanamycin," *Curr. Cancer Drug Targets* 3(5):377-383, Abstract only located at http:www.ncbi.nlm.nih.gov/pubmed/14529389, last visited on Jan. 28, 2010, one page.
Sawada, N. et al. (Apr. 1998). "Induction of Thymidine Phosphorylase Activity and Enhancement of Capecitabine Efficacy by Taxol/Taxotere in Human Cancer Xenografts," *Clinical Cancer Res.* 4(4):1013-1019.
Scagliotti, G. V. et al. (Nov. 1, 2002). "Phase III Randomized Trial Comparing Three Platinum-Based Doublets in Advanced Non-Small-Cell Lung Cancer," *J. Clin. Oncol.* 20(21):4285-4291.
Scagliotti, G. V. et al. (Jul. 20, 2008, e-pub. May 27, 2008). "Phase III Study Comparing Cisplatin Plus Gemcitabine with Cisplatin Plus Pemetrexed in Chemotherapy-Naïve Patients with Advanced-Stage Non-Small-Cell Lung Cancer," *J. Clin. Oncol.* 26(21):3543-3551.
Schiller, J. H. et al., (Jan. 10, 2002). "Comparison of Four Chemotherapy Regimens for Advanced Non-Small-Cell Lung Cancer," *New England J. Med.* 346(2):92-98.
Schilsky, R. L. et al. (Jan. 15, 2002). "Dose-Escalating Study of Capecitabine Plus Gemcitabine Combination Therapy in Patients with Advanced Cancer," *J. Clin. Oncol.* 20(2):582-587.
Schnitzer, J. E. (Jan. 1992). "Gp60 is an Albumin-Binding Glycoprotein Expressed by Continuous Endothelium Involved in Albumin Transcytosis," *Am. J. Physiol.* 262(1, Pt. 2):H246-H254.
Schwonzen, M. et al. (Oct. 2000). "Liposomal Doxorubicin and Weekly Paclitaxel in the Treatment of Metastatic Breast Cancer," *Anti-Cancer Drugs* 11(9):681-685.
Seidman, A. D. et al. (1993). "Taxol Plus Recombinant Human Granulocyte-Colony Stimulating Factor as Initial and as Salvage Chemotherapy for Metastatic Breast Cancer: A Preliminary Report," *Monogr. Natl. Cancer Inst.* (15):171-175.
Shaked, Y. et al. (Jan. 2005). "Genetic Heterogeneity of the Vasculogenic Phenotype Parallels Angiogenesis: Implications for Cellular Surrogate Marker Analysis of Antiangiogenesis," *Cancer Cell* 7:101-111.
Shepherd, F. A. et al. (Dec. 1995). "Phase II Trials of Single-Agent Activity of Gemcitabine in Patients With Advanced Non-Small Cell Lung Cancer: An Overview," *Anti-Cancer Drugs* 6(Suppl. 6):19-25.
Shi, Q. et al. (Dec. 1997). "Antitumor Agents—CLXXV. Anti-Tubulin Action of (+)-Thiocolchicine Prepared by Partial Synthesis," *Bioorg. Med. Chem.* 5(12):2277-2282, Abstract only, located at http://www.ncib.nlm.nih.gov/pubmed/9459025, last visited on Jan. 11, 2010, one page.
Sledge, G. W. et al. (Feb. 15, 2003). "Phase III Trial of Doxorubicin, Paclitaxel, and the Combination of Doxorubicin and Paclitaxel as Front-line Chemotherapy for Metastatic Breast Cancer: an Intergroup Trial (E1193)," *J. Clin. Oncol.* 21(4):588-592.
Socinski, M. (Oct. 2006). "Update on Nanoparticle Albumin-Bound Paclitaxel," *Clinical Advances in Hematology & Oncology* 4(10):745-746.
Socinski, M. A. et al. (Aug. 1, 2009). "PD3.3.4—Retrospective Analysis of a Phase II Study of nab-Paclitaxel plus Carboplatin in Advanced NSCLC: Response Based on Histology," Abstract presented at the 13$^{th}$ World Conference on Lung Cancer, held in San Francisco, CA, on Jul. 31-Aug. 4, 2009, Abstract located at www.2009worldlungcancer.org, under *NSCLC—Advanced Disease I, organized by the International Association for the Study of Lung Cancer*, 2 pages (Abstract).
Socinski, M. A. et al. (Aug. 1, 2009). "PD3.3.4—Retrospective Analysis of a Phase II Study of nab-Paclitaxel plus Carboplatin in Advanced NSCLC: Response Based on Histology," Poster—Discussion presented as an Abstract at the 13$^{th}$ World Conference on Lung Cancer, held in San Francisco, CA, on Jul. 31-Aug. 4, 2009, under *NSCLC—Advanced Disease I, organized by the International Association for the Study of Lung Cancer*, 9 pages (Poster).
Socinski, M. A. et al. (Jun. 2010). "A Dose Finding Study of Weekly and Every-3-Week Nab-Paclitaxel Followed by Carboplatin as First-Line Therapy in Patients With Advanced Non-Small Cell Lung Cancer," *J. Thoracic Oncol.* 5(6):852-861.
Socinski, M. A. et al. (May 20, 2010). "Results of Randomized, Phase III Trial of Nab-Paclitaxel (Nab-P) and Carboplatin (C) Compared With Cremophor-Based Paclitaxel (P) and Carboplatin as First-Line Therapy in Advanced Non-Small Cell Lung Cancer (NSCLC)," Abstract from the 2010 ASCO Annual Meeting, under Abstract No. LBA 7511, published in *Supplement to J. Cin. Oncol.* 28(18S): Abstract No. LBA 7511, p. 541s, abstract also available at http://www.asco.org/ascov2/Meetings/Abstracts?&vmview=abst_detail_view&confID=74&abstractID=52889, last visited on Jul. 18, 2012, 4 pages.
Socinski, M. A. et al. (Published Ahead of Print on Apr. 30, 2012). "Weekly nab Paclitaxel in Combination With Carboplatin Versus Solvent-Based Paclitaxel Plus Carboplatin as First-Line Therapy in Patients With Advanced Non-Small-Lung Cancer: Final Results of a Final Phase III Trial," *J. Clin. Oncol.* 8 pages.
Sørensen, J. B. et al. (Mar. 1987). "Vinca Alkaloids in the Treatment of Non-Small Cell Lung Cancer," *Cancer Treatment Reviews* 14(1):29-51.

(56) References Cited

OTHER PUBLICATIONS

Sørensen, J. B. (Apr. 1995). "Gemcitabine in Non-Small Cell Lung Cancer," *Lung Cancer* 12(Suppl. 1):S173-S175.

Souquet, P. J. et al. (Jul. 3, 1993). "Polychemotherapy in Advanced Non Small Cell Lung Cancer: A Meta-Analysis," *Lancet* 342(8862):19-21.

Sparreboom, A. et al. (Apr. 1, 1999). "Cremophor EL-Mediated Alteration of Paclitaxel Distribution in Human Blood: Clinical Pharmacokinetic Implications," *Cancer Res.* 59(7):1454-1457.

Sparreboom, A. et al. (Jun. 1, 2005). "Comparative Preclinical and Clinical Pharmacokinetics of a Cremophor-Free, Nanoparticle Albumin-Bound Paclitaxel (ABI-007) and Paclitaxel Formulated in Cremophor (Taxol)," *Clin. Cancer Res.* 11(11):4136-4143.

Stinchcombe, T. E. et al. (2005). "Preliminary Results of Phase I Trial of Carboplatin (CP) in Combination with ABI-007 Administered Weekly or Every 3 Weeks in Patients (pts) With Solid Tumors," Abstract from the 28th *Annual San Antonio Breast Cancer Symposium*, held in San Antonio, Texas, USA, on Dec. 8-11, 2005, and published in *Breast Cancer Research and Treatment*, 94(1):571, Abstract No. 1092, one page.

Stinchcombe, T. E. et al. (Oct. 2007). "Phase I and Pharmacokinetic Trial of Carboplatin and Albumin-Bound Paclitaxel, ABI-007 (Abraxane®) on Three Treatment Schedules in Patients with Solid Tumors," *Cancer Chemotherap. Pharmacol.* 60(5):759-766.

Stroyakovsky, D. L. et al. (Aug. 1, 2009). "PD3.4.1—Weekly and Every-3-Week Nab-Paclitaxel Followed by Carboplatin as First-Line Therapy is Effective in Patients With Advanced Non-Small Cell Lung Cancer: Final Results of a Phase II Study," Abstract presented at the 13th *World Conference on Lung Cancer*, held in San Francisco, CA, on Jul. 31-Aug. 4, 2009, under NSCLC—Advanced Disease I, conference organized by the International Association for the Study of Lung Cancer, abstract located at www.2009worldlungcancer.org, http://abstracts/webges.com/itinerary/itinerary.php?i=1&abstract=2157&keyword=paclitaxel, last visited on Nov. 11, 2010, 2 pages (Abstract).

Stroyakovsky, D. L. et al. (2009). "PD3.4.1—Weekly and Every-3-Week nab—Paclitaxel Followed by Carboplatin as First-Line Therapy is Effective in Patients With Advanced Non-Small Cell Lung Cancer: Final Results of a Phase II Study," Poster-Discussion presented at the 13th *World Conference on Lung Cancer*, San Francisco, Ca, Jul. 31-Aug. 4, 2009, under NSCLC—Advanced Disease I, conference organized by the International Association for the Study of Lung Cancer, 10 pages (Poster).

Sugio, S. et al. (1999). "Crystal Structure of Human Serum Albumin at 2.5 Å Resolution," *Protein Eng.* 12(6):439-446.

Tahir, S. A. et al. (May 15, 2001). "Secreted Caveolin-1 Stimulates Cell Survival/Clonal Growth and Contributes to Metastasis in Androgen-Insensitive Prostate Cancer," *Cancer Res.* 61(10):3882-3885.

Tahir, S. A. et al. (Sep. 1, 2003). "Development of an Immunoassay for Serum Caveolin-1: A Novel Biomarker for Prostate Cancer," *Clin. Cancer Res.* 9(10 Pt. 1):3653-3659.

Tao, C. et al. (2005, e-pub: Sep. 23, 2003). "Preparation of Nanoparticle Albumin Bound 17AAG (nab-17AAG) Suitable for Intravenous Administration," *Proc. Amer. Assoc. Cancer Res.* vol. 46, Experimental and Molecular Therapeutics 10: Drug Targeting, Abstract No. 1435, located at http://www.aacrmeetingabstracts.org/cgi/content/abstract/2005/1/336-b, last visited on Jul. 18, 2012, two pages.

Tao, C. et al. (2006). "Preparation and Evaluation of Novel Derivatives of Geldanamycin," Abstract 1121, *Proc. Amer. Assoc. Cancer Res.* vol. 47, Chemistry 2: Drug Discovery 1: Screening, Synthesis, and Structure-Activity Relationships, Abstract No. 1121, located at http://www.aacrmeetingabstracts.org/cgi/content/abstract/2006/1/265, last visited on Jul. 22, 2009, two pages.

TARCEVA® (Erlotinib) Prescribing Product Label Information for Tablets, Oral Administration of TARCEVA® (revised as Apr. 2009). Initial U.S. Approval: 2004, Manufactured for: OSI Pharmaceuticals, Inc. Melville, NY 11747; Manufactured by Schwarz Pharma Manufacturing, Seymour, IN 47274; Distributed by Genentech USA, Inc. CA 94080-4990; Under Section 14 of "Clinical Studies", see specifically Sections Nos. 14.1 entitled "NSCLC—TARCEVA Administered Concurrently with Chemotherapy," and 14.2 entitled "Pancreatic Cancer—TARCEVA Administered Concurrently with Gemcitabine," 4 pages.

Ten Tije, A. J. et al. (2003). "Pharmacological Effects of Formulation Vehicles: Implications for Cancer Chemotherapy," *Clin. Pharmacokinet.* 42(7):665-685.

Therasse, P. et al. (Feb. 2, 2000). "New Guidelines to Evaluate the Response to Treatment in Solid Tumors. European Organization for Research and Treatment of Cancer, National Cancer Institute of the United States, National Cancer Institute of Canada," *J. Natl. Cancer Inst.* 92(3):205-216.

Trieu, V. et al. (Apr. 2008). "Cardiovascular and Respiratory Assessment Following IV Administration of Nanoparticle Albumin-Bound 17AAG (nab-17AAG) in Conscious Cynomolgus Monkeys" Abstract presented at the 99th *AACR Annual Meeting*, in San Diego, CA, on Apr. 12-16, 2008, Abstract located at http://www.aacrmeetingabstracts.org/cgi/content/meeting_abstract/2008/1_Annual_Meeting/5746?maxtoshow=&hits=10&RESULTFORMAT=&author1=trieu&andorexactfulltext=and&searchid=1&FIRSTINDEX=10&sortspec=relevance&resourcetype=HWCIT, Abstract No. 5746, 2 pages.

Trieu, V. et al. (2008). "Pharmacokinetic and ADME Study of Nanoparticle Albumin-Bound 17AAG (nab-17AAG) in Mice," Pharmacology: Nanoparticles and New Drug Delivery Strategies: Poster, Abstract No. 5747, presented at 99th *AACR Annual Meeting*, Apr. 12-16, 2008, San Diego, CA, located at http://www.aacrmeetingabstracts.org/cgi/content/meeting_abstract/2008/1_Annual_Meeting/5747, last visited on Jul. 22, 2009 two pages.

Tsai, J. Y. et al. (Aug. 2003). "Combined Modality Therapy for Pancreatic Cancer," *Seminars in Oncology* 30(4): Suppl. 9, pp. 71-79.

Tullis, J. L. (Jan. 24, 1977). "Albumin. 1. Background and Use," *JAMA* 237(4):355-360.

Tullis, J. L. (Jan. 31, 1977). "Albumin. 2. Guidelines for Clinical Use," JAMA 237(5):460-463.

Van Cutsem, E. et al. (Apr. 15, 2004). "Phase III Trial of Gemcitabine Plus Tipifarnib Compared With Gemcitabine Plus Placebo in Advanced Pancreatic Cancer," *J. Clin. Oncology* 22(8):1430-1438.

Vanderbilt-Ingram Cancer Centre (Aug. 11, 2009). "Paclitaxel Albumin-Stabilized Nanoparticle Formulation, Carboplatin, and Radiation Therapy in Treating Patients With Stage III Non-Small-Cell Lung Cancer That Cannot Be Removed by Surgery," Article located at http://clinicaltrials.gov/archive/NTC00544648/2009_08_11, ClinicalTrials.gov Identifier: NCT00544648, study first received on Oct. 13, 2007, last updated on May 3, 2011, with updates, last visited on Jul. 20, 2011, 16 pages.

Van Tellingen, O. et al. (Sep. 1999). "Cremophor EL Causes (Pseudo-) Non-Linear Pharmacokinetics of Paclitaxel in Patients," *Br. J. Cancer* 81(2):330-335.

Vogel, C. (Oct. 1, 2005). "Nab Paclitaxel," *Breast Cancer Update Nurses* 3(2): p. 12.

Von Hoff, D. D. et al. (2009). "SPARC Correlation with Response to Gemcitabine (G) Plus nab-Paclitaxel (nab-P) in Patients with Advanced Metastatic Pancreatic Cancer: A Phase I/II Study," Abstract presented at the 2009 *ASCO Annual Meeting*, in Orlando, Florida, on May 29-Jun. 2, 2009, Abstract published in *J. Clin. Oncol.* 27:15s, 2009 (Suppl: Abstract 4525), Abstract relocated at http://www.asco.org/ASCOv2/Meetings/Abstracts?&vmview=abst_detail_view&confID=65&abstractID=35160, last visited on Feb. 23, 2010, 3 pages (Abstract).

Von Hoff, D. D. et al. (2009). "SPARC Correlation with Response to Gemcitabine (G) Plus nab-Paclitaxel (nab-P) in Patients with Advanced Pancreatic Cancer," Poster-Discussion presented at the 2009 *ASCO Annual Meeting*, in Orlando, Florida, on May 29-Jun. 2, 2009, 13 pages (Poster).

Vorum, H. (Nov. 1999). "Reversible Ligand Binding to Human Serum Albumin," *Dan. Med. Bull.* 46(5):379-399.

Weiss, R. B. et al. (Jul. 1990). "Hypersensitivity Reactions from Taxol," *J. Clin. Oncol.* 8(7):1263-1268.

Welch, S. A. et al. (Jun. 1, 2007) "Combination Chemotherapy in Advanced Pancreatic Cancer: Time to Raise the White Flag?" *J. Clin. Oncol.* 25(16):2159-2161.

(56) References Cited

OTHER PUBLICATIONS

Willett, C. G. et al. (Dec. 2003). "Update on Combined-Modality Treatment Options for Pancreatic Cancer," *Oncology* 17(12): Suppl. 13, pp. 29-36.

Winer, E. et al. (1998). "Failure of Higher Dose Paclitaxel to Improve Outcome in Patients With Metastatic Breast Cancer—Results From CALGB 9342," Abstract presented at the 1998 ASCO Annual Meeting, Abstract located at http://www.asco.org/ascov2/Meetings/Abstracts?&vmview=abst_detail_view&confID=31&abstractID=12751, last visited on Jul. 18, 2012, Abstract No. 388, 3 pages.

Wozniak, A. J. et al. (Jul. 1998). "Randomized Trial Comparing Cisplatin with Cisplatin plus Vinorelbine in the Treatment of Advanced Non-Small-Cell Lung Cancer: A Southwest Oncology Group Study," *J. Clin. Oncol.* 16(7):2459-2465.

Yang, G. et al. (Aug. 1998). "Elevated Expression of Caveolin is Associated With Prostate and Breast Cancer," *Clin. Cancer Res.* 4(8):1873-1880.

Yoo, S.-H. et al. (2003). "Expression of Caveolin-1 is Associated with Poor Prognosis of Patients with Squamous Cell Carcinoma of the Lung," *Lung Cancer* 42:195-202.

Zalcberg, J. et al. (May 1998). "Phase II Study of Docetaxel and Cisplatin in Advanced Non-Small-Cell Lung Cancer," *J. Clin. Onc.* 16(5):1948-1953.

Zeinalova, K. P. et al. (2005). "Avastatin (Bevacizumab) in Treating Malignant Tumors: New Data," *Farmateka* 18(113):22-26, with English translation (14 pages).

International Search Report dated Jul. 7, 2006, for PCT Patent Application No. PCT/US2006/006167, filed on Feb. 21, 2006, published on Aug. 24, 2006, as WO 2006/089290, 4 pages.

Written Opinion dated Jul. 7, 2006 for PCT Patent Application No. PCT/US2006/006167, filed on Feb. 21, 2006, published on Aug. 24, 2006, as WO 2006/089290, 7 pages.

International Search Report dated Mar. 17, 2008, for PCT Patent Application No. PCT/US2007/023446, filed on Nov. 6, 2007, published on May 15, 2008, as WO 2008/057562, 3 pages.

Written Opinion dated Mar. 17, 2008, for PCT Patent Application No. PCT/US2007/023446, filed on Nov. 6, 2007, published on May 15, 2008, as WO 2008/057562, 6 pages.

European Search Report dated Jun. 29, 2011, for European Patent Application No. 10011106.1, filed on Feb. 21, 2006, 9 pages.

European Search Report dated Jul. 3, 2012, for European Patent Application No. 12154995.0, filed on Nov. 6, 2007, 6 pages.

International Search Report dated Jun. 6, 2011, for PCT Patent Application No. PCT/US2011/030209, filed on Mar. 28, 2011, published on Oct. 6, 2011, as WO 2011/123395, 6 pages.

Written Opinion dated Jun. 6, 2011, for PCT Patent Application No. PCT/US2011/030209, filed on Mar. 28, 2011, published on Oct. 6, 2011, as WO 2011/123395, 8 pages.

International Search Report dated May 30, 2011, for PCT Patent Application No. PCT/US2011/030206, filed on Mar. 28, 2011, published on Oct. 6, 2011, as WO 2011/123393, 5 pages.

Written Opinion dated May 30, 2011, for PCT Patent Application No. PCT/US2011/030206, filed on Mar. 28, 2011, published on Oct. 6, 2011, as WO 2011/123393, 6 pages.

U.S. Appl. No. 09/446,783, filed May 16, 2000, for Desai et al. (copy not attached).

U.S. Appl. No. 09/937,840, filed Jan. 28, 2002, for Desai et al. (copy not attached).

U.S. Appl. No. 12/479,710, filed Jun. 5, 2009 for Desai et al. (copy not attached).

U.S. Appl. No. 13/255,893, filed Mar. 12, 2010, for Desai et al. (copy not attached).

U.S. Appl. No. 13/263,723, filed Apr. 9, 2010, for Desai et al. (copy not attached).

U.S. Appl. No. 13/392,501, filed Aug. 25, 2010, for Tao et al. (copy not attached).

U.S. Appl. No. 13/368,297, filed Feb. 7, 2012, for Desai et al. (copy not attached).

U.S. Appl. No. 13/368,250, filed Feb. 7, 2012, for Desai et al. (copy not attached).

U.S. Appl. No. 13/408,994, filed Feb. 29, 2012, for De et al. (copy not attached).

U.S. Appl. No. 13/423,095, filed Mar. 16, 2012, for Desai et al. (copy not attached).

U.S. Appl. No. 13/649,987, filed Oct. 11, 2012, for Desai et al. (copy not attached.).

U.S. Appl. No. 13/777,980, filed Feb. 26, 2013, for Desai et al. (copy not attached.).

U.S. Appl. No. 13/777,988, filed Feb. 26, 2013, for Desai et al. (copy not attached.).

U.S. Appl. No. 13/564,633, filed Aug. 1, 2012, for Desai et al. (copy not attached.).

U.S. Appl. No. 13/585,696, filed Aug. 14, 2012, for Desai et al. (copy not attached.).

U.S. Appl. No. 13/743,212, filed Jan. 1, 2013, for Desai et al. (copy not attached.).

U.S. Appl. No. 13/776,481, filed Feb. 25, 2013, for Desai et al. (copy not attached.).

U.S. Appl. No. 13/776,484, filed Feb. 25, 2013, for Desai et al. (copy not attached.).

U.S. Appl. No. 13/779,625, filed Feb. 27, 2013, for Desai et al. (copy not attached.).

U.S. Appl. No. 13/779,624, filed Feb. 27, 2013, for Desai et al. (copy not attached.).

U.S. Appl. No. 13/779,621, filed Feb. 27, 2013, for Desai et al. (copy not attached.).

U.S. Appl. No. 13/781,482, filed Feb. 28, 2013, for Desai et al. (copy not attached.).

U.S. Appl. No. 13/781,479, filed Feb. 28, 2013, for Desai et al. (copy not attached.).

U.S. Appl. No. 13/781,489, filed Feb. 28, 2013, for Trieu et al. (copy not attached.).

U.S. Appl. No. 13/781,487, filed Feb. 28, 2013, for Tao et al. (copy not attached.).

U.S. Appl. No. 13/585,603, filed Mar. 25, 2011, for Yeo et al. (copy not attached.).

U.S. Appl. No. 13/781,480, filed Feb. 28, 2013, for Yeo et al. (copy not attached.).

U.S. Appl. No. 13/782,990, filed Mar. 1, 2013, for Desai et al. (copy not attached.).

U.S. Appl. No. 13/782,988, filed Mar. 1, 2013, for Desai et al. (copy not attached.).

U.S. Appl. No. 13/701,003, filed May 20, 2011, for Desai et al. (copy not attached.).

U.S. Appl. No. 13/782,984, filed Mar. 1, 2013, for Desai et al. (copy not attached.).

U.S. Appl. No. 13/701,002, filed May 20, 2011, for Desai et al. (copy not attached.).

U.S. Appl. No. 13/783,122, filed Mar. 1, 2013, for Desai et al. (copy not attached.).

U.S. Appl. No. 13/701,001, filed May 20, 2011, for Desai et al. (copy not attached.).

U.S. Appl. No. 13/782,992, filed Mar. 1, 2013, for Desai et al. (copy not attached.).

U.S. Appl. No. 13/794,705, filed Mar. 12, 2013, for Desai et al. (copy not attached.).

U.S. Appl. No. 13/791,841, filed Mar. 12, 2013, for Desai et al. (copy not attached.).

U.S. Appl. No. 13/794,480, filed Mar. 12, 2013, for Desai et al. (copy not attached.).

U.S. Appl. No. 13/794,486, filed Mar. 12, 2013, for Heise et al. (copy not attached.).

U.S. Appl. No. 13/794,712, filed Mar. 11, 2013, for Pierce et al. (copy not attached.).

Desai, N. et al. (Nov. 2006). "Enhanced Antitumor and Safety of Albumin-Bound Nab-Docetaxel Versus Polysorbate 80-Based Docetaxel," *EJC Supplements* 4(12):49, 18$^{th}$ Symposium on Molecular Targets and Cancer Therapeutics, Prague, Czech Republic, Nov. 7-10, 2006, 1 page.

Taxol® (2003). Taxol Prescribing Information (paclitaxel) Injection (Patent Information Included) Package Insert, pp. 1-53.

(56) References Cited

OTHER PUBLICATIONS

U.S. National Library of Medicine. "MedlinePlus® Lung Cancer—Non-Small Cell," located at <http://www.nlm.nih.gov/medlineplus/ency/article/007194.htm,> last visited on Aug. 29, 2013, 5 pages.

Apte, M.V. et al. (Oct. 2004). "Desmoplastic Reaction in Pancreatic Cancer: Role of Pancreatic Stellate Cells," Pancreas 29(3):179-187.

Belani, C. (Nov. 5-9, 2006). "Developments in the Treatment of Non-Small Cell Lung Cancer with Abraxane®," CancerConnect News, located at http://news.cancerconnect.com/developments-in-the-treatment-of-non-small-cell-lung-cancer-with-abraxane/, last visited Sep. 5, 2014, three pages.

Cho, D.S. et al. (2008). "Impact of Caveolin-1 Expression on the Prognosis of Transitional Cell Carcinoma of the Upper Urinary Tract," J. Korean Med. Sci. 23:296-301.

Halvorsen, T.B. et al. (1989). "Association Between Invasiveness, Inflammatory Reaction, Desmoplasia and Survival in Colorectal Cancer," J. Clin. Pathol. 42:162-166.

Mahadevan, D. et al. (Apr. 2007, e-pub. Apr. 3, 2007). "Tumor-stroma interactions in pancreatic ductal adenocarcinoma," Mol. Cancer Ther. 6(4):1186-1197.

Neesse, A. et al. (Jun. 2011, e-pub. Oct. 21, 2010). "Stromal Biology and Therapy in Pancreatic Cancer," Gut. 60(6):861-866.

Non-Final Office Action dated Feb. 13, 2014, for U.S. Appl. No. 13/781,479, filed Feb. 28, 2013, 39 pages.

Final Office Action dated May 20, 2014, for U.S. Appl. No. 13/073,824, filed Mar. 28, 2011, 11 pages.

Bertino, E.M. et al. (Oct. 30, 2014). "193-Phase II Trial of Nab-paclitaxel plus Carboplatin for Advanced NSCLC in Patients at Risk of Bleeding from VEGF Directed Therapies," presented at PV-Poster Viewing Session and Reception, as posted on http://www.abstractsonline.com, last visited on Feb. 12, 2015, two pages.

Chu, G.C. et al. (2007). "Stromal Biology of Pancreatic Cancer," Journal of Cellular Biochemistry 101-887-907.

Ito, T. et al. (2009). "Low Podoplanin Expression of Tumor Cells Predicts Poor Prognosis in Pathological Stage IB Squamous Cell Carcinoma of the Lung, Tissue Microarray Analysis of 136 Patients Using 24 Antibodies," Lung Cancer 63:418-424.

Korn E.L. et al. (2011). "Overall Survival as the Outcome for Randomized Clinical Trials With Effective Subsequent Therapies," J. Clin. Oncol. 29:2439-2442.

McKeage, M.J. et al. (2010). "Comparative Outcomes of Squamous and Non-squamous Non-small Cell Lung Cancer (NSCLC) Patients in Phase II Studies of ASA404 (DMXAA)—Retrospective Analysis of Pooled Data," J. Thorac. Dis. 2:199-204.

Muraoka N. et al. (2008). "Apparent Diffusion Coefficient in Pancreatic Cancer: Characterization and Histopathological Correlations," Journal of Magnetic Resonance Imaging 27:1302-1308.

National Cancer Institute. (Aug. 11, 2009). "A Phase I/II Study of Nab-Paclitaxel & Carboplatin with Concurrent Radiation Therapy for Unresectable Stage III Non-Small Cell Lung Cancer," Located at https://clinicaltrials.gov/archive/NCT00544648/2009_08_11, ClinicalTrials.gov Identifier: NCT00544648, last updated Aug. 11, 2009, last visited Jan. 22, 2015, 4 pages.

Nugent W.C. et al. (1997). "Non-Small Cell Lung Cancer at the Extremes of Age: Impact on Diagnosis and Treatment," Ann. Thorac. Surg. 63:193-7.

Socinski M.A. et al. (2013). "Safety and Efficacy of Weekly Nab®-paclitaxel in Combination with Carboplatin as First-line Therapy in Elderly Patients with Advanced Non-Small-Cell Lung Cancer," Annals of Oncology 24:314-321.

U.S. Department of Health and Human Services et al. (2011). "Guidance for Industry Clinical Trial Endpoints for the Approval of Non-Small Cell Lung Cancer Drugs and Biologics," located at http://www.fda.gov/Drugs/GuidanceComplianceRegulatoryInformation/Guidances/default.htm, 15 pages.

Non-Final Office Action dated Oct. 30, 2014, for U.S. Appl. No. 13/782,988, filed Mar. 1, 2013, 11 pages.

Non-Final Office Action dated Jan. 21, 2015, for U.S. Appl. No. 13/791,841, filed Mar. 8, 2013, 22 pages.

Non-Final Office Action dated Feb. 11, 2015, for U.S. Appl. No. 13/701,001, filed May 20, 2011, 15 pages.

Final Office Action dated Jun. 3, 2015, for U.S. Appl. No. 13/782,988, filed Mar. 1, 2013, 14 pages.

Final Office Action dated Jul. 10, 2015, for U.S. Appl. No. 13/263,723, filed May 4, 2012, 42 pages.

Ashcroft, T. et al. (1988). "Simple Method of Estimating Severity of Pulmonary Fibrosis on a Numerical Scale," J. Clin. Pathol. 41:467-470.

Bergamaschi, A. et al. (2008, e-pub. Nov. 29, 2007). "Extracellular Matrix Signature Identifies Breast Cancer Subgroups With Different Clinical Outcome," Journal of Pathology 214:357-367.

Bertino, E.M. et al. (2015). "Stomal Caveolin-1 is Associated With Response and Survival in a Phase II Trial of nab-Paclitaxel With Carboplatin for Advanced NSCLC Patients," Clinical Lung Cancer, pp. 1-9.

Farkas, L. et al. (May 2009). "VEGF Ameliorates Pulmonary Hypertension Through Inhibition of Endothelial Apoptosis in Experimental Lung Fibrosis in Rats," The Journal of Clinical Investigation 119(5):1298-1311.

Ferrini, F.S. et al. (2001). "Schirrous Invasive Ductal Carcinoma of the Breast Overexpress p53 Oncoprotein," Sao Paulo Medical Journal 119(1):4-6.

Oldberg, Å. et al. (Aug. 28, 2007). "Collagen-Binding Proteoglycan Fibromodulin Can Determine Stroma Matrix Structure and Fluid Balance in Experimental Carcinoma," Proc. Nat. Acad. Sci. USA 104(35):13966-13971.

U.S. Appl. No. 14/631,671, filed Feb. 25, 2015, by Desai et al. (Copy not attached).

U.S. Appl. No. 14/714,131, filed May 15, 2015, by Seward et al. (Copy not attached).

Arkhipova, K.A. et al. (2009). "Caveolin-1 Expression in Soft Tissue Tumors," Blokhina 20(1):4-9, found on Jul. 29, 2015 on the Web-site http://www.ronc.ru/attachments/article/1735/vestnikronic_1_2009.pdf . (English Abstract Only.).

Che, Y. et al. (2006). "The Differential Expression of SPARC in Esophageal Squamous Cell Carcinoma," International Journal of Molecular Medicine 17(6):1027-1033.

Goode, E.L et al. (2002). "Polymorphisms in DNA Repair Genes and Associations With Cancer Risk," Cancer Epidemiol. Biomarkers Prev. 11(12):1513-1530.

Khodyrev, D.S. et al. (2009). "Changes in Promoter Regions Methylation in Seven Human Chromosome 3 Genes in Epithelial Tumors," Moscow, p. 7 and 10 (Introduction Translated into English).

Lallemant, B. et al. (Oct. 18, 2009). "Clinical Relevance of Nine Transcriptional Molecular Markers of the Diagnosis of Head and Neck Squamous Cell Carcinoma in Tissue and Saliva Rinse," BMC Cancer 9(370):1-10.

Müller, B.G. et al. (1996). "Albumin Nanospheres as Carriers for Passive Drug Targeting: An Optimized Manufacturing Technique," Pharmaceutical Research 13(1):32-37.

Orlov, S.V. (2000). "Non-Small Cell Lung Cancer Symptoms, Diagnostics, and Staging," Medical Sciences 3:8-16, (English Translation).

Rempel, S.A. (Feb. 1999). "SPARC: A Potential Diagnostic Marker of Invasive Meningiomas," Clin. Cancer Res. 5:237-242.

Shigematsu, H. et al. (2006). "Somatic Mutations of Epidermal Growth Factor Receptor Signaling Pathway in Lung Cancers," International Journal of Cancer 118(2):257-262.

Smolyakovia, R.M. et al. (2003). "Clinicodiagnostic Significance of the Tests of Structural and Functional Properties of Serum Albmin in Small-Cell Lung Cancer Patients," Onkolog. J. Sibiri 4(12):12-16, (English Abstract Only).

Song, C.W. et al. (2006). "Influence of Tumor pH on Therapeutic Response," Chapter 2 in Cancer Drug Discovery and Development, Cancer Resistance, Teicher, B. ed., Humana Press, Inc., Totowa, NJ, pp. 21-45.

Tamboli, P. et al. (2006). "Pathological Evaluation of Lung Cancer," Chapter 4 in Lung Cancer MD Anderson Cancer Care Series, Fossella, A.F.V. et al. eds., pp. 36-37. (In Japanese with English Translation).

(56) References Cited

OTHER PUBLICATIONS

Woenchkhaus, M. et al. (May 2005). "Multitarget FISH and LOH analyses at chromosome 3p in non-small cell lung cancer and adjacent bronchial epithelium," *Am. J. Clin. Pathol.* 123(5):752-761.
Zhang, J. et al. (Jan. 2009). "Expression and Clinical Significance of SPARC in Clinical Stage II Tongue Squamous Cell Carcinoma," *Chinese Journal of Cancer* 28(1):68-71.
Non-Final Office Action dated Feb. 12, 2015, for U.S. Appl. No. 13/782,992, filed Mar. 1, 2013, 16 pages.
Non-Final Office Action dated Sep. 2, 2015, for U.S. Appl. No. 13/073,824, filed Mar. 28, 2011, 8 pages.
Non-Final Office Action dated Sep. 11, 2015, for U.S. Appl. No. 13/782,990, filed Mar. 2, 2013, 26 pages.
U.S. Appl. No. 14/834,331, filed Aug. 24, 2015, by Desai et al. (Copy not attached.).
U.S. Appl. No. 14/835,458, filed Aug. 25, 2015, by Desai et al. (Copy not attached.).
Final Office Action dated Aug. 12, 2016, for U.S. Appl. No. 13/782,988, filed Mar. 1, 2013, 17 pages.
Non-Final Office Action dated Apr. 10, 2017, for U.S. Appl. No. 15/364,189, filed Nov. 29, 2016, 30 pages.
U.S. Appl. No. 15/302,134, filed Apr. 3, 2015, for Desai et al. (Copy not attached).
U.S. Appl. No. 15/361,851, filed Nov. 28, 2016, for Desai et al. (Copy not attached).
U.S. Appl. No. 15/364,189, filed Nov. 29, 2016, for Desai et al. (Copy not attached).
U.S. Appl. No. 15/399,366, filed Jan. 5, 2017, for Pierce et al. (Copy not attached).
U.S. Appl. No. 15/412,897, filed Jan. 23, 2017, for Foss et al. (Copy not attached).
U.S. Appl. No. 15/462,361, filed Mar. 17, 2017, for Tao et al. (Copy not attached).
Abraxane®. (May 2009). Patient Information. Abraxane® for Injectable Suspension (Paclitaxel Protein-Bound Particles for Injectable Suspension)(albumin-bound), 22 pages.
Amatya, V.J. et al. (Jul. 2009). "Caveolin-1 is a Novel Immunohistochemical Marker to Differentiate Epithelioid Mesothelioma From Lung Adenocarcinoma," *Histopathology* 55(1):10-9. (Abstract Only, 2 pages).
Berenson, A. (Oct. 1, 2006). "Hope, at $4,200 a Dose," *The New York Times* 8 pages.
Business Wire. (Aug. 3, 2009). "Abraxis BioScience. Results From a Phase 2 Study of Abraxane® in Combination With Carboplatin Show Clinical Activity in the First Line Treatment of Patients With Advanced Non-Small Cell Lung Cancer. Randomized Pivotal Phase 3 Study Ongoing," *Business Wire*, 5 pages.
Cosaert, P. et al. (2002). "Platinum Drugs in the Treatment of Non-Small-Cell Lung Cancer," *British Journal of Cancer* 87:825-833.
Fu, Q. et al. (2009). "Nanoparticle Albumin—Bound (NAB) Technology is a Promising Method for Anti-Cancer Drug Delivery," *Recent Patents on Anti-Cancer Drug Discovery* 4:262-272.
Gen News. (Mar. 17, 2010). "Abraxis Says NSCLC Phase III Trial Met Its Primary Endpoint," *GEN News Highlights*, 3 pages.
Gradishar, WJ. (2006). "Albumin-Bound Paclitaxel: A Next-Generation Taxane," *Drug Evaluation* 7(8):1041-1053.
Heighway, J. et al (Feb. 2004). "Lung Tumours: An Overview," *Atlas Genetetics Cytogenetics in Oncology Haematology* 8(2):139-141.
Ho, J.C.M. (Dec. 2008). "The State-of-the-Art Treatment of Non-Small Cell Lung Cancer," *The Hong Kong Medical Diary* 13(12):13-15.
Iranzo, V. et al. (2009). "Induction Chemotherapy Followed by Concurrent Chemoradiation for Patients With Nonoperable Stage III Non-Small-Cell Lung Cancer," *Lung Cancer* 63:63-67.
Kosmidis, P. et al. (2000). Paclitaxel (175 mg/m$^2$) Plus Carboplatin (6 AUC) Versus Paclitaxel (225 mg/m$^2$) Plus Carboplatin (6 AUC) in Advanced Non-Small-Cell Lung Cancer (NSCLC): A Multicenter Randomized Trial, *Annals of Oncology* 11:799-805.
Krishnaveni, J. et al. (2016). "Evolution of Controlled drug Delivery System," Chapter 15 in *Drug Delivery: Principles and Application*, Wang, B. et al. eds., John Wiley & Sons, Hoboken, NJ, p. 346.
Mito, K. et al. (Oct. 2009). "Clinical Investigation of Weekly Carboplatin and Paclitaxedl With Concurrent Radiation Therapy for Locally Advanced Non-Small Lung Cancer," *Jpn. J. Cancer Chemother.* 36(10):1653-1656. (Translation of the Abstract Only).
Nice Guidlines. (Feb. 2005). "Lung Cancer. The Diagnosis and Treatment of Lung Cancer," *NHA NICE Guidelines* 24 pp. 1-41.
Socinski, M.A. et al. (Sep. 2009). "Retrospective Analysis of a Phase II Study of nab-Paclitaxel Plus Carboplatin in Advanced NSCLS: A Response based on Histology," *Journal of Thoracic Oncology* 4(9)(Supp. 1)(PD3.3.4):S449.
Extended European Search Report dated Feb. 15, 2017, for European Patent Application No. 16180384.6, filed on Jul. 20, 2016, 14 pages.
Communication of a Notice of Opposition for European Patent Application No. 11763292.7, dated Jun. 14, 2017, filed on Mar. 28, 2011, 18 pages.
Communication of a Notice of Opposition for European Patent Application No. 11763292.7, dated Jun. 16, 2017, filed on Mar. 28, 2011, 23 pages.
Non-Final Office Action dated Dec. 5, 2017, for U.S. Appl. No. 15/183,636, filed Jun. 15, 2016, 31 pages.
U.S. Appl. No. 15/663,351, filed Jul. 28, 2017, for Desai et al. (Copy not attached).
U.S. Appl. No. 15/669,821, filed Aug. 4, 2017, for Desai et al. (Copy not attached).
U.S. Appl. No. 15/555,310, filed Mar. 4, 2016, for Pierce et al. (Copy not attached).
U.S. Appl. No. 15/787,586, filed Oct. 18, 2017, for Desai et al. (Copy not attached).
U.S. Appl. No. 15/796,578, filed Oct. 27, 2017, for Desai et al. (Copy not attached).
U.S. Appl. No. 15/820,022, filed Nov. 21, 2017, for Desai et al. (Copy not attached).
Amatya, V.J. (Oct. 5, 2008). "Caveolin-1, a Novel Marker, Differentiates Epithelioid Mesothelioma From Lung Adenocarcinoma," *Japanese Journal of Lung Cancer* 49(5):469, Abstract 0-97, one page.
Amatya, V.J. (2008). "CD26 and Caveolin-1 Expression in Malignant Mesothelioma and Lung Adenocarcinoma," *Proceedings of the Japanese Society of Pathology* 97(1):379, Abstract No. P3-146, one page.
European Patent Office Board of Appeal. Mailed on Feb. 1, 2017, for Application No. 00922102.9, Datasheet for the Decision, 42 Pages.
Morton, R.F. et al (1991). "Thoracic Radiation Therapy Alone Compared With Combined Chemoradiotherapy for Locally Unresectable Non-Small Cell Lung Cancer. A Randomized, Phase III Trial," *Annals of Internal Medicine* 115(9):681-686.
Communication from Elkington & Fife for European Patent No. 2 552 415, Application No. 11763292.7, Opponent: Generics [UK] Ltd, 9 pages.
Non-Final Office Action dated Dec. 26, 2017, for U.S. Appl. No. 15/586,056, filed May 3, 2017, 18 pages.
U.S. Appl. No. 15/738,087, filed Jun. 29, 2016, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 15/737,936, filed Jun. 29, 2016, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 15/738,090, filed Jun. 29, 2016, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 15/737,943, filed Jun. 29, 2016, for Desai et al. (U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

U.S. Appl. No. 15/851,478, filed Dec. 21, 2017, for Seward et al. (U.S. Patent Application is not submitted herewith pursuant to the waiver of 37 C.F.R. § 1.98(a)(2)(iii) issued by the Office on Sep. 21, 2004.).
U.S. Appl. No. 15/879,320, filed Jan. 24, 2018, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 15/982,702, filed Mar. 22, 2018, for Peykov et al. (U.S. Patent Application is not submitted herewith pursuant to the waiver of 37 C.F.R. § 1.98(a)(2)(iii) issued by the Office on Sep. 21, 2004.).
Clinical Trials.gov. (Nov. 2007, Actual Completion Date Feb. 2013). "Albumin-Bound Paclitaxel (Abi-007) for Patients With Advanced Non-Small Lung Cancer," Located at https://clinicaltrialsl.gov/ct2/show/recordnnct00540514?sect-x0156, Last Visited on Aug. 1, 2018, 12 Pages.
Expert Declaration of Dr. Rafia Bhore From Opposition to European Patent Application No. 2 552 415 B1, Jul. 2, 2018, 21 Pages.
Final Office Action dated May 31, 2018, for U.S. Appl. No. 15/183,636, filed Jun. 15, 2016, 37 pages.
Further Submissions from Elkington & Fife for European Patent No. 2 552 415, Application No. 11763292.7, dated Aug. 20, 2018, Opponent: Generics [Uk} Ltd. 5 pages.
Mukherjee, S. (Nov. 28, 2017). "A Failure to Heal," The New York Times Magazine, 5 Pages.
Provision of the Minutes in Accordance With Rule 124(4) EPC, for European Patent Application No. 16180384.6, mailed on Oct. 4, 2018, 7 pages.
Submission Pursuant to Rule 116 EPC—mailed on Jul. 3, 2018, for Oral Proceedings on Sep. 3 and 4, 2018, for European Opposition for European Patent Application No. 2552415, 10 pages.
Supplemental Expert Declaration of Dr. Rafia Bhore From Opposition to European Patent Application No. 2 552 415B1, Aug. 29, 2018, 3 pages.
U.S. Appl. No. 16/101,027, filed Aug. 10, 2018, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 16/107,419, filed on Aug. 21, 2018, for Foss et al. (U.S. Patent Application is not submitted herewith pursuant to the waiver of 37 C.F.R. § 1.98(a)(2)(iii) issued by the Office on Sep. 21, 2004.).
U.S. Appl. No. 16/140,339, filed Sep. 24, 2018, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 16/170,522, filed Oct. 25, 2018, for Desai et al. (U.S. Patent Application is not submitted herewith pursuant to the waiver of 37 C.F.R. § 1.98(a)(2)(iii) issued by the Office on Sep. 21, 2004.).
Vorobiof, B.L. et al. (2002). "Malignant Pleural Mesothelioma: A Phase II Trial with Docetaxel," Annals of Oncology 13:412-415.
Communication pursuant to Article 94(3) EPC, mailed on Dec. 13, 2018, for European Patent Application No. 11763290.1, filed on Oct. 29, 2012, 6 pages.
Eltabbakh, G.H. et al. (1999). "Clinical Picture, Response to Therapy, and Survival of Women With Diffuse Malignant Peritoneal Mesothelioma," Journal of Surgical Oncology 70:6-12.
Tai, I.T. et al. (Jun. 2005). "Genome-Wide Expression Analysis of Therapy-Resistant Tumors Reveals SPARC as a Novel Target for Cancer Therapy," The Journal of Clinical Investigation 115(6):1492-1502.
Matsumoto, K. et al. (2008). "A Case of Diffuse Malignant Peritoneal Mesothelioma Successfully Treated With Neekly Paclitaxel," Journal of Japanese Society of Gastroenterology 105(Suppl-2.2):A923, Abstract No. Gast P-743, 4 pages with English Translation.
Ogura, O. et al. (Jul. 2006). "A Case of Malignant Peritoneal Mesothelioma Successfully Treated With Carboplatin and Paclitaxel," Jpn. J. Cancer Chemother. 33(7):1001-1004 (with English Translation).

\* cited by examiner

METHODS OF ENHANCING DRUG DELIVERY AND EFFECTIVENESS OF THERAPEUTIC AGENTS

RELATED APPLICATIONS

This application claims priority benefit to U.S. Provisional Patent Application No. 61/318,777, filed on Mar. 29, 2010, incorporated herein by reference in its entirety.

TECHNICAL FIELD

The present invention relates to methods of enhancing drug delivery and effectiveness of therapeutic agent(s) by administering compositions comprising nanoparticles that comprise albumin and a poorly water insoluble drug such as a taxane.

BACKGROUND

Taxanes (such as paclitaxel and docetaxel) are a class of diterpenoid drugs that have anti-tumor activity against a wide range of human cancers. Paclitaxel was originally isolated from the bark of the Yew tree, and was known to act by interfering with the normal function of microtubule breakdown. Paclitaxel binds to the β subunit of tubulin, the building blocks of microtubules, causing hyper-stabilization of the microtubule structures. The resulting paclitaxel/microtubule structure is unable to disassemble, thereby arresting mitosis and inhibiting angiogenesis.

Albumin-based nanoparticle compositions have been developed as a drug delivery system for delivering substantially water insoluble drugs such as a taxanes. See, for example, U.S. Pat. Nos. 5,916,596; 6,506,405; 6,749,868, and 6,537,579 and also in U.S. Pat. Pub. Nos. 2005/0004002 and 2007/0082838. The albumin-based nanoparticle technology utilizes the natural properties of the protein albumin to transport and deliver substantially water insoluble drugs to the site of disease. These drug-containing nanoparticles are readily incorporated into the body's own transport processes and are able to exploit the tumors' attraction to albumin, enabling the delivery of higher concentrations of the active drug in the nanoparticles to the target site. In addition, the albumin-based nanoparticle technology offers the ability to improve a drug's solubility by avoiding the need for toxic chemicals, such as solvents, in the administration process, thus potentially improving safety through the elimination of solvent-related side effects.

Therapeutic agents, especially cancer drugs, often suffer in overall effectiveness due to problems associated with delivery/access to target tumor sites. There is a need to improve effectiveness of therapeutic agents, especially those used in cancer therapy.

The disclosures of all publications, patents, patent applications and published patent applications referred to herein are hereby incorporated herein by reference in their entirety. The present application also incorporates U.S. Provisional Patent Application Nos. 61/318,774 and 61/433,132 by reference in their entirety.

BRIEF SUMMARY OF THE INVENTION

The present invention in one aspect provides methods of enhancing uptake of a therapeutic agent in a target tissue as well as methods of treating a disease (such as cancer) or enhancing effectiveness of treatment with a therapeutic agent in an individual by co-administering a composition comprising nanoparticles comprising albumin and a poorly water insoluble drug. Although the description below is specific to compositions comprising nanoparticles comprising albumin and a taxane (also referred to as a "taxane nanoparticle composition"), it is understood that the same applies to other drugs, such as rapamycin.

In some embodiments, there is provided a method of treating a disease (such as cancer) in an individual, comprising administering to the individual an effective amount of a therapeutic agent and a composition comprising nanoparticles comprising albumin and a taxane, wherein the uptake of the therapeutic agent to a target tissue (such as tumor) is enhanced compared to the uptake of the therapeutic agent not co-administered with the taxane nanoparticle composition.

In some embodiments, there is provided a method of treating an individual having a tumor (such as solid tumor), comprising administering to the individual an effective amount of a therapeutic agent and a composition comprising nanoparticles comprising albumin and a taxane, wherein the uptake of the therapeutic agent to the tumor is enhanced compared to the uptake of the therapeutic agent not co-administered with the taxane nanoparticle composition.

In some embodiments, there is provided a method of facilitating the uptake of a therapeutic agent to a target tissue (such as tumor) in an individual, comprising administering to the individual the therapeutic agent in conjunction with a composition comprising nanoparticles comprising an albumin and a taxane. In some embodiments, there is provided a method of facilitating the uptake of a therapeutic agent to a tumor (such as solid tumor) in an individual, comprising administering to the individual the therapeutic agent in conjunction with a composition comprising nanoparticles comprising an albumin and a taxane.

In some embodiments, there is provided a method of enhancing effectiveness of a therapeutic agent for treating a disease in an individual, comprising administering to said individual an effective amount of the therapeutic agent in conjunction with a composition comprising nanoparticles comprising an albumin and a taxane.

Also provided herein are methods of creating a microenvironment in a target tissue (such as tumor) in an individual that facilitates delivery of other therapeutic agent(s), i.e., therapeutic agent other than the drug in the nanoparticle composition. For example, in some embodiments, there is provided a method of altering the microenvironment of a target tissue (such as tumor) to facilitate uptake of a therapeutic agent, comprising administering to the individual a composition comprising nanoparticles comprising albumin and a taxane. In some embodiments, there is provided a method of reducing (such as disrupting, for example depleting) tumor stroma in an individual having a tumor, comprising administering to the individual a composition comprising nanoparticles comprising albumin and a taxane. In some embodiments, there is provided a method of increasing tumor vascularization in an individual having a tumor, comprising administering to the individual a composition comprising nanoparticles comprising albumin and a taxane. In some embodiments, there is provided a method of increasing cell/vessel proximity in an individual having a tumor, comprising administering to the individual a composition comprising nanoparticles comprising albumin and a taxane. In some embodiments, there is provided a method of loosening (such as disrupting, for example destroying) the tumor matrix in an individual having a tumor, comprising administering to the individual a composition comprising nanoparticles comprising albumin and a taxane.

The methods described herein can be practiced in conjunction with the administration of other therapeutic agent(s). For example, the method can be practiced in conjunction with the administration of at least one, including for example 2, 3, 4, or 5 other therapeutic agents (such as chemotherapeutic agents).

In some embodiments, the disease is cancer. In some embodiments, the cancer is any of pancreatic cancer, lung cancer (such as NSCLC), melanoma, or prostate cancer. In some embodiments, the cancer is squamous cell carcinoma, such as squamous NSCLC. In some embodiments, the cancer is advanced cancer, such as advanced pancreatic cancer or advanced NSCLC. In some embodiments, the cancer is highly fibrotic and/or has dense stroma. In some embodiments, the disease is not responsive to the treatment of the taxane nanoparticle composition when administered alone. In some embodiments, the amount of the taxane in the taxane nanoparticle composition is not effective for treating the disease when administered alone.

In some embodiments, the target tissue is a site of inflammation. In some embodiments, the target tissue is a site of tissue remodeling. In some embodiments, the target tissue is a site of wound healing.

In some embodiments, the target tissue has low vascularity. In some embodiments, the target tissue is hyper-fibrotic. In some embodiments, the target tissue has a dense stroma. In some embodiments, the target tissue is difficult to penetrate by therapeutic agents.

In some embodiments, the target tissue in the individual has a drug uptake capability. In some embodiments, the target tissue in the individual has a high level of albumin uptake. In some embodiments, the target tissue in the individual has a high level of Caveolin-1, gp60, and/or SPARC expression.

In another aspect, there is provided a method of treatment or a method of selecting patients for treatment with the combination of a therapeutic agent and a composition comprising nanoparticles comprising albumin and a taxane based on drug uptake capability.

In some embodiments, there is provided a method of treating a disease (such as cancer) in an individual, comprising administering to the individual: (a) an effective amount of a composition comprising nanoparticles comprising albumin and a taxane, and (b) an effective amount of a therapeutic agent, wherein drug uptake capability is used as a basis for selecting the individual to receive treatment.

In some embodiments, there is provided a method of treating a disease (such as cancer) in an individual, comprising: (a) determining the drug uptake capability of the target tissue in the individual, and (b) administering to the individual: (1) an effective amount of a composition comprising nanoparticles comprising albumin and a taxane, and (2) a therapeutic agent. In some embodiments, the method further comprises isolating a tissue sample from said individual, for example for the purpose of determining drug uptake capability.

In some embodiments, there is provided a method of identifying an individual suitable for treatment comprising administering (a) an effective amount of a composition comprising nanoparticles comprising albumin and a taxane, and (b) an effective amount of a therapeutic agent, wherein the individual is identified as being suitable for treatment if the individual has a drug uptake capability in the target tissue. In some embodiments, the method further comprises determining the drug uptake capability of the target tissue in the individual, for example for the purpose of determining drug uptake capability. In some embodiments, the method further comprises isolating a tissue sample from said individual. In some embodiments, the method further comprises administering the effective amount of a composition comprising nanoparticles comprising albumin and a taxane and a therapeutic agent to the individual.

In some embodiments, there is provided a method of assessing responsiveness of an individual to a treatment method comprising administration of (a) an effective amount of a composition comprising nanoparticles comprising albumin and a taxane and (b) an effective amount of a therapeutic agent, the method comprising determining drug uptake capability of the target tissue in the individual, wherein a drug uptake capability is indicative that the individual is responsive to the treatment. In some embodiments, the method further comprises determining the drug uptake capability of the target tissue in the individual. In some embodiments, the method further comprises isolating a tissue sample from said individual, for example for the purpose of determining drug uptake capability. In some embodiments, the method further comprises administering the effective amount of a composition comprising nanoparticles comprising albumin and a taxane and a therapeutic agent to the individual who is determined to be responsive to the treatment.

Drug uptake capability can be determined, for example, based on the level of albumin uptake in the target tissue, level of caveolin-1 in the target tissue, level of gp60 in the target tissue, and/or level of SPARC in the target tissue. For example, in some embodiments, a target tissue is considered as having a drug uptake capability if it shows one or more of the following characteristics: 1) increased albumin uptake; 2) increased caveolin-1 expression; 3) increased gp60 expression; and 4) increased SPARC expression.

Also provided are methods of screening for an individual for a combination therapy treatment described herein, methods of determining whether an individual is unsuitable for a combination therapy treatment described herein, methods of determining whether an individual is suitably treated with combination therapy described herein, and methods of monitoring combination therapy treatment in an individual described herein.

Further provided are kits and articles of manufacture that are useful for methods described herein, as well as marketing methods described herein.

DETAILED DESCRIPTION OF THE INVENTION

The present invention provides methods of enhancing delivery of therapeutic agents to target tissues by co-administering a composition comprising nanoparticles comprising albumin and a poorly water soluble drug such as a taxane, as well as methods of identifying individuals who are suitable for or responsive to the combination therapy based on one or more characteristics of the target tissue that correlates or indicates the capability of getting enhanced therapeutic agent uptake as a result of the co-administration of the nanoparticle composition (such as a taxane nanoparticle composition) in the target tissue.

The effectiveness of the therapeutic agent is enhanced via this enhanced access/delivery facilitated and mediated by the nanoparticle composition. This discovery is striking because these treatment schemes are expected to significantly advance the effectiveness not only of standard therapies for a number of cancers, including difficult-to-treat cancers, but also raise the possibility that other prior unsuccessful and unapproved therapeutic regimes will be advanced.

A composition comprising nanoparticles comprising albumin and a taxane, namely, Abraxane®, has shown substantially improved therapeutic efficacies in various clinical trials when combined with a variety of therapeutic agents in treating various tumors. For example, in a randomized Phase 3 clinical trial in combination with carboplatin for treating advanced non-small cell lung cancer (NSCLC), Abraxane® has shown a significant improvement in overall response rate as compared to Taxol®. Abraxane® has also shown remarkable results in treating pancreatic cancer when combined with gemcitabine. Furthermore, a composition comprising nanoparticles comprising albumin and docetaxel, namely, Nab-docetaxel, was shown to enhance the effectiveness of prednisone in treating prostate cancer.

We hypothesize that a composition comprising nanoparticles comprising albumin and a poorly water insoluble drug (such as a taxane) changes the tumor microenvironment (for example by destroying the tumor stroma, increasing vascularization in the tumor, and/or increasing cell/vessel proximity) and makes tumor cells more accessible to other therapeutic agent(s), thus facilitating tumor uptake of therapeutic agent(s). The nanoparticle drug composition thus creates a portal or breach in the tissue microenvironment that results in increased delivery of the drug in the nanoparticle as well as other drugs to the target tissue. This is supported, for example, by our studies on the combination of gemcitabine and Abraxane® in a pancreatic tumor xenograft model, where we demonstrated that Abraxane® effectively destroys pancreatic cancer stroma and substantially increases the tumoral delivery of gemcitabine.

Accordingly, the present invention in one aspect provides methods of enhancing uptake of a therapeutic agent in a target tissue as well as methods of treating a disease (such as cancer) or enhancing effectiveness of treatment with a therapeutic agent in an individual by co-administering a composition comprising nanoparticles comprising albumin and a poorly water insoluble drug (such as a taxane) with the therapeutic agent.

In another aspect, there is provided a method of treatment or a method of selecting patients for treatment with the combination of a therapeutic agent and a composition comprising nanoparticles comprising albumin and a poorly water insoluble drug (such as a taxane) based on one or more characteristics of the target tissue that correlates or indicates the capability of getting enhanced therapeutic agent uptake as a result of the co-administration of the nanoparticle composition in the target tissue (referred to as "the drug uptake capability").

Also provided are pharmaceutical compositions, article of manufacture, and kits useful for methods described herein.

Although the description below is specific to a taxane nanoparticle composition, it is understood that the same applies to nanoparticle compositions of other drugs, such as rapamycin.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of a disease. The methods of the invention contemplate any one or more of these aspects of treatment.

The term "individual" refers to a mammal and includes, but is not limited to, human, bovine, horse, feline, canine, rodent, or primate. In some embodiments, the individual is human.

As used herein, by "combination therapy" or "co-administration" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual.

The term "effective amount" used herein in the context of treatment refers to an amount of a compound or composition sufficient to treat a specified disorder, condition or disease such as ameliorate, palliate, lessen, and/or delay one or more of its symptoms. In the context of enhancing delivery, access, and other effectiveness aspects facilitated/mediated by the albumin-based nanoparticle compositions, effective amount refers to amount sufficient to obtain these goals, such as an amount effective to increase access of the therapeutic agent to a target tissue.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

A composition is "in an amount that is insufficient to induce significant cytotoxicity" (also referred to as "noncytotoxic amount") if the amount of the composition is insufficient to cause significant cell death in an individual.

"Subtherapeutic amount" or "subtherapeutic level" of a drug refer to an amount that is less than the therapeutic amount, that is, less than the amount normally used when the drug is administered alone. The reduction may be reflected in terms of the amount administered at a given administration and/or the amount administered over a given period of time (reduced frequency).

"Drug uptake capability" of a target tissue used herein refers to the capability of getting enhanced therapeutic agent uptake by a composition comprising nanoparticles comprising albumin and a taxane in the target tissue.

When drug uptake capability "is used as a basis" for the treatment methods described herein, or selection for the treatment methods described herein, drug uptake capability is measured before and/or during treatment, and the information obtained is used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits. As would be well understood by one in the art, measurement of drug uptake capability in a clinical setting is a clear indication that this parameter is used as a basis for initiating, continuing, adjusting and/or ceasing administration of the treatments described herein.

A drug uptake capability measured "before or upon initiation of treatment" is drug uptake capability measured in an individual before the individual receives the first administration of a treatment modality described herein and/or within at least about 4 weeks, preferably within at least about 2 weeks, preferably within at least about 1 week, preferably within at least about 5 days, preferably within at least about 3 days, preferably within at least about 2 days, preferably within at least about 1 day upon receiving the first administration of a treatment modality described herein.

An individual who "may be suitable", which includes an individual who is "suitable" for treatment(s) described herein, is an individual who is more likely than not to benefit from administration of said treatments. Conversely, an individual who "may not be suitable" or "may be unsuitable", which includes an individual who is "unsuitable" for treatment(s) described herein, is an individual who is more likely than not to fail to benefit from administration of said treatments.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

Methods of Treatment and Enhancing Drug Uptake

The present invention provides methods of co-administering a therapeutic agent and a composition comprising nanoparticles comprising albumin and a taxane. The taxane nanoparticle composition creates a favorable microenvironment in the target tissue (such as tumor) that makes the target tissue more accessible to the therapeutic agent.

Thus, in some embodiments, there is provided a method of treating a disease (such as cancer) in an individual, comprising administering to the individual an effective amount of a therapeutic agent and a composition comprising nanoparticles comprising albumin and a taxane, wherein the uptake of the therapeutic agent to a target tissue (such as tumor) is enhanced compared to the uptake of the therapeutic agent not co-administered with the taxane nanoparticle composition. In some embodiments, there is provided a method of treating an individual having a tumor (such as solid tumor), comprising administering to the individual an effective amount of a therapeutic agent and a composition comprising nanoparticles comprising albumin and a taxane, wherein the uptake of the therapeutic agent to the tumor is enhanced compared to the uptake of the therapeutic agent not co-administered with the taxane nanoparticle composition. In some embodiments, the average particle size of the nanoparticle composition is no greater than about 200 nm. In some embodiments, the taxane nanoparticle composition is administered weekly. In some embodiments, the taxane nanoparticle composition is administered intravenously. In some embodiments, the taxane nanoparticle composition is intravenously administered weekly.

Thus, in some embodiments, there is provided a method of treating a disease (such as cancer) in an individual, comprising administering to the individual an effective amount of a therapeutic agent and a composition comprising nanoparticles comprising albumin and a taxane, wherein the taxane in the nanoparticles is coated with albumin, wherein the uptake of the therapeutic agent to a target tissue (such as tumor for example solid tumor) is enhanced compared to the uptake of the therapeutic agent not co-administered with the taxane nanoparticle composition. In some embodiments, there is provided a method of treating a disease (such as cancer) in an individual, comprising administering to the individual an effective amount of a therapeutic agent and a composition comprising nanoparticles comprising albumin and a taxane, wherein the average particle size of the nanoparticle composition is no greater than about 200 nm, wherein the uptake of the therapeutic agent to a target tissue (such as tumor for example solid tumor) is enhanced compared to the uptake of the therapeutic agent not co-administered with the taxane nanoparticle composition. In some embodiments, there is provided a method of treating a disease (such as cancer) in an individual, comprising administering to the individual an effective amount of a therapeutic agent and a composition comprising nanoparticles comprising albumin and a taxane, wherein the taxane in the nanoparticles is coated with albumin, wherein the average particle size of the nanoparticle composition is no greater than about 200 nm, and wherein the uptake of the therapeutic agent to a target tissue (such as tumor for example solid tumor) is enhanced compared to the uptake of the therapeutic agent not co-administered with the taxane nanoparticle composition. In some embodiments, the taxane nanoparticle composition is administered weekly. In some embodiments, the taxane nanoparticle composition is administered intravenously. In some embodiments, the taxane nanoparticle composition is intravenously administered weekly.

In some embodiments, there is provided a method of treating a disease (such as cancer) in an individual, comprising administering to the individual an effective amount of a therapeutic agent and Nab-paclitaxel (Abraxane®)), wherein the uptake of the therapeutic agent to a target tissue (such as tumor) is enhanced compared to the uptake of the therapeutic agent not co-administered with the taxane nanoparticle composition. In some embodiments, there is provided a method of treating an individual having a tumor (such as solid tumor), comprising administering to the individual an effective amount of a therapeutic agent and Nab-paclitaxel (Abraxane®), wherein the uptake of the therapeutic agent to the tumor is enhanced compared to the uptake of the therapeutic agent not co-administered with the taxane nanoparticle composition. In some embodiments, the Nab-paclitaxel (Abraxane®) is administered weekly. In some embodiments, the Nab-paclitaxel (Abraxane®) is administered intravenously. In some embodiments, the Nab-paclitaxel (Abraxane®) is intravenously administered weekly.

In some embodiments, there is provided a method of facilitating the uptake of a therapeutic agent to a target tissue (such as tumor) in an individual, comprising administering to the individual the therapeutic agent in conjunction with a composition comprising nanoparticles comprising an albumin and a taxane. In some embodiments, there is provided a method of facilitating the uptake of a therapeutic agent to a tumor (such as solid tumor) in an individual, comprising administering to the individual the therapeutic agent in conjunction with a composition comprising nanoparticles comprising an albumin and a taxane. In some embodiments, the taxane nanoparticle composition is administered weekly. In some embodiments, the taxane nanoparticle composition is administered intravenously. In some embodiments, the taxane nanoparticle composition is intravenously administered weekly.

In some embodiments, the method further comprises a step of determining tissue uptake of the therapeutic agent when administered alone to an individual for the purpose of determining whether the individual is suitable for (or in need of) the combination of the therapeutic agent and the taxane nanoparticle composition. A low tissue uptake of the therapeutic agent when administered alone would indicate that this individual would be suitable for (or in need of) the combination of the therapeutic agent and the taxane nanoparticle composition. Thus, for example, in some embodiments, there is provided a method of facilitating the uptake a therapeutic agent to a target tissue (such as tumor, for example solid tumor) in an individual, comprising: a) administering the therapeutic agent to the individual and determining tissue uptake of the therapeutic agent; and 2) administering to the individual the therapeutic agent in conjunction with a composition comprising nanoparticles comprising an albumin and a taxane. In some embodiments, there is provided a method of facilitating the uptake a therapeutic agent to a target tissue (such as tumor, for example solid tumor) in an individual, comprising: a) administering the therapeutic agent to the individual and determining tissue uptake of the therapeutic agent; and 2) administering to the individual the therapeutic agent in conjunction with a composition comprising nanoparticles comprising an albumin and a taxane, wherein the taxane in the nanoparticles is coated with albumin. In some embodiments, there is provided a method of facilitating the uptake a therapeutic agent to a target tissue (such as tumor, for example solid tumor) in an individual, comprising: a) administering the therapeutic agent to the individual and determining tissue uptake of the therapeutic agent; and 2) administering to the individual the therapeutic agent in conjunction with a composition comprising nanoparticles comprising an albumin and a taxane, wherein the average particle size of the nanoparticle composition is no greater than about 200 nm. In some embodiments, there is provided a method of facilitating the uptake a therapeutic agent to a target tissue (such as tumor, for example solid tumor) in an individual, comprising: a) administering the therapeutic agent to the individual and determining tissue uptake of the therapeutic agent; and 2) administering to the individual the therapeutic agent in conjunction with a composition comprising nanoparticles comprising an albumin and a taxane, wherein the taxane in the nanoparticles is coated with albumin, and wherein the average size of the nanoparticles in the nanoparticle composition is no greater than about 200 nm. In some embodiments, the taxane nanoparticle composition is administered weekly. In some embodiments, the taxane nanoparticle composition is administered intravenously. In some embodiments, the taxane nanoparticle composition is intravenously administered weekly.

In some embodiments, there is provided a method of facilitating the uptake a therapeutic agent to a target tissue (such as tumor, for example solid tumor) in an individual, comprising: a) administering the therapeutic agent to the individual and determining tissue uptake of the therapeutic agent; and 2) administering to the individual the therapeutic agent in conjunction with Nab-paclitaxel (Abraxane®). In some embodiments, the Nab-paclitaxel (Abraxane®) is administered weekly. In some embodiments, the Nab-paclitaxel (Abraxane®) is administered intravenously. In some embodiments, the Nab-paclitaxel (Abraxane®) is intravenously administered weekly.

Tissue uptake of therapeutic agents can be determined by methods known in the art. These include, for example, LCMS, HPLC, radiolabel, ELISA, and fluorescent studies. In some embodiments, the tissue uptake (such as tumor uptake) of the therapeutic agent is enhanced at least about 10%, including for example at least about any of 20%, 30%, 40%, 50%, 60%, 70%, 80%, 90%, 100%, 200%, or more, compared to the tissue uptake of the therapeutic agent not co-administered with the taxane nanoparticle composition. In some embodiments, the tissue uptake (such as tumor uptake) of the therapeutic agent is enhanced about 10% to 20%, 20% to 30%, 30% to 40%, 40% to 50%, 50% to 60%, 60% to 70%, 70% to 80%, 80% to 90%, 90% to 100%, or 100% to 200%, compared to the tissue uptake of the therapeutic agent not co-administered with the taxane nanoparticle composition.

In some embodiments, there is provided a method of increasing penetration of a therapeutic agent into a target tissue (such as tumor) in an individual, comprising administering to the individual the therapeutic agent in conjunction with a composition comprising nanoparticles comprising an albumin and a taxane. In some embodiments, there is provided a method of increasing penetration of a therapeutic agent into a tumor (such as solid tumor) in an individual, comprising administering to the individual the therapeutic agent in conjunction with a composition comprising nanoparticles comprising an albumin and a taxane. In some embodiments, the penetration of the therapeutic agent is increased at least about 10%, including for example at least about any of 20%, 30%, 40%, 50%, 60%, 70%, 80%, 90%, 100%, 200%, or more, compared to the penetration of the therapeutic agent not co-administered with the taxane nanoparticle composition. In some embodiments, the penetration of the therapeutic agent is increased about 10% to 20%, 20% to 30%, 30% to 40%, 40% to 50%, 50% to 60%, 60% to 70%, 70% to 80%, 80% to 90%, 90% to 100%, or 100% to 200%, compared to the penetration of the therapeutic agent not co-administered with the taxane nanoparticle composition. In some embodiments, the taxane nanoparticle composition is administered weekly. In some embodiments, the taxane nanoparticle composition is administered intravenously. In some embodiments, the taxane nanoparticle composition is intravenously administered weekly.

In some embodiments, there is provided a method of delivering a therapeutic agent to a target tissue (such as tumor) in an individual, comprising administering to the individual the therapeutic agent in conjunction with a composition comprising nanoparticles comprising an albumin and a taxane. In some embodiments, there is provided a method of delivering a therapeutic agent to a tumor (such as solid tumor) in an individual, comprising administering to the individual the therapeutic agent in conjunction with a composition comprising nanoparticles comprising an albumin and a taxane. In some embodiments, the delivery of the therapeutic agent is increased at least about 10%, including for example at least about any of 20%, 30%, 40%, 50%, 60%, 70%, 80%, 90%, 100%, 200%, or more, compared to the delivery of the therapeutic agent not co-administered with the taxane nanoparticle composition. In some embodiments, the delivery of the therapeutic agent is increased about 10% to 20%, 20% to 30%, 30% to 40%, 40% to 50%, 50% to 60%, 60% to 70%, 70% to 80%, 80% to 90%, 90% to 100%, or 100% to 200%, compared to the delivery of the therapeutic agent not co-administered with the taxane nanoparticle composition. In some embodiments, the taxane nanoparticle composition is administered weekly. In some embodiments, the taxane nanoparticle composition is administered intravenously. In some embodiments, the taxane nanoparticle composition is intravenously administered weekly.

In some embodiments, there is provided a method of enhancing effectiveness of a therapeutic agent for treating a disease in an individual, comprising administering to said individual an effective amount of the therapeutic agent in conjunction with a composition comprising nanoparticles comprising an albumin and a taxane. In some embodiments, the effectiveness of the therapeutic agent is enhanced by at least about 10%, including for example at least about any of 20%, 30%, 40%, 50%, 60%, 70%, 80%, 90%, 100%, 200%, or more, compared to the effectiveness without the co-administration of the taxane nanoparticle composition. In some embodiments, the effectiveness of the therapeutic agent is enhanced about 10% to 20%, 20% to 30%, 30% to 40%, 40% to 50%, 50% to 60%, 60% to 70%, 70% to 80%, 80% to 90%, 90% to 100%, or 100% to 200% compared to the effectiveness without the co-administration of the taxane nanoparticle composition. In some embodiments, the taxane nanoparticle composition is administered weekly. In some embodiments, the taxane nanoparticle composition is administered intravenously. In some embodiments, the taxane nanoparticle composition is intravenously administered weekly.

Also provided herein are methods of creating a microenvironment in a target tissue (such as tumor) in an individual that facilitates delivery of other therapeutic agent(s). For example, in some embodiments, there is provided a method of altering the microenvironment of a target tissue in an individual to facilitate uptake of a therapeutic agent, comprising administering to the individual a composition comprising nanoparticles comprising albumin and a taxane. In some embodiments, the method further comprises assessing the microenvironment in a target tissue prior to the administration of the taxane nanoparticle composition. Thus, for example, in some embodiments, there is provided a method of creating a microenvironment in a target tissue (such as tumor) in an individual that facilitates delivery of a therapeutic agent, comprising a) assessing the microenvironment in the target tissue; and b) administering to the individual an effective amount of a composition comprising nanoparticles comprising a taxane and an albumin (such as nanoparticles comprising a taxane coated with albumin). In some embodiments, there is provided a method of treating a disease in an individual, comprising a) assessing the microenvironment in the target tissue; and b) administering to the individual an effective amount of a composition comprising nanoparticles comprising a taxane and an albumin (such as nanoparticles comprising a taxane coated with albumin). Suitable indicators of microenvironment in a target tissue include, but are not limited to, the amount of tissue stroma, tissue vascularization, cell/vessel proximity, density of tumor matrix, and expression of stromal cell markers. In some embodiments, the taxane nanoparticle composition is administered weekly. In some embodiments, the taxane nanoparticle composition is administered intravenously. In some embodiments, the taxane nanoparticle composition is intravenously administered weekly.

In some embodiments, there is provided a method of reducing (such as disrupting, for example depleting) tumor stroma in an individual having a tumor, comprising administering to the individual a composition comprising nanoparticles comprising albumin and a taxane. In some embodiments, tumor stroma is disrupted by at least about any of 20%, 30%, 40%, 60%, 70%, 80%, 90%, or 100% compared to individuals not administered with the taxane nanoparticle composition. In some embodiments, the method further comprises a step of determining the amount of tumor stroma in an individual for the purpose of determining whether the individual is in need of (or suitable for) the method of reducing tumor stroma. Thus, for example, in some embodiments, there is provided a method of reducing (such as disrupting, for example depleting) tumor stroma in an individual having a tumor, comprising: a) determining the amount of tumor stroma in the individual, and b) administering to the individual a composition comprising nanoparticles comprising albumin and a taxane. In some embodiments, there is provided a method of reducing (such as disrupting, for example depleting) tumor stroma in an individual having a tumor, comprising: a) determining the amount of tumor stroma in the individual, and b) administering to the individual a composition comprising nanoparticles comprising albumin and a taxane, wherein the taxane in the nanoparticles is coated with albumin. In some embodiments, there is provided a method of reducing (such as disrupting, for example depleting) tumor stroma in an individual having a tumor, comprising: a) determining the amount of tumor stroma in the individual, and b) administering to the individual a composition comprising nanoparticles comprising albumin and a taxane, wherein the average size of the nanoparticles in the nanoparticle composition is no greater than about 200 nm. In some embodiments, there is provided a method of reducing (such as disrupting, for example depleting) tumor stroma in an individual having a tumor, comprising: a) determining the amount of tumor stroma in the individual, and b) administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of reducing (such as disrupting, for example depleting) tumor stroma in an individual having a tumor, comprising: a) determining the amount of tumor stroma in the individual, and b) administering to the individual Nab-paclitaxel (Abraxane®).

In some embodiments, there is provided a method of increasing tumor vascularization in an individual having a tumor, comprising administering to the individual a composition comprising nanoparticles comprising albumin and a taxane. In some embodiments, tumor vascularization is increased by at least about any of 20%, 30%, 40%, 60%, 70%, 80%, 90%, or 100% compared to individuals not administered with the taxane nanoparticle composition. In some embodiments, the method further comprises a step of determining the extent of tumor vascularization in an individual for the purpose of determining whether the individual is in need of (or suitable for) the method of increasing tumor vascularization. Thus, for example, in some embodiments, there is provided a method of increasing tumor vascularization in an individual having a tumor, comprising: a) determining the extent of tumor vascularization in the individual, and b) administering to the individual a composition comprising nanoparticles comprising albumin and a taxane. In some embodiments, there is provided a method of increasing tumor vascularization in an individual having a tumor, comprising: a) determining the extent of tumor vascularization in the individual, and b) administering to the individual a composition comprising nanoparticles comprising albumin and a taxane, wherein the taxane in the nanoparticles is coated with albumin. In some embodiments, there is provided a method of increasing tumor vascularization in an individual having a tumor, comprising: a) determining the extent of tumor vascularization in the individual, and b) administering to the individual a composition comprising nanoparticles comprising albumin and a taxane, wherein the average size of the nanoparticles in the nanoparticle composition is no greater than about 200 nm. In some embodiments, there is provided a method of increasing tumor vascularization in an individual having a tumor, comprising: a) determining the extent of tumor vascularization in the individual, and b) administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of increasing tumor vascularization in an individual having a tumor, comprising: a) determining the extent of tumor vascularization in the individual, and b) administering to the individual Nab-paclitaxel (Abraxane®).

In some embodiments, there is provided a method of increasing cell/vessel proximity in an individual having a tumor, comprising administering to the individual a composition comprising nanoparticles comprising albumin and a taxane. In some embodiments, cell/vessel proximity is increased by at least about any of 20%, 30%, 40%, 60%, 70%, 80%, 90%, or 100% compared to individuals not administered with the taxane nanoparticle composition. In some embodiments, the method further comprises a step of determining the extent of cell/vessel proximity in an individual for the purpose of determining whether the individual is in need of (or suitable) for the method of increasing cell/vessel proximity. Thus, for example, in some embodiments, there is provided a method of increasing cell/vessel proximity in an individual having a tumor, comprising: a) determining the extent of cell/vessel proximity in the individual, and b) administering to the individual a composition comprising nanoparticles comprising albumin and a taxane. In some embodiments, there is provided a method of increasing cell/vessel proximity in an individual having a tumor, comprising: a) determining the extent of cell/vessel proximity in the individual, and b) administering to the individual a composition comprising nanoparticles comprising albumin and a taxane, wherein the taxane in the nanoparticles is coated with albumin. In some embodiments, there is provided a method of increasing cell/vessel proximity in an individual having a tumor, comprising: a) determining the extent of cell/vessel proximity in the individual, and b) administering to the individual a composition comprising nanoparticles comprising albumin and a taxane, wherein the average size of the nanoparticles in the nanoparticle composition is no greater than about 200 nm. In some embodiments, there is provided a method of increasing cell/vessel proximity in an individual having a tumor, comprising: a) determining the extent of cell/vessel proximity in the individual, and b) administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of increasing cell/vessel proximity in an individual having a tumor, comprising: a) determining the extent of cell/vessel proximity in the individual, and b) administering to the individual Nab-paclitaxel (Abraxane®).

In some embodiments, there is provided a method of loosening (such as disrupting, for example destroying) the tumor matrix in an individual having a tumor, comprising administering to the individual a composition comprising nanoparticles comprising albumin and a taxane. In some embodiments, tumor matrix is disrupted by at least about any of 20%, 30%, 40%, 60%, 70%, 80%, 90%, or 100% compared to individuals not administered with the taxane nanoparticle composition. In some embodiments, the method further comprises a step of determining the density of the tumor matrix in an individual for the purpose of determining whether the individual is in need of (or suitable for) the method of loosening (such as disrupting, for example destroying) the tumor matrix. Thus, for example, in some embodiments, there is provided a method of loosening (such as disrupting, for example destroying) the tumor matrix in an individual having a tumor, comprising: a) determining the density of the tumor matrix in the individual, and b) administering to the individual a composition comprising nanoparticles comprising albumin and a taxane. In some embodiments, there is provided a method of loosening (such as disrupting, for example destroying) the tumor matrix in an individual having a tumor, comprising: a) determining the density of the tumor matrix in the individual, and b) administering to the individual a composition comprising nanoparticles comprising albumin and a taxane, wherein the taxane in the nanoparticles is coated with albumin. In some embodiments, there is provided a method of loosening (such as disrupting, for example destroying) the tumor matrix in an individual having a tumor, comprising: a) determining the density of the tumor matrix in the individual, and b) administering to the individual a composition comprising nanoparticles comprising albumin and a taxane, wherein the average size of the nanoparticles in the nanoparticle composition is no greater than about 200 nm. In some embodiments, there is provided a method of loosening (such as disrupting, for example destroying) the tumor matrix in an individual having a tumor, comprising: a) determining the density of the tumor matrix in the individual, and b) administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of loosening (such as disrupting, for example destroying) the tumor matrix in an individual having a tumor, comprising: a) determining the density of the tumor matrix in the individual, and b) administering to the individual Nab-paclitaxel (Abraxane®).

The methods described herein can be practiced in conjunction with the administration of other therapeutic agent(s). For example, the method can be practiced in conjunction with the administration of at least one, including for example 2, 3, 4, or 5 other therapeutic agents.

In some embodiments, the disease is cancer. The methods described herein are useful for various aspects of cancer treatment, including for example inhibiting cancer cell proliferation (for example inhibiting by at least about any of 20%, 30%, 40%, 60%, 70%, 80%, 90%, or 100%), inhibiting tumor metastasis (for example inhibiting by at least about any of 20%, 30%, 40%, 60%, 70%, 80%, 90%, or 100%), reducing pre-existing tumor metastasis (for example reducing by at least about any of 20%, 30%, 40%, 60%, 70%, 80%, 90%, or 100%), reducing incidence or burden of preexisting tumor metastasis (for example reducing by at least about any of 20%, 30%, 40%, 60%, 70%, 80%, 90%, or 100%), reducing tumor size (for example reducing by at least about any of 20%, 30%, 40%, 60%, 70%, 80%, 90%, or 100%), reducing tumor burden (for example reducing by at least about any of 20%, 30%, 40%, 60%, 70%, 80%, 90%, or 100%), prolonging time to disease progression of cancer (for example prolonging by at least any of 1, 2, 3, 4, 5, 6, 7, 8, 9, 10, 11, or 12 weeks), prolonging survival of an individual having cancer (for example prolonging by at least any of 1, 2, 3, 4, 5, 6, 7, 8, 9, 10, 11, or 12 months), prolonging disease free survival of an individual having cancer (for example prolonging by at least any of 1, 2, 3, 4, 5, 6, 7, 8, 9, 10, 11, or 12 months), and alleviating one or more symptoms in an individual having cancer. The present application thus provides methods relating to any one or more aspects of cancer treatment.

In some embodiments, the cancer is any of pancreatic cancer, lung cancer (such as NSCLC), melanoma, or prostate cancer. In some embodiments, the cancer is squamous cell carcinoma, such as squamous NSCLC. In some embodiments, the cancer is advanced cancer, such as advanced pancreatic cancer or advanced NSCLC. In some embodiments, the cancer is highly fibrotic and/or has dense stroma. In some embodiments, the cancer is breast cancer. In some embodiments, the cancer is head and neck cancer. In some embodiments, the cancer is esophageal cancer (such as squamous esophageal cancer). In some embodiments, the cancer is cervix cancer (such as squamous cervix cancer).

In some embodiments, the cancer is highly fibrotic and/or has a dense stroma. In some embodiments, the cancer is stromal rich and desmoplastic. These include, but are not limited to, squamous cell carcinomas (for example squamous cell carcinomas independent of location), biliopancreatic carcinomas, mesothelioma, desmoplastic fibroma, desmoplastic round cell tumor, breast cancer, ovarian cancer, colorectal carcinoma and tumors of gastrointestinal tract, lung cancers excluding small cell lung cancer, lymphomas, melanoma, brain tumors including cerebral astrocytoma, neuroblastoma, and medulloblastoma, in hepatocellular and urothelial tumors, and tumors of the pituitary gland.

In some embodiments, the cancer is highly fibrotic tumor and/or has a dense stroma and the cancer is not any of pancreatic cancer, lung cancer, melanoma, breast cancer, or prostate cancer. In some embodiments, the cancer is selected from the group consisting of: squamous cell carcinomas (for example squamous cell carcinomas independent of location), mesothelioma, desmoplastic fibroma, desmoplastic round cell tumor, colorectal carcinoma and tumors of gastrointestinal tract, lymphomas, and brain tumors including cerebral astrocytoma, neuroblastoma, and medulloblastoma, hepatocellular and urothelial tumors, and tumors of the pituitary gland. In some embodiments, the cancer is selected from the group consisting of: squamous cell carcinomas (for example squamous cell carcinomas independent of location), mesothelioma, desmoplastic fibroma, desmoplastic round cell tumor, colorectal carcinoma and tumors of gastrointestinal tract. In some embodiments, the cancer is squamous cell carcinoma. In some embodiments, the cancer is mesothelioma. In some embodiments, the cancer is desmoplastic fibroma. In some embodiments, the cancer is desmoplastic round cell tumor. In some embodiments, the cancer is colorectal carcinoma. In some embodiments, the cancer is tumor of the gastrointestinal tract.

Thus, for example, in some embodiments, there is provided a method of treating a cancer that is highly fibrotic and/or has a dense stroma in an individual, comprising administering to the individual an effective amount of a composition comprising nanoparticles comprising albumin and a taxane. In some embodiments, there is provided a method of treating a cancer that is highly fibrotic and/or has a dense stroma in an individual, comprising administering to the individual a composition comprising nanoparticles comprising albumin and a taxane, wherein the taxane in the nanoparticles is coated with albumin. In some embodiments, there is provided a method of treating a cancer that is highly fibrotic and/or has a dense stroma in an individual, comprising administering to the individual a composition comprising nanoparticles comprising albumin and a taxane, wherein the average size of the nanoparticles in the nanoparticle composition is no greater than about 200 nm. In some embodiments, there is provided a method of treating a cancer that is highly fibrotic and/or has a dense stroma in an individual, comprising administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of treating a cancer that is highly fibrotic and/or has a dense stroma in an individual, comprising administering to the individual Nab-paclitaxel (Abraxane®).

In some embodiments, there is provided a method of treating a cancer that is stromal rich and desmoplastic in an individual, comprising administering to the individual an effective amount of a composition comprising nanoparticles comprising albumin and a taxane. In some embodiments, there is provided a method of treating a cancer that is stromal rich and desmoplastic in an individual, comprising administering to the individual a composition comprising nanoparticles comprising albumin and a taxane, wherein the taxane in the nanoparticles is coated with albumin. In some embodiments, there is provided a method of treating a cancer that is stromal rich and desmoplastic in an individual, comprising administering to the individual a composition comprising nanoparticles comprising albumin and a taxane, wherein the average size of the nanoparticles in the nanoparticle composition is no greater than about 200 nm. In some embodiments, there is provided a method of treating a cancer that is stromal rich and desmoplastic in an individual, comprising administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of treating a cancer that is stromal rich and desmoplastic in an individual, comprising administering to the individual Nab-paclitaxel (Abraxane®).

In some embodiments, there is provided a method of treating a cancer in an individual, wherein the cancer is selected from the group consisting of: squamous cell carcinomas (for example squamous cell carcinomas independent of location), mesothelioma, desmoplastic fibroma, desmoplastic round cell tumor, colorectal carcinoma and tumors of gastrointestinal tract, comprising administering to the individual an effective amount of a composition comprising nanoparticles comprising albumin and a taxane. In some embodiments, there is provided a method of treating a cancer in an individual, wherein the cancer is selected from the group consisting of: squamous cell carcinomas (for example squamous cell carcinomas independent of location), mesothelioma, desmoplastic fibroma, desmoplastic round cell tumor, colorectal carcinoma and tumors of gastrointestinal tract, comprising administering to the individual a composition comprising nanoparticles comprising albumin and a taxane, wherein the taxane in the nanoparticles is coated with albumin. In some embodiments, there is provided a method of treating a cancer in an individual, wherein the cancer is selected from the group consisting of: squamous cell carcinomas (for example squamous cell carcinomas independent of location), mesothelioma, desmoplastic fibroma, desmoplastic round cell tumor, colorectal carcinoma and tumors of gastrointestinal tract, comprising administering to the individual a composition comprising nanoparticles comprising albumin and a taxane, wherein the average size of the nanoparticles in the nanoparticle composition is no greater than about 200 nm. In some embodiments, there is provided a method of treating a cancer in an individual, wherein the cancer is selected from the group consisting of: squamous cell carcinomas (for example squamous cell carcinomas independent of location), mesothelioma, desmoplastic fibroma, desmoplastic round cell tumor, colorectal carcinoma and tumors of gastrointestinal tract, comprising administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of treating a cancer in an individual, wherein the cancer is selected from the group consisting of: squamous cell carcinomas (for example squamous cell carcinomas independent of location), mesothelioma, desmoplastic fibroma, desmoplastic round cell tumor, colorectal carcinoma and tumors of gastrointestinal tract, comprising administering to the individual Nab-paclitaxel (Abraxane®).

In some embodiments, the cancer is identified as having high expression of one or more stromal cell markers. Thus, for example, in some embodiments, there is provided a method of treating a cancer in an individual, wherein the cancer overexpresses one or more (such as at least 1, 2, 3, 4, 5, 6, 7, or 8) stromal cell markers, comprising administering to the individual an effective amount of a composition comprising nanoparticles comprising albumin and a taxane. In some embodiments, there is provided a method of treating a cancer in an individual, wherein the cancer overexpresses one or more (such as at least 1, 2, 3, 4, 5, 6, 7, or 8) stromal cell markers, comprising administering to the individual a composition comprising nanoparticles comprising albumin and a taxane, wherein the taxane in the nanoparticles is coated with albumin. In some embodiments, there is provided a method of treating a cancer in an individual, wherein the cancer overexpresses (such as at least 1, 2, 3, 4, 5, 6, 7, or 8) stromal cell markers, comprising administering to the individual a composition comprising nanoparticles comprising albumin and a taxane, wherein the average size of the nanoparticles in the nanoparticle composition is no greater than about 200 nm. In some embodiments, there is provided a method of treating a cancer in an individual, wherein the cancer overexpresses (such as at least 1, 2, 3, 4, 5, 6, 7, or 8) stromal cell markers, comprising administering to the individual a composition comprising nanoparticles comprising albumin and a taxane, wherein the taxane in the nanoparticles is coated with albumin, and wherein the average size of the nanoparticles in the nanoparticle composition is no greater than about 200 nm. In some embodiments, there is provided a method of treating a cancer in an individual, wherein the cancer overexpresses (such as at least 1, 2, 3, 4, 5, 6, 7, or 8) stromal cell markers, comprising administering to the individual Nab-paclitaxel (Abraxane®). Suitable stromal markers include, but are not limited to, Cadherin-11, Calretinin, CD10, CD117, Desmin, Endoglyx-1, Endosialin (TEM1, CD248), Fibroblast-Activation Protein (FAP), Laminin gamma2 chain, Neural Ganglioside GD2, Nucleostemin, Snep (stromal nidogen extracellular matrix protein), Tenascin. Other stromal cell markers include, for example, stromal cell-associated markers such as CD13, CD29, CD44, CD63, CD73, CD90, CD166, STRO-1; markers of primitive human marrow stromal cells such as HOP-26 (CD63), CD49a and SB-10 (CD166); stromal differentiation markers such as alpha and beta subunits of inhibin/activin; and stromal markers in endometrial mucosa such as alpha-smooth muscle actin and other stromal markers in endometrial mucosa.

In some embodiments, the target tissue is a site of inflammation. In some embodiments, the target tissue is a site of tissue remodeling. In some embodiments, the target tissue is a site of wound healing.

In some embodiments, the target tissue has low vascularity. In some embodiments, the target tissue is hyper-fibrotic. In some embodiments, the target tissue has a dense stroma. In some embodiments, the target tissue is difficult to penetrate by therapeutic agents.

In some embodiments, the target tissue has a drug uptake capability. Drug uptake capability can be determined, for example, by one or more of the following characteristics: 1) increased albumin uptake; 2) increased caveolin-1 expression; 3) increased gp60 expression; and 4) increased SPARC expression.

In some embodiments, the target tissue has a high albumin uptake based on comparison with a population of normal individuals. In some embodiments, the target tissue has high albumin uptake based on comparison with a population of individuals having the same disease. In some embodiments, the target tissue has a high albumin uptake based on comparison with the normal tissue (or a different diseased tissue) in the same individual.

In some embodiments, the target tissue has a high level of Caveolin-1, gp60, or SPARC expression based on comparison with a population of normal individuals. In some embodiments, the target tissue has a high level of Caveolin-1, gp60, or SPARC expression based on comparison with a population of individuals having the same disease. In some embodiments, the target tissue has a high level of Caveolin-1, gp60, or SPARC expression based on comparison with the normal tissue (or a different diseased tissue) in the same individual.

In some embodiments, the disease is not responsive to the treatment of the taxane nanoparticle composition when administered alone. For example, the taxane nanoparticle composition can be used for treating the disease only when administered in conjunction with a therapeutic agent. This can be due, for example, to the fact that the only effect of the taxane nanoparticle composition is to facilitate the delivery of the co-administered therapeutic agent to the target tissue. Thus, for example, in some embodiments, there is provided a method of treating a disease (such as cancer) that is not responsive to the treatment of a composition comprising nanoparticles comprising albumin and a taxane when administered alone, comprising administering to the individual a) an effective amount of a composition comprising nanoparticles comprising albumin and a taxane; and b) at least one other therapeutic agent. In some embodiments, there is provided a method of treating a disease (such as cancer) that is not responsive to the treatment of a therapeutic agent when administered alone, comprising administering to the individual a) an effective amount of a composition comprising nanoparticles comprising albumin and a taxane, and b) the therapeutic agent. In some embodiments, there is provided a method of treating a disease (such as cancer) that is not responsive to the treatment of a composition comprising nanoparticles comprising albumin and a taxane when administered alone or to the treatment of another therapeutic agent alone, comprising administering to the individual a) an effective amount of a composition comprising nanoparticles comprising albumin and a taxane; and b) the other therapeutic agent.

In some embodiments, there is provided a method of treating a disease (such as cancer) that is not responsive to the treatment of a composition comprising nanoparticles comprising albumin and a taxane when administered alone, comprising administering to the individual a) an effective amount of a composition comprising nanoparticles comprising albumin and a taxane, wherein the taxane in the nanoparticle composition is coated with albumin; and b) at least one other therapeutic agent. In some embodiments, there is provided a method of treating a disease (such as cancer) that is not responsive to the treatment of a therapeutic agent when administered alone, comprising administering to the individual a) an effective amount of a composition comprising nanoparticles comprising albumin and a taxane, wherein the taxane in the nanoparticles is coated with albumin, and b) the therapeutic agent. In some embodiments, there is provided a method of treating a disease (such as cancer) that is not responsive to the treatment of a composition comprising nanoparticles comprising albumin and a taxane when administered alone or to the treatment of another therapeutic agent alone, comprising administering to the individual a) an effective amount of a composition comprising nanoparticles comprising albumin and a taxane wherein the taxane in the nanoparticle composition is coated with albumin; and b) the other therapeutic agent.

In some embodiments, there is provided a method of treating a disease (such as cancer) that is not responsive to the treatment of a composition comprising nanoparticles comprising albumin and a taxane when administered alone, comprising administering to the individual a) an effective amount of a composition comprising nanoparticles comprising albumin and a taxane, wherein the average size of the nanoparticles in the nanoparticle composition is no greater than about 200 nm; and b) at least one other therapeutic agent. In some embodiments, there is provided a method of treating a disease (such as cancer) that is not responsive to the treatment of a therapeutic agent when administered alone, comprising administering to the individual a) an effective amount of a composition comprising nanoparticles comprising albumin and a taxane, wherein the average size of the nanoparticles in the nanoparticle composition is no greater than about 200 nm; and b) the therapeutic agent. In some embodiments, there is provided a method of treating a disease (such as cancer) that is not responsive to the treatment of a composition comprising nanoparticles comprising albumin and a taxane when administered alone or to the treatment of another therapeutic agent alone, comprising administering to the individual a) an effective amount of a composition comprising nanoparticles comprising albumin and a taxane, wherein the average size of the nanoparticles in the nanoparticle composition is no greater than about 200 nm; and b) the other therapeutic agent.

In some embodiments, there is provided a method of treating a disease (such as cancer) that is not responsive to the treatment of a composition comprising nanoparticles comprising albumin and a taxane when administered alone, comprising administering to the individual a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and b) at least one other therapeutic agent. In some embodiments, there is provided a method of treating a disease (such as cancer) that is not responsive to the treatment of a therapeutic agent when administered alone, comprising administering to the individual a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and b) the therapeutic agent. In some embodiments, there is provided a method of treating a disease (such as cancer) that is not responsive to the treatment of a composition comprising nanoparticles comprising albumin and a taxane when administered alone or to the treatment of another therapeutic agent alone, comprising administering to the individual a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and b) the other therapeutic agent.

In some embodiments, there is provided a method of treating a disease (such as cancer) that is not responsive to the treatment of a composition comprising nanoparticles comprising albumin and a taxane when administered alone, comprising administering to the individual a) an effective amount of Nab-paclitaxel (Abraxane®); and b) at least one other therapeutic agent. In some embodiments, there is provided a method of treating a disease (such as cancer) that is not responsive to the treatment of a composition comprising nanoparticles comprising albumin and a taxane when administered alone or to the treatment of another therapeutic agent alone, comprising administering to the individual a) an effective amount of Nab-paclitaxel (Abraxane®); and b) the other therapeutic agent.

In some embodiments, the amount of the taxane in the taxane nanoparticle composition is not effective for treating the disease when administered alone. For example, in some embodiments, the amount of the taxane in the taxane nanoparticle composition is non-cytotoxic. In some embodiments, the amount of the taxane in the taxane nanoparticle composition is subtherapeutic. For example, the dose of the taxane in the taxane nanoparticle composition is less than about 50%, 40%, 30%, 20%, or 10% of the MTD.

Also provided herein are specific methods of combination therapy. In some embodiments, there is provided a method of treating pancreatic cancer (such as advanced pancreatic cancer), comprising administering: (a) a composition comprising nanoparticles comprising albumin and paclitaxel (such as nanoparticles comprising paclitaxel coated with albumin, for example Nab-paclitaxel), wherein the dose of the paclitaxel is about 100-150 mg/m$^2$, and (b) gemcitabine at a dose of about 100 mg/m$^2$. In some embodiments, the paclitaxel nanoparticle composition and the gemcitabine are administered weekly or once every three weeks. In some embodiments, the paclitaxel nanoparticle composition and the gemcitabine are administered weekly or once every three weeks for three weeks, followed by a week of rest.

In some embodiments, there is provided a method of treating prostate cancer (such as advanced prostate cancer), comprising administering: (a) a composition comprising nanoparticles comprising albumin and docetaxel (such as nanoparticles comprising docetaxel coated with albumin, for example Nab-docetaxel), and (b) prednisone. In some embodiments, there is provided a method of treating prostate cancer (such as advanced prostate cancer), comprising administering: (a) a composition comprising nanoparticles comprising albumin and docetaxel (such as nanoparticles comprising docetaxel coated with albumin, for example Nab-docetaxel), wherein the dose of the docetaxel is about 75 mg/m$^2$, and (b) prednisone. In some embodiments, the docetaxel nanoparticle composition and the prednisone are administered weekly or once every three weeks. In some embodiments, the docetaxel nanoparticle composition and the prednisone are administered weekly or once every three weeks for three weeks, followed by a week of rest.

Methods of Treatment Based Drug Uptake Capability

The present invention also provides methods of treatment or a method of selecting patients for treatment with the combination of a therapeutic agent and a composition comprising nanoparticles comprising albumin and a taxane based on the drug uptake capability of the target tissue. Target tissue having drug uptake capability is suitable for a treatment regime using the combination of the taxane nanoparticle composition and a therapeutic agent due to its ability to be rendered more accessible to the therapeutic agent by the taxane nanoparticle composition.

Accordingly, in some embodiments, there is provided a method of treating a disease (such as cancer) in an individual, comprising administering to the individual: (a) an effective amount of a composition comprising nanoparticles comprising albumin and a taxane, and (b) an effective amount of a therapeutic agent, wherein drug uptake capability is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane is the nanoparticles is coated with albumin; and (b) an effective amount of a therapeutic agent, wherein drug uptake capability is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the average size of the nanoparticles in the nanoparticle composition is no greater than about 200 nm; and (b) an effective amount of a therapeutic agent, wherein drug uptake capability is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and (b) an effective amount of a therapeutic agent, wherein drug uptake capability is used as a basis for selecting the individual to receive treatment. In some embodiments, there is provided a method of treating a disease (such as cancer) in an individual, comprising administering to the individual: (a) an effective amount of Nab-paclitaxel (Abraxane®); and (b) an effective amount of a therapeutic agent, wherein drug uptake capability is used as a basis for selecting the individual to receive treatment.

In some embodiments, the drug uptake capability is based on one or more of the following: 1) increased albumin uptake; 2) increased caveolin-1 expression; 3) increased gp60 expression; and 4) increased SPARC expression. Thus, for example, in some embodiments, there is provided a method of treating a disease (such as cancer) in an individual, comprising administering to the individual: (a) an effective amount of a composition comprising nanoparticles comprising albumin and a taxane, and (b) an effective amount of a therapeutic agent, wherein albumin uptake is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane is the nanoparticles is coated with albumin; and (b) an effective amount of a therapeutic agent, wherein albumin uptake is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the average size of the nanoparticles in the nanoparticle composition is no greater than about 200 nm; and (b) an effective amount of a therapeutic agent, wherein albumin uptake is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and (b) an effective amount of a therapeutic agent, wherein albumin uptake is used as a basis for selecting the individual to receive treatment. In some embodiments, there is provided a method of treating a disease (such as cancer) in an individual, comprising administering to the individual: (a) an effective amount of Nab-paclitaxel (Abraxane®); and (b) an effective amount of a therapeutic agent, wherein albumin uptake is used as a basis for selecting the individual to receive treatment.

In some embodiments, there is provided a method of treating a disease (such as cancer) in an individual, comprising administering to the individual: (a) an effective amount of a composition comprising nanoparticles comprising albumin and a taxane, and (b) an effective amount of a therapeutic agent, wherein caveolin-1 expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane is the nanoparticles is coated with albumin; and (b) an effective amount of a therapeutic agent, wherein caveolin-1 expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the average size of the nanoparticles in the nanoparticle composition is no greater than about 200 nm; and (b) an effective amount of a therapeutic agent, wherein caveolin-1 expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and (b) an effective amount of a therapeutic agent, wherein caveolin-1 expression is used as a basis for selecting the individual to receive treatment. In some embodiments, there is provided a method of treating a disease (such as cancer) in an individual, comprising administering to the individual: (a) an effective amount of Nab-paclitaxel (Abraxane®); and (b) an effective amount of a therapeutic agent, wherein caveolin-1 expression is used as a basis for selecting the individual to receive treatment.

In some embodiments, there is provided a method of treating a disease (such as cancer) in an individual, comprising administering to the individual: (a) an effective amount of a composition comprising nanoparticles comprising albumin and a taxane, and (b) an effective amount of a therapeutic agent, wherein gp60 expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane is the nanoparticles is coated with albumin; and (b) an effective amount of a therapeutic agent, wherein gp60 expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the average size of the nanoparticles in the nanoparticle composition is no greater than about 200 nm; and (b) an effective amount of a therapeutic agent, wherein gp60 expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and (b) an effective amount of a therapeutic agent, wherein gp60 expression is used as a basis for selecting the individual to receive treatment. In some embodiments, there is provided a method of treating a disease (such as cancer) in an individual, comprising administering to the individual: (a) an effective amount of Nab-paclitaxel (Abraxane®); and (b) an effective amount of a therapeutic agent, wherein gp60 expression is used as a basis for selecting the individual to receive treatment.

In some embodiments, there is provided a method of treating a disease (such as cancer) in an individual, comprising administering to the individual: (a) an effective amount of a composition comprising nanoparticles comprising albumin and a taxane, and (b) an effective amount of a therapeutic agent, wherein SPARC expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane is the nanoparticles is coated with albumin; and (b) an effective amount of a therapeutic agent, wherein SPARC expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the average size of the nanoparticles in the nanoparticle composition is no greater than about 200 nm; and (b) an effective amount of a therapeutic agent, wherein SPARC expression is used as a basis for selecting the individual to receive treatment. In some embodiments, there is provided a method of treating a disease (such as cancer) in an individual, comprising administering to the individual: (a) an effective amount of a composition comprising nanoparticles comprising albumin and a taxane, wherein the taxane in the nanoparticles is coated with albumin and wherein the average size of the nanoparticles in the nanoparticle composition is no greater than about 200 nm; and (b) an effective amount of a therapeutic agent, wherein SPARC expression is used as a basis for selecting the individual to receive treatment. In some embodiments, there is provided a method of treating a disease (such as cancer) in an individual, comprising administering to the individual: (a) an effective amount of Nab-paclitaxel (Abraxane®); and (b) an effective amount of a therapeutic agent, wherein SPARC expression is used as a basis for selecting the individual to receive treatment.

In some embodiments, there is provided a method of treating a disease (such as cancer) in an individual, comprising: (a) determining the drug uptake capability of the target tissue in the individual, and (b) administering to the individual: (1) an effective amount of a composition comprising nanoparticles comprising albumin and a taxane (such as nanoparticles comprising a taxane coated with albumin, for example Nab-paclitaxel), and (2) a therapeutic agent. In some embodiments, the method further comprises isolating a tissue sample from said individual for the determination of drug uptake capability. It is also conceivable that one of skill in the art may be able to analyze and determine drug uptake capability in situ. Accordingly, the methods of this application are not to be limited to requiring isolation of a sample prior to analysis.

In some embodiments, there is provided a method of treating a disease (such as cancer) in an individual, comprising: (a) determining the albumin uptake of the target tissue in the individual, and (b) administering to the individual: (1) an effective amount of a composition comprising nanoparticles comprising albumin and a taxane (such as nanoparticles comprising a taxane coated with albumin, for example Nab-paclitaxel), and (2) a therapeutic agent. In some embodiments, there is provided a method of treating a disease (such as cancer) in an individual, comprising: (a) determining the caveolin-1 expression of the target tissue in the individual, and (b) administering to the individual: (1) an effective amount of a composition comprising nanoparticles comprising albumin and a taxane (such as nanoparticles comprising a taxane coated with albumin, for example Nab-paclitaxel), and (2) a therapeutic agent. In some embodiments, there is provided a method of treating a disease (such as cancer) in an individual, comprising: (a) determining gp60 expression of the target tissue in the individual, and (b) administering to the individual: (1) an effective amount of a composition comprising nanoparticles comprising albumin and a taxane (such as nanoparticles comprising a taxane coated with albumin, for example Nab-paclitaxel), and (2) a therapeutic agent. In some embodiments, there is provided a method of treating a disease (such as cancer) in an individual, comprising: (a) determining SPARC expression of the target tissue in the individual, and (b) administering to the individual: (1) an effective amount of a composition comprising nanoparticles comprising albumin and a taxane (such as nanoparticles comprising a taxane coated with albumin, for example Nab-paclitaxel), and (2) a therapeutic agent.

In some embodiments, there is provided a method of assessing responsiveness of an individual to a treatment method comprising administration of (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining drug uptake capability of the target tissue in the individual, wherein a drug uptake capability is indicative that the individual is responsive to the treatment. In some embodiments, the method further comprises administering the effective amount of a composition comprising nanoparticles comprising albumin and a taxane and a therapeutic agent to the individual who is determined to be responsive to the treatment. The assessment of responsiveness based on drug uptake capability can be carried out before or after the administration methods. In some embodiments, the responsiveness of the individual to treatment can be assessed after the administration method based on other indications. For example, in some embodiments, there is provided a method of assessing responsiveness of an individual to treatment method comprising administration of (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining uptake of the therapeutic agent by the target tissue in the individual, wherein a high uptake of the therapeutic agent (for example when the target tissue has about any of 10%, 20%, 30%, 40%, 50%, 60%, 70%, or more of the total administered therapeutic agent) is indicative that the individual is responsive to the treatment.

In some embodiments, there is provided a method of assessing responsiveness of an individual to treatment method comprising administration of (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining the extent of stroma destruction in the target tissue in the individual, wherein a disrupted stroma (for example when the stroma is disrupted by at least about any of 20%, 30%, 40%, 50%, 60%, 70%, 80%, 90%, or 100% compared to individuals not administered with the taxane nanoparticle composition) is indicative that the individual is responsive to the treatment.

In some embodiments, there is provided a method of assessing responsiveness of an individual to treatment method comprising administration of (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining the extent of tumor vascularization in the target tissue in the individual, wherein an increased tumor vascularization (for example when the tumor vascularization is increased by at least about any of 20%, 30%, 40%, 50%, 60%, 70%, 80%, 90%, or 100% compared to individuals not administered with the taxane nanoparticle composition) is indicative that the individual is responsive to the treatment.

In some embodiments, there is provided a method of screening for an individual for a treatment comprising administration of (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining drug uptake capability of the target tissue in the individual, wherein the individual is selected if said individual has a drug uptake capability in the target tissue. In some embodiments, the method further comprises administering effective amounts of a composition comprising nanoparticles comprising albumin and a taxane and a therapeutic agent to the selected individual.

In some embodiments, there is provided a method of determining whether an individual is suitable for treatment with (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining drug uptake capability of the target tissue in the individual, wherein a drug uptake capability is indicative that the individual is suitable for the treatment. In some embodiments, the method further comprises administering effective amounts of a composition comprising nanoparticles comprising albumin and a taxane and a therapeutic agent to the individual who is determined to be suitable for the treatment.

In some embodiments, there is provided a method of determining whether an individual is unsuitable for treatment with (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining drug uptake capability of the target tissue in the individual, wherein a lack of drug uptake capability is indicative that the individual is unsuitable for the treatment.

In some embodiments, there is provided a method of determining whether an individual is suitably treated with (a) an effective amount of a composition comprising nanoparticles comprising albumin and a taxane (such as nanoparticles comprising a taxane coated with albumin, for example Nab-paclitaxel) and (b) an effective amount of a therapeutic agent, the method comprising determining drug uptake capability of the target tissue in the individual, wherein a drug uptake capability is indicative that the individual is suitably treated. In some embodiments, the method further comprises continuing to administer effective amounts of a composition comprising nanoparticles comprising albumin and a taxane and a therapeutic agent to the individual who is determined to be suitably treated.

In some embodiments, there is provided a method of monitoring treatment of a disease in an individual comprising administering to the individual (a) an effective amount of a composition comprising nanoparticles comprising albumin and a taxane (such as nanoparticles comprising a taxane coated with albumin, for example Nab-paclitaxel) and (b) an effective amount of a therapeutic agent, said method comprising determining the drug uptake capability of the target tissue in the individual.

With respect to methods described herein, the screening methods (i.e., methods of identifying individuals as suitable or unsuitable for treatment) may be practiced independently of the treatment methods, and as such are distinct from treatment methods. The screening methods described herein may be practiced by a skilled technician other than a medical doctor.

Responsiveness or suitability for treatment can be evaluated, for example, based on objective criteria, such as performance status, physical examination, imaging studies, or laboratory test results. Responsiveness or suitability for treatment can also be evaluated based on subjective criteria reported by the individual, such as pain, distress, fatigue, or mental outlook. In the context of treating cancer, decrease in tumor size can be used as a criterion for determining responsiveness and/or suitability. Decrease in tumor size can be based on the primary tumor or overall tumor burden measured by any suitable measurable methods known in the art, e.g., physical examination, imaging study, or laboratory value.

Suitable selection criteria (for example for cancer treatment) include, but are not limited to, increased albumin uptake in the target tissue (such as tumor), increased levels of caveolin-1 in the target tissue (such as tumor), increased level of gp60 in the target tissue (such as tumor), increased level of SPARC in the target tissue (such as tumor).

In some embodiments, the drug uptake capability is determined by albumin uptake. In some embodiments, the drug uptake capability is determined by the level of caveolin-1. In some embodiments, the drug uptake capability is determined by the level of gp-60. In some embodiments, the drug uptake capability is determined by the level of SPARC.

In some embodiments, the drug uptake capability is determined by two or more parameters. For example, in some embodiments, the drug uptake capability is determined based on both the caveolin-1 level and the gp-60 level. In some embodiments, the drug uptake capability is based on the caveolin-1 and the SPARC level. In some embodiments, the drug uptake capability is based on the levels of caveolin-1, gp60, and SPARC. In some embodiments, the drug uptake capability is based on the levels of albumin uptake, gp60, and SPARC. Other combinations of these characteristics are also contemplated.

Thus, for example, in some embodiments, there is provided a method of treating cancer in an individual in need thereof, comprising administering to the individual a) a composition comprising nanoparticles comprising albumin and a taxane (such as a composition comprising nanoparticles comprising a taxane coated with albumin, for example Nab-paclitaxel), and b) a therapeutic agent, wherein treatment is based on the individual having one or more characteristics selected from the group consisting of: increased albumin uptake in the tumor tissue, increased levels of caveolin-1 in the tumor tissue, increased level of gp60 in the tumor tissue, increased level of SPARC in the tumor tissue.

In some embodiments, there is provided a method of treating cancer in an individual in need thereof, comprising administering to the individual a) a composition comprising nanoparticles comprising albumin and a taxane (such as a composition comprising nanoparticles comprising a taxane coated with albumin, for example Nab-paclitaxel), and b) a therapeutic agent, wherein treatment is based on the individual having two or more characteristics selected from the group consisting of: increased albumin uptake in the tumor tissue, increased levels of caveolin-1 in the tumor tissue, increased level of gp60 in the tumor tissue, increased level of SPARC in the tumor tissue. In some embodiments, there is provided a method of treating cancer in an individual in need thereof, comprising administering to the individual a) a composition comprising nanoparticles comprising albumin and a taxane (such as a composition comprising nanoparticles comprising a taxane coated with albumin, for example Nab-paclitaxel), and b) a therapeutic agent, wherein treatment is based on the individual having three or more characteristics selected from the group consisting of: increased albumin uptake in the tumor tissue, increased levels of caveolin-1 in the tumor tissue, increased level of gp60 in the tumor tissue, increased level of SPARC in the tumor tissue. In some embodiments, there is provided a method of treating cancer in an individual in need thereof, comprising administering to the individual a) a composition comprising nanoparticles comprising albumin and a taxane (such as a composition comprising nanoparticles comprising a taxane coated with albumin, for example Nab-paclitaxel), and b) a therapeutic agent, wherein treatment is based on the individual having: increased albumin uptake in the tumor tissue, increased levels of caveolin-1 in the tumor tissue, and increased level of gp60 in the tumor tissue. In some embodiments, there is provided a method of treating cancer in an individual in need thereof, comprising administering to the individual a) a composition comprising nanoparticles comprising albumin and a taxane (such as a composition comprising nanoparticles comprising a taxane coated with albumin, for example Nab-paclitaxel), and b) a therapeutic agent, wherein treatment is based on the individual having: increased albumin uptake in the tumor tissue, increased levels of caveolin-1 in the tumor tissue, increased level of gp60 in the tumor tissue, increased level of SPARC in the tumor tissue.

In some embodiments, there is provided a method of treating cancer in an individual in need thereof, provided that the individual has been found to have one or more characteristics selected from the group consisting of: increased albumin uptake in the tumor tissue, increased levels of caveolin-1 in the tumor tissue, increased level of gp60 in the tumor tissue, increased level of SPARC in the tumor tissue, the treatment comprising administering to the individual a) a composition comprising nanoparticles comprising albumin and a taxane, and b) a therapeutic agent.

In some embodiments, there is provided a method of treating cancer, comprising: (a) selecting an individual having cancer, wherein the cancer has one or more (or two or more, three or more) characteristics selected from the group consisting of: increased albumin uptake in the tumor tissue, increased levels of caveolin-1 in the tumor tissue, increased level of gp60 in the tumor tissue, increased level of SPARC in the tumor tissue; and (b) administering to the individual a) a composition comprising nanoparticles comprising albumin and a taxane (such as nanoparticle compositions comprising a taxane coated with albumin, for example Nab-pacltiaxel), and b) a therapeutic agent. In some embodiments, there is provided a method of treating cancer, comprising: (a) selecting an individual having cancer, wherein the cancer has one or more (or two or more, three or more) characteristics selected from the group consisting of: increased albumin uptake in the tumor tissue, increased levels of caveolin-1 in the tumor tissue, increased level of a gp60 in the tumor tissue, increased level of SPARC in the tumor tissue; and (b) administering to the individual a) a composition comprising nanoparticles comprising albumin and a taxane (such as nanoparticle compositions comprising a taxane coated with albumin, for example Nab-pacltiaxel), and b) a therapeutic agent. In some embodiments, there is provided a method of treating cancer, comprising: (a) selecting an individual having cancer, wherein the cancer has: increased albumin uptake in the tumor tissue, increased levels of caveolin-1 in the tumor tissue, and increased level of gp60 in the tumor tissue in the tumor tissue; and (b) administering to the individual a) a composition comprising nanoparticles comprising albumin and a taxane (such as nanoparticle compositions comprising a taxane coated with albumin, for example Nab-pacltiaxel), and b) a therapeutic agent. In some embodiments, there is provided a method of treating cancer, comprising: (a) selecting an individual having cancer, wherein the cancer has: increased albumin uptake in the tumor tissue, increased levels of caveolin-1 in the tumor tissue, increased level of gp60 in the tumor tissue, increased level of SPARC in the tumor tissue; and (b) administering to the individual a) a composition comprising nanoparticles comprising albumin and a taxane (such as nanoparticle compositions comprising a taxane coated with albumin, for example Nab-pacltiaxel), and b) a therapeutic agent.

In some embodiments, there is provided a method of assessing whether an individual having cancer will respond to treatment comprising administering to the individual a) a composition comprising nanoparticles comprising albumin and a taxane (such as nanoparticles comprising taxane coated with albumin, for example Nab-paclitaxel), and b) a therapeutic agent, comprising assessing one or more (or two or more, or three or more) characteristics selected from the group consisting of: increased albumin uptake in the tumor tissue, increased levels of caveolin-1 in the tumor tissue, increased level of gp60 in the tumor tissue, increased level of SPARC in the tumor tissue, wherein one or more of the characteristics of the cancer indicates that the individual will be responsive to the treatment. In some embodiments, there is provided a method of assessing whether an individual having cancer will respond to treatment comprising administering to the individual a) a composition comprising nanoparticles comprising albumin and a taxane (such as nanoparticles comprising taxane coated with albumin, for example Nab-paclitaxel), and b) a therapeutic agent, comprising assessing: increased albumin uptake in the tumor tissue, increased levels of caveolin-1 in the tumor tissue, and increased level of gp60 in the tumor tissue, wherein one or more (such as one, two, or three) of the characteristics of the cancer indicates that the individual will be responsive to the treatment. In some embodiments, there is provided a method of assessing whether an individual having cancer will respond to treatment comprising administering to the individual a) a composition comprising nanoparticles comprising albumin and a taxane (such as nanoparticles comprising taxane coated with albumin, for example Nab-paclitaxel), and b) a therapeutic agent, comprising assessing: increased albumin uptake in the tumor tissue, increased levels of caveolin-1 in the tumor tissue, increased level of gp60 in the tumor tissue, increased level of SPARC in the tumor tissue, wherein one or more (such as one, two, three, or four) of the characteristics of the cancer indicates that the individual will be responsive to the treatment.

In some embodiments, there is provided a method of identifying an individual having cancer likely to respond to treatment comprising administering to the individual a) a composition comprising nanoparticles comprising albumin and a taxane (such as nanoparticles comprising a taxane coated with albumin, for example Nab-paclitaxel), and b) a therapeutic agent, comprising: 1) assessing one or more (or two or more, or three or more) characteristics selected from the group consisting of: increased albumin uptake in the tumor tissue, increased levels of caveolin-1 in the tumor tissue, increased level of gp60 in the tumor tissue, increased level of SPARC in the tumor tissue, and 2) identifying the individual having one or more characteristics that is indicative of a higher likelihood of enhanced delivery of the therapeutic agent. In some embodiments, there is provided a method of identifying an individual having cancer likely to respond to treatment comprising administering to the individual a) a composition comprising nanoparticles comprising albumin and a taxane (such as nanoparticles comprising a taxane coated with albumin, for example Nab-paclitaxel), and b) a therapeutic agent, comprising: 1) assessing: increased albumin uptake in the tumor tissue, increased levels of caveolin-1 in the tumor tissue, increased level of gp60 in the tumor tissue, and 2) identifying the individual having one or more (such as one, two, or three) characteristics that is indicative of a higher likelihood of enhanced delivery of the therapeutic agent. In some embodiments, there is provided a method of identifying an individual having cancer likely to respond to treatment comprising administering to the individual a) a composition comprising nanoparticles comprising albumin and a taxane (such as nanoparticles comprising a taxane coated with albumin, for example Nab-paclitaxel), and b) a therapeutic agent, comprising: 1) assessing increased albumin uptake in the tumor tissue, increased levels of caveolin-1 in the tumor tissue, increased level of gp60 in the tumor tissue, and increased level of SPARC in the tumor tissue, and 2) identifying the individual having one or more (such as one, two, three, or four) characteristics that is indicative of a higher likelihood of enhanced delivery of the therapeutic agent.

Methods of Determining Drug Uptake Capability

Some methods described herein entails determining drug uptake capability in a target tissue or use of the drug uptake capability as a basis for selecting patients for treatment.

In some embodiments, the drug uptake capability is based on the albumin uptake in the target tissue. For example, albumin uptake can be evaluated histologically or by diagnostic imaging using known techniques such as gold-labeled albumin Albumin uptake can also be evaluated by ELISA.

In some embodiments, the drug uptake capability is based on the caveolin-1 level in the target tissue. Caveolin-1 is a major component of the caveolae. Expression of caveolin-1 is statistically correlated with pathologic stage of squamous cell carcinoma of the lung and is associated with poor prognosis of patients with squamous cell carcinoma of the lung. Yoo et al., Lung Cancer (2003) 42:195-202. Caveolin-1 has been shown to be overexpressed in metastatic prostate cancer (Yang, et al., Clin. Cancer Res., 4: 1873-1880, 1998), and serves as an independent prognostic marker for prostate cancer progression in lymph node-negative patients who have recurred after radical prostatectomy and that there is a significant association of increased caveolin-1 in prostate cancer in African-American men versus white-American men. Caveolin-1 up-regulation is also associated with the development of androgen-insensitive prostate cancer (Nasu et al., Nat. Med., 4: 1062-1064, 1998.). Androgen-insensitive prostate cancer cells secrete biologically active caveolin-1 in a steroid-regulated fashion (Tahir, et al., Cancer Res., 61: 3882-3885, 2001.). Secreted caveolin-1 can stimulate viability and clonal growth in prostate cancer cells that do not express caveolin-1, and by Western blot analysis, it is possible to detect caveolin-1 in the serum HDL3 fraction of prostate cancer patients (Tahir et al 2001).

In some embodiments, the drug uptake capability is based on high level of caveolin-1 in the tumor cells. In some embodiments, the drug uptake capability is based on the level of caveolin-1 on the blood vessel feeding the tumor cells. In some embodiments, the drug uptake capability is based on the level of caveolin-1 on the tumor stroma. In some embodiments, the drug uptake capability is based on the level of caveolin-1 on tumor cells.

In some embodiments, the drug uptake capability is based on the gp60 level in the target tissue. In some embodiments, the drug uptake capability is based on the level of gp60 in the tumor cells. In some embodiments, the drug uptake capability is based on the level of gp60 on the blood vessel feeding the tumor cells. In some embodiments, the drug uptake capability is based on the level of gp60 on the tumor stroma.

In some embodiments, the drug uptake capability is based on the SPARC level in the target tissue. SPARC (Secreted Protein, Acidic and Rich in Cysteine) is a matricellular protein upregulated in several aggressive cancers, but is absent in normal tissues (Porter et al., J. Histochem. Cytochem., 43, 791 (1995)). The human SPARC gene encodes a 303 amino acid SPARC protein, while mature SPARC is a 285 amino acid glycoprotein. After cleavage of the signal sequence a 32-kD secreted form is produced which migrates at 43 kD on SDA-PAGE because of glycosylation. The expression of SPARC is induced in a variety of tumors. See PCT Publication Nos. WO08/060,651 and 05/117,952, the contents of both of which are incorporated herein in their entirety. In some embodiments, the drug uptake capability is based on the level of SPARC in the tumor cells. In some embodiments, the drug uptake capability is based on the level of SPARC on the tumor stroma.

The levels of the biomarkers described herein (such as caveolin-1, gp60, and SPARC) can be determined based on expression levels. In some embodiments, expression level of a biomarker is determined by measuring the gene expression level for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest. In some embodiments, the single patient has a disease (such as cancer) and the patient population does not have the disease (i.e., normal). In some embodiments, the single patient has one histological type of a disease (e.g., squamous cell carcinoma) and the patient population has a second histological type of a disease (e.g., adenocarcinoma). In some embodiments, the single patient and the patient population have the same histological type of a disease (e.g., squamous cell carcinoma). Nucleic acid (e.g., RNA or DNA) or protein levels of the gene of interest can be measured. Methods for measuring gene expression are well known in the art and include, but are not limited to, immunological assays, nuclease protection assays, northern blots, in situ hybridization, ELISA, reverse transcriptase Polymerase Chain Reaction (RT-PCR), Real-Time Polymerase Chain Reaction, expressed sequence tag (EST) sequencing, cDNA microarray hybridization or gene chip analysis, subtractive cloning, Serial Analysis of Gene Expression (SAGE), Massively Parallel Signature Sequencing (MPSS), and Sequencing-By-Synthesis (SBS). Diagnostic procedures can also be performed in situ directly upon tissue sections (fixed and/or frozen) of patient tissue obtained from biopsies or resections. Amplification of polynucleotides includes methods such as PCR, ligation amplification (or ligase chain reaction, LCR) and amplification methods. These methods are known and widely practiced in the art.). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

In some embodiments, a biopsy of the target tissue (such as tumor) can be prepared for immunohistology with an antibody recognizing a biomarker (such as caveolin-1, gp60, and SPARC) by preparing thin sections of the biopsy in a microscope slide. For example, for the determination of SPARC level, the biopsy slides can be stained with an anti-SPARC antibody using an anti-SPARC immunohistological protocol simultaneously with control slides containing sections of biopsies with known SPARC levels from normal tissues or other tumor tissues. The intensity of the immunohistological staining can be graded, for example, by using light microscopy. A staining grade (e.g., 0, 1+, 2+, 3+, 4+) can be assigned based on the staining. An individual can be determined to have drug uptake capability based on the tumor biopsy grades of, for example, 2+, 3+, 4+, or higher.

In some embodiments, the target tissue has a high albumin uptake (or high level of a biomarker described herein) based on comparison with a population of normal individuals.

In some embodiments, the target tissue has a high albumin uptake (or high level of a biomarker described herein) based on comparison with a population of individuals having the same disease. In some embodiments, the target tissue has a a high albumin uptake (or high level of a biomarker described herein) based on comparison with the normal tissue (or a different diseased tissue) in the same individual.

In some embodiments, an individual is selected for treatment based on a percentile ranking of albumin uptake level (or levels of one or more biomarkers described herein) compared to a population. For example, there is a range of albumin uptake level (or levels of one or more biomarkers described herein) over a given patient population, and individuals suitable for treatment (or, conversely, individuals likely to be unsuitable) can be identified based on a percentile ranking of albumin uptake level (or levels of one or more biomarkers described herein) with respect to this population. Accordingly, in some embodiments, an individual is included in treatment, or identified as suitable to receive treatment, if the albumin uptake level (or levels of one or more biomarkers described herein) for that individual is in about the top 80% of albumin uptake level (or levels of one or more biomarkers described herein) for that population (conversely, individuals are generally not suitable to receive treatment if they are in about the bottom 20% of albumin uptake level (or levels of one or more biomarkers described herein) for that population). In other embodiments, an individual is included in treatment, or identified as suitable to receive treatment, if the albumin uptake level (or levels of one or more biomarkers described herein) for that individual is in about the top 50% for that population (conversely, individuals are generally not suitable to receive treatment if they are in about the bottom 50% of albumin uptake level (or levels of one or more biomarkers described herein) for that population). In some embodiments, the albumin uptake level (or levels of one or more biomarkers described herein) in that individual (for example an individual who is responsive or suitable for treatment) is in about any of the top percentages: 30%; 25%; 20%; 10%; 5%. A population may be about, or alternatively at least about any of the following, in terms of number of individuals measured: 10, 15, 20, 25, 30, 50, 60, 75, 100, 125, 150, 175, 200, 225, 250, 300, 400, 500. Preferably, a sufficient number of individuals are measured to provide a statistically significant population, which can be determined by methods known in the art. An upper limit of a population may be any number, including those listed.

Methods of Treating Prostate Cancer

The present invention provides methods of treating prostate cancer in an individual (e.g., human) comprising administering to the individual a) an effective amount of a composition comprising nanoparticles comprising docetaxel and an albumin; and b) an effective amount of a steroid (e.g., prednisone). The present invention provides methods of treating prostate cancer in an individual (e.g., human) comprising administering to the individual a) an effective amount of a composition comprising nanoparticles comprising docetaxel and an albumin; and b) an effective amount of a steroid (e.g., prednisone). In some embodiments, there is provided a method of treating prostate cancer in an individual (e.g., human) comprising administering to the individual a) an effective amount of a composition comprising nanoparticles comprising docetaxel coated with an albumin; and b) an effective amount of a steroid (e.g., prednisone). In some embodiments, there is provided a method of treating prostate cancer in an individual (e.g., human) comprising administering to the individual a) an effective amount of a composition comprising nanoparticles comprising docetaxel and an albumin, wherein the average size of the nanoparticles in the nanoparticle composition is no greater than about 200 nm; and b) an effective amount of a steroid (e.g., prednisone). In some embodiments, there is provided a method of treating prostate cancer in an individual (e.g., human) comprising administering to the individual a) an effective amount of a composition comprising nanoparticles comprising docetaxel coated with albumin, wherein the average size of the nanoparticles in the nanoparticle composition is no greater than about 200 nm; and b) an effective amount of a steroid (e.g., prednisone). In some embodiments, there is provided a method of treating prostate cancer in an individual (e.g., human) comprising administering to the individual a) an effective amount of Nab-docetaxel, wherein the average size of the nanoparticles in the nanoparticle composition is no greater than about 200 nm; and b) an effective amount of a steroid (e.g., prednisone).

Also provided are methods of treating prostate cancer in an individual comprising administering to the individual a) an effective amount of a composition comprising nanoparticles comprising docetaxel and an albumin and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of a composition comprising nanoparticles comprising docetaxel coated with albumin and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of a composition comprising nanoparticles comprising docetaxel and an albumin, wherein the average size of the nanoparticles in the nanoparticle composition is no greater than about 200 nm, and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of a composition comprising nanoparticles comprising docetaxel coated with albumin, wherein the average size of the nanoparticles in the nanoparticle composition is no greater than about 200 nm, and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of Nab-docetaxel, and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake.

Provided herein are also methods of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel and an albumin and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel coated with an albumin and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel and an albumin, wherein the average size of the nanoparticles in the nanoparticle composition is no greater than about 200 nm, and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel coated with albumin, wherein the average size of the nanoparticles in the nanoparticle composition is no greater than about 200 nm, and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of Nab-docetaxel, and ii) an effective amount of a steroid.

In some embodiments of any of the methods, the one or more characteristics of prostate cancer include 1, 2, 3, 4, or 5 characteristics of prostate cancer. In some embodiments, the one or more characteristics include, for example, at least two or more characteristics, at least three or more characteristics, or at least four or more characteristics. For example, in some embodiments, the prostate cancer is characterized by differential levels of CAV-1. In some embodiments, the prostate cancer is characterized by differential levels of CAV-1 and gp60. In some embodiments, the prostate cancer is characterized by differential levels of caveolin-1 (CAV1), differential levels of SPARC, differential levels of gp60, and differential albumin uptake.

In some embodiments of any of the methods, the prostate cancer is an adenocarcinoma. In some embodiments, the prostate cancer is a sarcoma, neuroendocrine tumor, small cell cancer, ductal cancer, or a lymphoma. There are provided methods of treating prostate cancer at any of the four stages, A, B, C, or D, according to the Jewett staging system. In some embodiments, the prostate cancer is stage A prostate cancer (The cancer cannot be felt during a rectal exam.). In some embodiments, the prostate cancer is stage B prostate cancer (The tumor involves more tissue within the prostate, it can be felt during a rectal exam, or it is found with a biopsy that is done because of a high PSA level.). In some embodiments, the prostate cancer is stage C prostate cancer (The cancer has spread outside the prostate to nearby tissues.). In some embodiments, the prostate cancer is stage D prostate cancer.

In some embodiments of any of the methods, the prostate cancer may be androgen independent prostate cancer (AIPC). In some embodiments, the prostate cancer may be androgen dependent prostate cancer. In some embodiments, the prostate cancer may be refractory to hormone therapy. In some embodiments, the prostate cancer may be substantially refractory to hormone therapy. In some embodiments, the individual may be a human who has a gene, genetic mutation, or polymorphism associated with prostate cancer (e.g., RNASEL/HPC1, ELAC2/HPC2, SR-A/MSR1, CHEK2, BRCA2, PON1, OGG1, MIC-1, TLR4, and/or PTEN) or has one or more extra copies of a gene associated with prostate cancer.

In some embodiments of any of the methods described herein, the prostate cancer is early stage prostate cancer, non-metastatic prostate cancer, primary prostate cancer, advanced prostate cancer, locally advanced prostate cancer, metastatic prostate cancer, prostate cancer in remission, or recurrent prostate cancer. In some embodiments, the prostate cancer is localized resectable, localized unresectable, or unresectable. The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first-line therapy. In some embodiments, the method is used as a second-line therapy.

In some embodiments of any of the methods described herein, the composition comprises nanoparticles comprising docetaxel and an albumin (such as human serum albumin), wherein docetaxel in the nanoparticles is coated with the albumin. In some embodiments, the average particle size of the nanoparticles in the composition is no greater than about 200 nm (such as less than about 200 nm). In some embodiments, the composition comprises Nab-docetaxel. In some embodiments, the composition is the Nab-docetaxel. In some embodiments, the docetaxel nanoparticle composition and the steroid have synergistic effect on treating prostate cancer. In some embodiments, the steroid is prednisone.

In some embodiments of any of the methods described herein, the effective amount of a composition comprising nanoparticles comprising docetaxel and the albumin is between about 30 mg/m$^2$ to about 200 mg/m$^2$ (e.g., 60 mg/m$^2$, 75 mg/m$^2$, or 100 mg/m$^2$) and the effective amount of the steroid is between about 2.5 mg to about 20 mg (e.g., 2.5 mg, 5 mg, or 10 mg). In some embodiments of any of the methods described herein, the effective amount of the composition comprising nanoparticles comprising docetaxel and the albumin is administered once every three weeks and the effective amount of the steroid is administered twice daily. In some embodiments, the effective amount of the composition comprising nanoparticles comprising docetaxel and the albumin is between about 30 to about 200 mg/m$^2$ administered once every three weeks and the effective amount of the steroid is between about 2.5 mg to about 20 mg administered twice daily. In some embodiments, the effective amount of the composition comprising nanoparticles comprising docetaxel and the albumin is about 75 mg/m² administered once every three weeks and the effective amount of a steroid is about 5 mg administered twice daily. In some embodiments, the docetaxel nanoparticle composition is administered intravenously. In some embodiments, the steroid is administered orally. In some embodiments, the composition comprising nanoparticles comprising docetaxel and the albumin and the steroid are sequentially administered; concurrently administered or simultaneously administered.

Thus, for example, in some embodiments, there is provided a method of treating prostate cancer in an individual, comprising administering to the individual: a) between about 30 mg/m² to about 200 mg/m² (e.g., 60 mg/m², 75 mg/m², or 100 mg/m²) nanoparticles comprising docetaxel and an albumin (such as nanoparticles comprising docetaxel coated with albumin, for example Nab-docetaxel) and b) between about 2.5 mg to about 20 mg (e.g., 2.5 mg, 5 mg, or 10 mg) of a steroid (such as prednisone). In some embodiments, there is provided a method of treating prostate cancer in an individual, comprising administering to the individual: a) between about 30 mg/m² to about 200 mg/m² (e.g., 60 mg/m², 75 mg/m², or 100 mg/m²) nanoparticles comprising docetaxel and an albumin (such as nanoparticles comprising docetaxel coated with albumin, for example Nab-docetaxel) once every three weeks, and b) between about 2.5 mg to about 20 mg (e.g., 2.5 mg, 5 mg, or 10 mg) of a steroid (such as prednisone) twice daily. In some embodiments, there is provided a method of treating prostate cancer in an individual, comprising administering to the individual: a) between about 30 mg/m² to about 200 mg/m² (e.g., 60 mg/m², 75 mg/m², or 100 mg/m²) nanoparticles comprising docetaxel and an albumin (such as nanoparticles comprising docetaxel coated with albumin, for example Nab-docetaxel) once every three weeks intravenously, and b) between about 2.5 mg to about 20 mg (e.g., 2.5 mg, 5 mg, or 10 mg) of a steroid (such as prednisone) twice daily orally.

In some embodiments of any of the methods described herein, an individual (e.g., human) who has been diagnosed with or is suspected of having prostate cancer can be treated. In some embodiments, the individual is human. In some embodiments, the individual is at least about any of 35, 40, 45, 50, 55, 60, 65, 70, 75, 80, or 85 years old. In some embodiments, the individual is male. In some embodiments, the individual has any of the types of prostate cancer described herein. In some embodiments, the individual has a single lesion at presentation. In some embodiments, the individual has multiple lesions at presentation. In some embodiments, the individual is resistant to treatment of prostate cancer with other agents (such as a non-nanoparticle formulation of taxane, e.g., Taxol® or Taxotere®). In some embodiments, the individual is initially responsive to treatment of prostate cancer with other agents (such as a non-nanoparticle formulation of taxane, e.g., Taxol® or Taxotere®) but has progressed after treatment.

In some embodiments, a lower amount of each pharmaceutically active compound is used as part of a combination therapy compared to the amount generally used for individual therapy. In some embodiments, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. For example, the use of a small amount of pharmaceutically active compound may result in a reduction in the number, severity, frequency, or duration of one or more side-effects associated with the compound.

The methods described herein can be used for any one or more of the following purposes: alleviating one or more symptoms of prostate cancer, delaying progressing of prostate cancer, shrinking tumor size in prostate cancer patient, inhibiting prostate cancer tumor growth, prolonging overall survival, prolonging progression free survival, preventing or delaying prostate cancer tumor metastasis, reducing (such as eradiating) preexisting prostate cancer tumor metastasis, reducing incidence or burden of preexisting prostate cancer tumor metastasis, or preventing recurrence of prostate cancer.

It is to be understood that the methods described in other sections of the present application, such as methods of treatment and enhancing drug uptake and methods of treatment based drug uptake capability, also apply to methods described herein.

Nanoparticle Compositions

The nanoparticle compositions described herein comprise nanoparticles comprising (in various embodiments consisting essentially of) a poorly water insoluble drug (such as a taxane, including paclitaxel or docetaxel) and an albumin (such as human serum albumin) Nanoparticles of poorly water soluble drugs (such as a taxane) have been disclosed in, for example, U.S. Pat. Nos. 5,916,596; 6,506,405; 6,749,868, and 6,537,579 and also in U.S. Pat. Pub. Nos. 2005/0004002, 2006/0263434, and 2007/0082838; PCT Patent Application WO08/137,148, each of which is incorporated by reference in their entirety. In some embodiments, the poorly water insoluble drug is a taxane (such as paclitaxel or docetaxel). In some embodiments, the poorly water insoluble drug is rapamycin. Nanoparticles compositions comprising albumin and rapamycin and uses thereof for the treatment of diseases are described, for example, at PCT Application Publication No. WO08/109,163, which is incorporated herein in its entirely. It is understood that descriptions herein about a taxane nanoparticle composition applies equally to a composition comprising nanoparticles comprising rapamycin, or a rapamycin nanoparticle composition.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 to about 400 nm, including for example about 20 to about 200 nm, about 40 to about 200 nm, about 30 to about 180 nm, and any one of about 40 to about 150, about 50 to about 120, and about 60 to about 100 nm.

In some embodiments, the albumin has sulfhydral groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprise the taxane (such as paclitaxel) coated with an albumin (e.g., human serum albumin). In some embodiments, the composition comprises taxane in both nanoparticle and non-nanoparticle forms, wherein at least about any one of 50%, 60%, 70%, 80%, 90%, 95%, or 99% of the taxane in the composition are in nanoparticle form. In some embodiments, the taxane in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of taxane that is substantially free of polymeric materials (such as polymeric matrix).

In some embodiments, the composition comprises albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of albumin (such as human serum albumin) and taxane in the taxane nanoparticle composition is about 18:1 or less, such as about 15:1 or less, for example about 10:1 or less. In some embodiments, the weight ratio of albumin (such as human serum albumin) and taxane in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of albumin and taxane in the nanoparticle portion of the composition is about any one of 1:2, 1:3, 1:4, 1:5, 1:10, 1:15, or less. In some embodiments, the weight ratio of the albumin (such as human serum albumin) and the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the taxane nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises human serum albumin. Other albumins are contemplated, such as bovine serum albumin Use of such non-human albumins could be appropriate, for example, in the context of use of these compositions in non-human mammals, such as the veterinary (including domestic pets and agricultural context).

The albumin (such as human serum albumin) in the composition generally serves as a carrier for the taxane, i.e., the albumin in the composition makes the taxane more readily suspendable in an aqueous medium or helps maintain the suspension as compared to compositions not comprising an albumin. This can avoid the use of toxic solvents (or surfactants) for solubilizing the taxane, and thereby can reduce one or more side effects of administration of the taxane into an individual (such as a human). Thus, in some embodiments, the composition described herein is substantially free (such as free) of surfactants, such as Cremophor (including Cremophor EL® (BASF)). In some embodiments, the taxane nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the taxane nanoparticle composition is administered to the individual. In some embodiments, the taxane nanoparticle composition contains less than about any one of 20%, 15%, 10%, 7.5%, 5%, 2.5%, or 1% organic solvent or surfactant.

The amount of albumin in the composition described herein will vary depending on other components in the composition. In some embodiments, the composition comprises an albumin in an amount that is sufficient to stabilize the taxane in an aqueous suspension, for example, in the form of a stable colloidal suspension (such as a stable suspension of nanoparticles). In some embodiments, the albumin is in an amount that reduces the sedimentation rate of the taxane in an aqueous medium. For particle-containing compositions, the amount of the albumin also depends on the size and density of nanoparticles of the taxane.

A taxane is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize the taxane in an aqueous suspension at a certain concentration. For example, the concentration of the taxane in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the taxane is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of albumin. In some embodiments, the composition, in liquid form, comprises about 0.5% to about 5% (w/v) of albumin.

In some embodiments, the weight ratio of albumin, e.g., albumin, to the taxane in the taxane nanoparticle composition is such that a sufficient amount of taxane binds to, or is transported by, the cell. While the weight ratio of albumin to taxane will have to be optimized for different albumin and taxane combinations, generally the weight ratio of albumin, e.g., albumin, to taxane (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to taxane weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human serum albumin) and the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the albumin allows the composition to be administered to an individual (such as human) without significant side effects. In some embodiments, the albumin (such as human serum albumin) is in an amount that is effective to reduce one or more side effects of administration of the taxane to a human. The term "reducing one or more side effects of administration of the taxane" refers to reduction, alleviation, elimination, or avoidance of one or more undesirable effects caused by the taxane, as well as side effects caused by delivery vehicles (such as solvents that render the taxanes suitable for injection) used to deliver the taxane. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with taxanes can be reduced.

In some embodiments, the taxane nanoparticle composition comprises Abraxane® (Nab-paclitaxel). In some embodiments, the taxane nanoparticle composition is Abraxane® (Nab-paclitaxel). Abraxane® is a formulation of paclitaxel stabilized by human albumin USP, which can be dispersed in directly injectable physiological solution. When dispersed in a suitable aqueous medium such as 0.9% sodium chloride injection or 5% dextrose injection, Abraxane® forms a stable colloidal suspension of paclitaxel. The mean particle size of the nanoparticles in the colloidal suspension is about 130 nanometers. Since HSA is freely soluble in water, Abraxane® can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml.

Methods of making nanoparticle compositions are known in the art. For example, nanoparticles containing taxanes (such as paclitaxel) and albumin (such as human serum albumin) can be prepared under conditions of high shear forces (e.g., sonication, high pressure homogenization, or the like). These methods are disclosed in, for example, U.S. Pat. Nos. 5,916,596; 6,506,405; 6,749,868, and 6,537,579 and also in U.S. Pat. Pub. No. 2005/0004002, 2007/0082838, 2006/0263434 and PCT Application WO08/137,148.

Briefly, the taxane (such as paclitaxel) is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1.

Therapeutic Agents

In some embodiments, the therapeutic agent is a chemotherapeutic agent, including (and in some embodiments selected from the group consisting of) antimetabolites (including nucleoside analogs, such as gemcitabine), platinum-based agents (such as carboplatin or cisplatin), alkylating agents, tyrosine kinase inhibitors, anthracycline antibiotics, vinca alkloids, proteasome inhibitors, macrolides, and topoisomerase inhibitors. In some embodiments, the therapeutic agent is a platinum-based agent, such as carboplatin.

In some embodiments, the therapeutic agent is an agent that specifically target to a cell (a targeted agent). Suitable agents include, for example, antibodies recognizing specific cellular receptors, kinase inhibitors, or molecules targeted to specific cellular receptors or proteins, for example a hedgehog inhibitor.

In some embodiments, the therapeutic agent is gemcitabine. In some embodiments, the therapeutic agent is not gemcitabine. In some embodiments, the target tissue is difficult to penetrate by gemcitabine. In some embodiments, the target tissue is a pancreatic cancer tissue. In some embodiments, the target tissue is not a pancreatic tissue. In some embodiments, the therapeutic agent is a platinum-based agent (such as carboplatin, cisplatin, or oxaliplatin). In some embodiments, the therapeutic agent is not a platinum-based agent. In some embodiments, the target tissue is difficult to penetrate by a platinum-based agent. In some embodiments, the target tissue is a lung cancer tissue (such as a squamous NSCLC tissue). In some embodiments, the target tissue is not a lung cancer tissue. Other therapeutic agents suitable for use in methods described herein include those described in US Patent Application Publication No. 2006/0263434, the entire content of which is incorporated herein by reference.

Modes of Administration

The methods described herein in some embodiments comprise co-administration of a taxane nanoparticle composition comprising albumin and a taxane and a therapeutic agent.

In some embodiments, the taxane nanoparticle composition and the therapeutic agent (including the specific therapeutic agents described herein) are administered simultaneously. When the drugs are administered simultaneously, the drug in the nanoparticles and the therapeutic agent may be contained in the same composition (e.g., a composition comprising both the nanoparticles and the therapeutic agent) or in separate compositions (e.g., the nanoparticles are contained in one composition and the therapeutic agent is contained in another composition).

In some embodiments, the taxane nanoparticle composition and the therapeutic agent are administered sequentially. Either the taxane nanoparticle composition or the therapeutic agent may be administered first. The taxane nanoparticle composition and the therapeutic agent are contained in separate compositions, which may be contained in the same or different packages.

In some embodiments, the administration of the taxane nanoparticle composition and the therapeutic agent are concurrent, i.e., the administration period of the taxane nanoparticle composition and that of the therapeutic agent overlap with each other. In some embodiments, the taxane nanoparticle composition is administered for at least one cycle (for example, at least any of 2, 3, or 4 cycles) prior to the administration of the therapeutic agent. In some embodiments, the therapeutic agent is administered for at least any of one, two, three, or four weeks. In some embodiments, the administrations of the taxane nanoparticle composition and the therapeutic agent are initiated at about the same time (for example, within any one of 1, 2, 3, 4, 5, 6, or 7 days). In some embodiments, the administrations of the taxane nanoparticle composition and the therapeutic agent are terminated at about the same time (for example, within any one of 1, 2, 3, 4, 5, 6, or 7 days). In some embodiments, the administration of the therapeutic agent continues (for example for about any one of 1, 2, 3, 4, 5, 6, 7, 8, 9, 10, 11, or 12 months) after the termination of the administration of the taxane nanoparticle composition. In some embodiments, the administration of the therapeutic agent is initiated after (for example after about any one of 1, 2, 3, 4, 5, 6, 7, 8, 9, 10, 11, or we months) the initiation of the administration of the taxane nanoparticle composition. In some embodiments, the administrations of the taxane nanoparticle composition and the therapeutic agent are initiated and terminated at about the same time. In some embodiments, the administrations of the taxane nanoparticle composition and the therapeutic agent are initiated at about the same time and the administration of the therapeutic agent continues (for example for about any one of 1, 2, 3, 4, 5, 6, 7, 8, 9, 10, 11, or 12 months) after the termination of the administration of the taxane nanoparticle composition. In some embodiments, the administration of the taxane nanoparticle composition and the therapeutic agent stop at about the same time and the administration of the therapeutic agent is initiated after (for example after about any one of 1, 2, 3, 4, 5, 6, 7, 8, 9, 10, 11, or we months) the initiation of the administration of the taxane nanoparticle composition.

In some embodiments, the administration of the taxane nanoparticle composition and the therapeutic agent are non-concurrent. For example, in some embodiments, the administration of the taxane nanoparticle composition is terminated before the therapeutic agent is administered. In some embodiments, the administration of the therapeutic agent is terminated before the taxane nanoparticle composition is administered. The time period between these two non-concurrent administrations can range from about two to eight weeks, such as about four weeks.

The dosing frequency of the drug-containing nanoparticle composition and the therapeutic agent may be adjusted over the course of the treatment, based on the judgment of the administering physician. When administered separately, the drug-containing nanoparticle composition and the therapeutic agent can be administered at different dosing frequency or intervals. For example, the drug-containing nanoparticle composition can be administered weekly or once every three weeks, while a therapeutic agent can be administered more or less frequently. In some embodiments, sustained continuous release formulation of the drug-containing nanoparticle and/or therapeutic agent may be used. Various formulations and devices for achieving sustained release are known in the art. A combination of the administration configurations described herein can also be used.

The taxane nanoparticle composition and the therapeutic agent can be administered using the same route of administration or different routes of administration. In some embodiments (for both simultaneous and sequential administrations), the taxane in the taxane nanoparticle composition and the therapeutic agent are administered at a predetermined ratio. For example, in some embodiments, the ratio by weight of the taxane in the taxane nanoparticle composition and the therapeutic agent is about 1 to 1. In some embodiments, the weight ratio may be between about 0.001 to about 1 and about 1000 to about 1, or between about 0.01 to about 1 and 100 to about 1. In some embodiments, the ratio by weight of the taxane in the taxane nanoparticle composition and the therapeutic agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the taxane in the taxane nanoparticle composition and the therapeutic agent is more than about any of 1:1, 2:1, 3:1, 4:1, 5:1, 6:1, 7:1, 8:1, 9:1, 30:1, 50:1, 100:1. Other ratios are contemplated.

Thus, in some embodiments, a subtherapeutic amount of the drug in the taxane nanoparticle composition and/or the therapeutic agent is administered.

In some embodiments, the dose of the taxane in the taxane nanoparticle composition is non-cytotoxic. Cytotoxicity can be measured, for example, by one or more methods described herein. Noncytoxic amount can be determined based on an in vitro cell viability assay. The noncytotoxic amount can be an amount that is insufficient to cause about 50% or more cell death in an in vitro cell viability assay. In some embodiments, the amount of the taxane in the taxane nanoparticle composition is insufficient to cause about any of 40% or more, 30% or more, 20% or more, 10% or more, 5% or more, 4% or more, 3% or more, 2% or more, or 1% or more cell death in an in vitro cell viability assay. In some embodiments, the amount of taxane in the taxane nanoparticle composition is insufficient to cause any measurable cell death in an in vitro cell viability assay. Noncytotoxic amount can also be determined based on in vivo assay of drug toxicity. For example, the noncytotoxic amount can be an amount that is insufficient to kill about 50% or more of the test population in in vivo cytotoxicity assays. In some embodiments, the amount of the taxane in the taxane nanoparticle composition is insufficient to kill about any of 40% or more, 30% or more, 20% or more, 10% or more, 5% or more, 4% or more, 3% or more, 2% or more, or 1% or more test population in an in vivo cytotoxicity assay. In some embodiments, the amount of the composition is insufficient to cause any death in a test population in an in vivo drug toxicity assay. Noncytotoxic amount can also be determined based on the amount of taxane that is required to induce apparent systemic toxicity (such as weight loss) in an individual, that is, the amount of the drug is noncytotoxic if it does not induce any apparent systemic toxicity. For example, in some embodiments, a noncytotoxic amount is an amount that induces less than about 15% (including for example less than about any of 10%, 8%, 5%, or less) of weight loss.

In some embodiments, the dose of both the taxane in the taxane nanoparticle composition and the therapeutic agent are reduced as compared to the corresponding normal dose of each when administered alone. In some embodiments, both the taxane in the taxane nanoparticle composition and the therapeutic agent are administered at a subtherapeutic, i.e., reduced, level. In some embodiments, the dose of the taxane nanoparticle composition and/or the therapeutic agent is substantially less than the established maximum toxic dose (MTD). For example, the dose of the taxane nanoparticle composition and/or the therapeutic agent is less than about 50%, 40%, 30%, 20%, or 10% of the MTD.

A combination of the administration configurations described herein can be used. The combination therapy methods described herein may be performed alone or in conjunction with another therapy, such as chemotherapy, radiation therapy, surgery, hormone therapy, gene therapy, immunotherapy, chemoimmunotherapy, hepatic artery-based therapy, cryotherapy, ultrasound therapy, liver transplantation, local ablative therapy, radiofrequency ablation therapy, photodynamic therapy, and the like.

The therapeutic agent described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. In some embodiments, the therapeutic agent is administrated intravenously. In some embodiments, the taxane nanoparticle composition is administered orally.

Exemplary dosing for the taxane (e.g., paclitaxel) in the composition include any of the following ranges: about 0.1 mg to about 500 mg, about 0.1 mg to about 2.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) in the effective amount of the composition (e.g., a unit dosage form) is in the range of about 5 mg to about 500 mg, such as about 30 mg to about 300 mg or about 50 mg to about 200 mg. In some embodiments, the concentration of the taxane (e.g., paclitaxel) in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the taxane (e.g., paclitaxel) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of a taxane (e.g., paclitaxel) in the nanoparticle composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of a taxane (e.g., paclitaxel). In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a taxane (e.g., paclitaxel). In some embodiments, the amount of the taxane (e.g., paclitaxel) per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a taxane (e.g., paclitaxel) in the composition is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a taxane (e.g., paclitaxel) in the composition is about 5 to about 300 mg/m$^2$, such as about 100 to about 150 mg/m$^2$, about 120 mg/m$^2$, about 130 mg/m$^2$, or about 140 mg/m$^2$.

In some embodiments of any of the above aspects, the effective amount of a taxane (e.g., paclitaxel) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of a taxane (e.g., paclitaxel) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a taxane (e.g., paclitaxel).

Exemplary dosing frequencies for the administration of the nanoparticle compositions include, but are not limited to, daily, every two days, every three days, every four days, every five days, every six days, weekly without break, three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, the taxane (e.g., paclitaxel) is administered over a period of at least ten days, wherein the interval between each administration is no more than about two days, and wherein the dose of the taxane (e.g., paclitaxel) at each administration is about 0.25 mg/m² to about 250 mg/m², about 0.25 mg/m² to about 150 mg/m², about 0.25 mg/m² to about 75 mg/m², such as about 0.25 mg/m² to about 25 mg/m², or about 25 mg/m² to about 50 mg/m².

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the dosage of a taxane (e.g., paclitaxel) in a nanoparticle composition can be in the range of 5-400 mg/m² when given on a 3 week schedule, or 5-250 mg/m² (such as 80-150 mg/m², for example 100-120 mg/m²) when given on a weekly schedule. For example, the amount of a taxane (e.g., paclitaxel) is about 60 to about 300 mg/m² (e.g., about 260 mg/m²) on a three week schedule.

Other exemplary dosing schedules for the administration of the nanoparticle composition (e.g., paclitaxel/albumin nanoparticle composition) include, but are not limited to, 100 mg/m², weekly, without break; 75 mg/m² weekly, 3 out of four weeks; 100 mg/m², weekly, 3 out of 4 weeks; 125 mg/m², weekly, 3 out of 4 weeks; 125 mg/m², weekly, 2 out of 3 weeks; 130 mg/m², weekly, without break; 175 mg/m², once every 2 weeks; 260 mg/m², once every 2 weeks; 260 mg/m², once every 3 weeks; 180-300 mg/m², every three weeks; 60-175 mg/m², weekly, without break; 20-150 mg/m² twice a week; and 150-250 mg/m² twice a week. The dosing frequency of the composition may be adjusted over the course of the treatment based on the judgment of the administering physician.

In some embodiments, the individual is treated for at least about any of one, two, three, four, five, six, seven, eight, nine, or ten treatment cycles.

The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or minutes. In some embodiments, the composition is administered over an infusion period of about 30 minutes.

Other exemplary dose of the taxane (in some embodiments paclitaxel) in the nanoparticle composition include, but is not limited to, about any of 50 mg/m², 60 mg/m², 75 mg/m², 80 mg/m², 90 mg/m², 100 mg/m², 120 mg/m², 160 mg/m², 175 mg/m², 200 mg/m², 210 mg/m², 220 mg/m², 260 mg/m², and 300 mg/m². For example, the dosage of paclitaxel in a nanoparticle composition can be in the range of about 100-400 mg/m² when given on a 3 week schedule, or about 50-250 mg/m² when given on a weekly schedule.

The dosing frequency of the therapeutic agent can be the same or different from that of the taxane nanoparticle composition. For example, the therapeutic agent can be administered three times a day, two times a day, daily, 6 times a week, 5 times a week, 4 times a week, 3 times a week, two times a week, weekly. In some embodiments, the therapeutic agent is administered twice daily or three times daily. Exemplary amounts of the therapeutic agent include, but are not limited to, any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. For example, the therapeutic agent can be administered at a dose of about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). For example, in some embodiments, STMN1 inhibitor is administered at about 1-100 mg/kg (including for example 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg), every two days for five times.

In some embodiments, the effective amount of taxane in the taxane nanoparticle composition is between about 45 mg/m² to about 350 mg/m² and the effective amount of the therapeutic agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the taxane nanoparticle composition is between about 80 mg/m² to about 350 mg/m² and the effective amount of the therapeutic agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the taxane nanoparticle composition is between about 80 mg/m² to about 300 mg/m² and the effective amount of the therapeutic agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the taxane nanoparticle composition is between about 150 mg/m² to about 350 mg/m² and the effective amount of the therapeutic agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the taxane nanoparticle composition is between about 80 mg/m² to about 150 mg/m² and the effective amount of the therapeutic agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the taxane nanoparticle composition is about 100 mg/m². In some embodiments, the effective amount of taxane in the taxane nanoparticle composition is between about 170 mg/m² to about 200 mg/m² and the effective amount of the therapeutic agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the taxane nanoparticle composition is between about 200 mg/m² to about 350 mg/m² and the effective amount of the therapeutic agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the taxane nanoparticle composition is about 260 mg/m². In some embodiments of any of the above methods, the effective amount of the therapeutic agent is about 20-30 mg/kg, about 30-40 mg/kg, about 40-50 mg/kg, about 50-60 mg/kg, about 60-70 mg/kg, about 70-80 mg/kg, about 80-100 mg/kg, or about 100-120 mg/kg.

In some embodiments, the appropriate doses of therapeutic agents are approximately those already employed in clinical therapies wherein the therapeutic agent are administered alone or in combination with therapeutic agents.

Kits, Articles of Manufacture, and Method of Marketing

The present application also provides kits and articles of manufacture that are useful for methods described herein.

In some embodiments, there is provided a kit comprising 1) a composition comprising nanoparticles comprising albumin and a taxane, and 2) an instruction for using said composition for a method of facilitating delivery of a therapeutic agent. In some embodiments, there is provided a kit comprising 1) a composition comprising nanoparticles comprising albumin and a taxane, and 2) an instruction for using said composition for a method of creating a favorable tissue microenvironment for the delivery of a therapeutic agent. In some embodiments, the kit further comprises the therapeutic agent.

In some embodiments, there is provided a kit comprising 1) a composition comprising nanoparticles comprising albumin and a taxane, and 2) a therapeutic agent, and c) an instruction for selecting a patient based on drug uptake capability.

In some embodiments, there is provided a kit comprising 1) a composition comprising nanoparticles comprising albumin and a taxane, and 2) an agent for determining drug uptake capability of a target tissue in an individual. In some embodiments, the kit further comprises an instruction for selecting a patient based on the drug uptake capability.

In some embodiments, there is provided an article of manufacture comprising, packaged together, a) a composition comprising nanoparticles comprising albumin and a taxane, b) a therapeutic agent, and c) a label denoting (i.e., indicating) that the composition and the therapeutic agent are indicated for treating individuals having cancer with one or more characteristics that is indicative of a higher likelihood of enhanced delivery of the therapeutic agent (such as a characteristics selected from the group consisting of: increased albumin uptake in the tumor tissue, increased levels of caveolin-1 in the tumor tissue, increased level of gp60 in the tumor tissue, increased level of SPARC in the tumor tissue).

In some embodiments, there is provided a method of marketing a combination therapy comprising: a) a composition comprising nanoparticles comprising albumin and a taxane and b) a therapeutic agent for use in an individual subpopulation, the method comprising informing a targeted audience about the use of the combination therapy for treating the individual subpopulation having cancer with one or more characteristics that is indicative of a higher likelihood of enhanced delivery of the therapeutic agent (such as a characteristics selected from the group consisting of: increased albumin uptake in the tumor tissue, increased levels of caveolin-1 in the tumor tissue, increased level of gp60 in the tumor tissue, increased level of SPARC in the tumor tissue).

Exemplary Embodiments

The present application in some embodiments, provides a method of treating a disease in an individual, comprising administering to the individual an effective amount of a therapeutic agent and a composition comprising nanoparticles comprising albumin and a taxane, wherein the uptake of the therapeutic agent to a target tissue is enhanced compared to the uptake of the therapeutic agent not co-administered with the taxane nanoparticle composition. In some embodiments, the disease is cancer. In some embodiments, the target tissue is tumor (such as solid tumor).

In some embodiments, there is provided a method of facilitating the uptake of a therapeutic agent to a target tissue in an individual, comprising administering to the individual the therapeutic agent in conjunction with a composition comprising nanoparticles comprising an albumin and a taxane. In some embodiments, the target tissue is a tumor (such as solid tumor).

In some embodiments, there is provided a method of altering the microenvironment of a target tissue to facilitate access of a therapeutic agent, comprising administering to the individual a composition comprising nanoparticles comprising albumin and a taxane. In some embodiments, the target tissue is a tumor (such as a solid tumor). In some embodiments, the tumor stroma is reduced compared to individual not administered with the nanoparticle composition. In some embodiments, the tumor vascularization is increased compared to individual not administered with the nanoparticle composition. In some embodiments, the cell/vessel proximity in the tumor is increased compared to individual not administered with the nanoparticle composition.

In some embodiments according to any one of the methods described above in the present section, the method further comprises administering an effective amount of a therapeutic agent.

In some embodiments according to any one of the methods described above in the present section, the target tissue in the individual has any one or more of the following characteristics: 1) increased albumin uptake; 2) increased caveolin-1 expression; 3) increased gp60 expression; and 4) increased SPARC expression.

In some embodiments, there is provided a method of treating a disease in an individual, comprising administering to the individual: (a) an effective amount of a composition comprising nanoparticles comprising albumin and a taxane, and (b) an effective amount of a therapeutic agent, wherein drug uptake capability is used as a basis for selecting the individual to receive treatment.

In some embodiments, there is provided a method of treating a disease in an individual, comprising: (a) determining the drug uptake capability of the target tissue in the individual, and (b) administering to the individual: (1) an effective amount of a composition comprising nanoparticles comprising albumin and a taxane, and (2) a therapeutic agent.

In some embodiments, there is provided a method of identifying an individual suitable for treatment of a disease comprising administering (a) an effective amount of a composition comprising nanoparticles comprising albumin and a taxane, and (b) an effective amount of a therapeutic agent, wherein the individual is identified as being suitable for treatment if the individual has a drug uptake capability in the target tissue. In some embodiments, the method further comprises administering the effective amount of a composition comprising nanoparticles comprising albumin and a taxane and a therapeutic agent to the individual.

In some embodiments, there is provided a method of assessing responsiveness of an individual to a treatment of a diseases comprising administration of (a) an effective amount of a composition comprising nanoparticles comprising albumin and a taxane and (b) an effective amount of a therapeutic agent, the method comprising determining drug uptake capability of the target tissue in the individual, wherein a drug uptake capability is indicative that the individual is responsive to the treatment. In some embodiments, the method further comprises administering the effective amount of a composition comprising nanoparticles comprising albumin and a taxane and a therapeutic agent to the individual.

In some embodiments according to any one of the methods described in the present section that involves drug uptake capability, wherein drug uptake capability is determined based on one or more characteristics selected from the group consisting of: (a) high level of albumin uptake; (b) high level of caveolin-1 expression; (c) high level of gp-60 expression; and (d) high level of SPARC expression. In some embodiments according to any one of the methods described in the present section, the taxane is paclitaxel. In some embodiments, the taxane is docetaxel.

In some embodiments according to any one of the methods described in the present section, the nanoparticles in the taxane nanoparticle composition have an average particle size of less than about 200 nm.

In some embodiments according to any one of the methods described in the present section, the nanoparticles in the taxane nanoparticle composition comprises a taxane coated with albumin.

In some embodiments according to any one of the methods described in the present section, the therapeutic agent is selected from the group consisting of: an antimetabolite, a platinum-based agent, and a prednisone.

In some embodiments according to any one of the methods described in the present section that involves a disease, the disease is a pancreatic cancer, lung cancer, or melanoma. In some embodiments, the disease is squamous cell carcinoma. In some embodiments, the disease is squamous NSCLC.

In some embodiments, there is provided a method of treating a cancer that is highly fibrotic and/or has a dense stroma in an individual, comprising administering to the individual a) an effective amount of a composition comprising nanoparticles comprising a taxane and an albumin. In some embodiments, the cancer is a pancreatic cancer, lung cancer, melanoma, or prostate cancer. In some embodiments, the cancer is selected from the group consisting of: squamous cell carcinomas, mesothelioma, desmoplastic fibroma, desmoplastic round cell tumor, colorectal carcinoma and tumors of gastrointestinal tract. In some embodiments, the method further comprises administering another therapeutic agent. In some embodiments, the individual is not responsive to the treatment of the composition comprising nanoparticles comprising the taxane and the albumin when administered alone and/or the individual is not responsive to the treatment of the therapeutic agent when administered alone. In some embodiments, the method comprises assessing one or more of the following in the individual prior to administering the taxane nanoparticle composition: a) the amount of tissue stroma, b) tissue vascularization, c) cell/vessel proximity, b) density of tumor matrix, and d) expression of stromal cell markers. In some embodiments, the target tissue in the individual has any one or more of the following characteristics: 1) high level of albumin uptake; 2) high level of caveolin-1 expression; 3) high level of gp60 expression; and 4) high level of SPARC expression. In some embodiments according to any of the methods described in this paragraph, taxane is paclitaxel or docetaxel. In some embodiments according to any of the methods described in this paragraph, the nanoparticles in the taxane nanoparticle composition have an average particle size of less than about 200 nm. In some embodiments according to any of the methods described in this paragraph, the taxane nanoparticle composition comprises a taxane coated with albumin. In some embodiments according to any of the methods described in this paragraph, the therapeutic agent is selected from the group consisting of: an antimetabolite, a platinum-based agent, and a prednisone.

In some embodiments, there is provided a method of treating a disease in an individual, comprising administering to the individual: (a) an effective amount of a composition comprising nanoparticles comprising albumin and a taxane, and (b) an effective amount of a therapeutic agent, wherein drug uptake capability is used as a basis for selecting the individual to receive treatment. In some embodiments, the method further comprises determining the drug uptake capability of the target tissue in the individual prior to the administration of the taxane nanoparticle composition. In some embodiments, the drug uptake capability is determined based on one or more characteristics selected from the group consisting of: (a) high level of albumin uptake; (b) high level of caveolin-1 expression; (c) high level of gp-60 expression; and (d) high level of SPARC expression. In some embodiments, the disease is cancer. In some embodiments, the cancer is a pancreatic cancer, lung cancer, melanoma, or prostate cancer. In some embodiments, the cancer is selected from the group consisting of: squamous cell carcinomas, mesothelioma, desmoplastic fibroma, desmoplastic round cell tumor, colorectal carcinoma and tumors of gastrointestinal tract. In some embodiments according to any one of the methods described in this paragraph, the taxane is paclitaxel or docetaxel. In some embodiments according to any of the methods described in this paragraph, the nanoparticles in the taxane nanoparticle composition have an average particle size of less than about 200 nm. In some embodiments according to any of the methods described in this paragraph, the taxane nanoparticle composition comprises a taxane coated with albumin. In some embodiments according to any of the methods described in this paragraph, the therapeutic agent is selected from the group consisting of: an antimetabolite, a platinum-based agent, and a prednisone.

In some embodiments, there is provided a method of assessing responsiveness of an individual to a treatment of a diseases comprising administration of (a) an effective amount of a composition comprising nanoparticles comprising albumin and a taxane and (b) an effective amount of a therapeutic agent, the method comprising determining drug uptake capability of the target tissue in the individual, wherein a drug uptake capability is indicative that the individual is responsive to the treatment. In some embodiments, the method further comprises administering the effective amount of a composition comprising nanoparticles comprising albumin and a taxane and a therapeutic agent to the individual.

In some embodiments, there is provided a method of treating prostate cancer in an individual, comprising administering to the individual a) an effective amount of a composition comprising nanoparticles comprising docetaxel and an albumin; and b) an effective amount of a steroid (such as prednisone).

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1. Clinical Studies for the Treatment of Pancreatic Cancer

This disease specific phase 1/2 study was designed to evaluate the safety and efficacy of gemcitabine plus Nab-paclitaxel (Nab-P) and the correlation of outcomes with tumor SPARC and serum CA19-9 levels.

Patient Eligibility: Patients 18 years or older with histologically confirmed metastatic adenocarcinoma of the pancreas were recruited. These patients had no islet cell neoplasms, locally invasive disease, or prior chemotherapy for metastatic disease.

Study Design and Treatment: The study was an open-label phase 1/2 study. 100, 125 or 150 mg/m2 Nab-paclitaxel+gemcitabine (1000 mg/m2) was administered weekly for 3 weeks (days 1, 8, 15) followed by a week of rest.

Safety Endpoints: Primary safety endpoint is maximum tolerated dose (MTD) and dose-limiting toxicity (DLT). Secondary end point is incidence of treatment-related adverse events (AEs) and serious AEs.

Efficacy Endpoints: Efficacy endpoint is confirmed response rate (RR; complete or partial responses [CR, PR]), stable disease (SD) at ≥16 weeks, disease progression (PD), progression-free survival (PFS), and overall survival (OS).

Assessment: Investigator response was determined by CT using RECIST criteria. Independent radiological review assessed CT by RECIST and PET using the EORTC criteria.

Biomarker Assessment: Different epitopes of SPARC were investigated with 2 antibodies (M and P) in both tumor cells and stromal fibroblasts. Serum CA19-9 levels were monitored at every cycle Statistical Analyses: The Cox proportional hazard model was used for PFS and OS. Correlation between CA19-9 levels and RR was examined by Fisher's exact test; max % change between CA19-9 levels and PFS/OS was analyzed by log-rank test. SPARC relation to outcomes like PFS were assessed by a log rank test.

Results: 67 patients received treatment. The confirmed overall response rate (ORR) by RECIST criteria using CT scans for all patients was 31/67 (46%) with 3/67 (4%) achieving a complete response. The ORR for the 100 mg/m2 cohort was 8/20 (40%) and the ORR for the 125 mg/m2 cohort was 22/44 (50%). The disease control rate (DCR, which includes ORR+stable disease for >=16 weeks) for all patients was 43/67 (64%). The DCR for the 100 mg/m2 cohort was 12/20 (60%) and the DCR for the 125 mg/m2 cohort was 30/44 (68%). Evaluation by PET scans in 45 patients resulted in a complete response in 6/45 (13%), partial response of 20/45 (44%) and a DCR or 27/45 (60%)

The median progression free survival (PFS) in 67 patients was 7.1 months. In the 100 mg/m2 cohort (20 patients) the PFS was 5.5 months and in the 125 mg/m2 cohort (44 patients) the PFS was 8 months.

The median overall survival (OS) in 67 patients was 10.3 months. In the 100 mg/m2 cohort (20 patients) the OS was 9.3 months and in the 125 mg/m2 cohort (44 patients) the OS was 12.2 months.

The most common grade 3 and 4 adverse event that occurred in >20% of patients was neutropenia. Nine (18%) patients and 4 (8%) patients had a grade 3/4 event, respectively. Neuropathy was also observed.

Nab-Paclitaxel plus gemcitabine was generally well tolerated in advanced pancreatic cancer patients. The MTD for this disease specific phase 1/2 trial was 125 mg/m2 nab-paclitaxel plus 1000 mg/m2 gemcitabine, weekly for 3 weeks followed by a week of rest.

The results suggested that the combination of Nab-paclitaxel and gemcitabine was very active in pancreatic cancer. A rapid decrease in serum CA19-9 levels ≥50% was observed in majority of the patients, mostly occurred during the first cycle, and correlated strongly with RR, PFS, and OS. Analysis of SPARC as a biomarker suggested that SPARC could be used to determine high risk and low risk patients with respect to overall survival. Together, our results indicate that Nab-paclitaxel plus gemcitabine is a very promising combination for treatment of patients with advanced pancreatic cancer.

Example 2. Studies on the Mechanism of Action of Gemcitabine and Abraxane®

Eleven Patient-derived low passage pancreatic tumor xenografts were implanted (s.c) in nude mice. Mice with tumor size of ~200 mm3 were randomized to four treatment groups (7-10 tumors/group) and treated with 1) Vehicle; 2) Abraxane® (ABI) 30 mg/kg once daily i.v for five consecutive days; 3) Gemcitabine (GEM) 100 mg/kg twice a week for 4 weeks i.p and 4) GEM+ABI in the above mentioned dose and frequency for 4 weeks. Tumor size was measured twice per week using a digital caliper. Number of tumors that regressed more than 50% of its initial size in each tumor xenografts were noted. Extent of stromal desmoplasia and endothelial cell content in control and treated xenografts were determined by Masson's Trichrome staining, IHC and qRTPCR.

In Vivo Efficacy:

Combination of GEM plus ABI resulted in enhanced antitumor activity compared to either single agents. 7 of 11 cases produced >50% regression of tumor size with combination therapy, while only 2 of 11 cases regressed with GEM treatment. Combination of GEM plus ABI produced remarkable tumor regression response in pancreatic cancer xenografts. Aggregate analysis of overall tumor regressions in 11 cases demonstrated superior tumor regression response with combination therapy. There was a 3.5 fold increase in tumor regression rate in mice treated with combination therapy compared to GEM alone.

Combination therapy with GEM and ABI facilitated the uptake of GEM in tumor. Mice harboring Panc265 xenograft were treated with 1) ABI 30 mg/kg i.v once a day for five consecutive days, 2) GEM 100 mg/kg on day one and five, or 3) Combination of GEM plus ABI in the above dose and frequency. Animals were sacrificed 1 hour after the GEM dose and tumors were harvested. GEM and paclitaxel concentrations in extracted tumor samples were measured by HPLC. Intratumoral concentration of gemcitabine increased by 3.7 fold in mice treated with GEM plus ABI versus those receiving GEM alone. There was a slight increase in paclitaxel concentration in GEM plus ABI versus those receiving ABI alone.

Combination therapy reduced stroma and increased tumor vascularization and cell-vessel proximity: Tumor vascular capacity was enhanced by combination treatment. CD31 IHC in Panc265 demonstrated narrow caliber blood vessels within the tumor milieu in all arms, except those tumors receiving combination of GEM+ABI, in which multiple prominently dilated vessels were easily observed.

qRT-PCR for mNestin transcripts, demonstrated a nearly 3-fold relative increase in mNestin levels in the combination therapy arm compared to control xenografts, while both single-agent arms exhibited low relative mNestin expression.

As determined by IHC, Combination therapy depleted the desmoplastic stroma of pancreatic tumors. Expression of tumor stroma in Panc265 and Panc163 by Mason's Trichome and Collagen Type 1 (Col1) showed that ABI and GEM plus ABI depleted the desmoplastic stroma as evidenced by the densely packed ductal tumor cells.

In conclusion, the combination of gemcitabine plus Nab®-paclitaxel produced remarkable tumor regression response in pancreatic cancer, effectively eliminated the pancreatic cancer stroma, enhanced the tumoral vascular density and facilitated the tumoral delivery of gemcitabine.

Example 3. Treatment of Lung Cancer

This example provides results from a phase 3 trial which studied the efficacy of Abraxane® (Nab-paclitaxel or nab-P) vs Taxol® (P) in combination with carboplatin (nab-PC v. PC) in advanced non-small cell lung cancer (NSCLC) of all histologic types.

Methods: First-line Stage IIIB or IV NSCLC patients (ECOG 0/1) were randomized to C AUC6 q3w and either nab-P 100 mg/m2 weekly without premedication (n=521) or P 200 mg/m2 once every three weeks with premedication (n=531). Primary endpoint: ORR by independent radiologic review (IRR).

Results: Baseline and histologic characteristics were well balanced. Dose intensity of paclitaxel was higher in nab-PC vs PC (82 vs 65 mg/m2/wk). nab-PC was superior to PC both by IRR (33% vs 25%, P=0.005), a 31% improvement (1.313 response ratio (RR), 95% CI: 1.082, 1.593), and by investigator review (37% vs 30%, P=0.008), a 26% improvement (1.259 RR, CI: 1.060, 1.496). Histologic analysis showed significantly improved ORR for nab-PC vs PC in squamous cell carcinoma (SQC) patients (41% vs 24%, P<0.001, IRR), a 67% improvement (1.669 RR, CI: 1.262, 2.208). nab-PC was as effective as PC in non-SQC patients (ORR 26% vs 25%). nab-PC was well tolerated, with significantly improved safety profile vs PC despite higher paclitaxel dose delivered (1338 vs 1100 mg/m2).

| Statistically significant events | nab-PC n = 514 | PC n = 524 | P-value |
|---|---|---|---|
| G ≥3 Nonhematologic, n (%) | | | |
| Neuropathy | 15 (3) | 56 (11) | <0.001 |
| Myalgia | 1 (<1) | 10 (2) | 0.011 |
| Arthralgia | 0 | 8 (2) | 0.008 |
| G 4 Hematologic, n (%) | | | |
| Neutropenia | 49 (11) | 98 (22) | <0.001 |
| Thrombocytopenia | 23 (5) | 5 (1) | 0.001 |
| Anemia | 21 (5) | 4 (1) | 0.001 |

Conclusions: nab-PC significantly improved ORR and safety profile vs PC as first-line therapy for advanced NSCLC. nab-PC was especially active in the SQC subset, which may in part be attributed to the aberrant CAV1 overexpression in squamous carcinoma cells (Yoo 2003) and the high intratumoral accumulation of nab-P via the gp60-CAV1 pathway.

Example 4. Treatment of Prostate Cancer

PSA (prostate specific antigen) response rate was measured in patients in 42 patients treated with a nanoparticle composition comprising albumin and docetaxel, namely, nab-docetaxel (at a dose of 75 mg/m2 q3wk) or a combination of nab-docetaxel and prednisone. In 13 patients treated with nab-docetaxel alone, a confirmed PSA response occurred in 3/13 (23%). In 29 patients treated with nab-docetaxel plus prednisone, a confirmed PSA response occurred in 13/29 (45%), almost double that seen with nab-docetaxel alone. Thus nab based delivery of docetaxel allows for enhanced effect of prednisone on prostate cancer tumors.

Example 4a. A Phase I/II Trial of Nab-Docetaxel in Patients with Hormone-Refractory Prostate Cancer The clinical study determined the maximum tolerated dose (MTD) and dose-limiting toxicities (DLTs) of Nab-docetaxel given every 3 weeks; characterized the toxicities of Nab-docetaxel; and determined the pharmacokinetic parameters for Nab-docetaxel when given on an every-3-week schedule. The study also evaluated the efficacy of Nab-docetaxel in this patient population.

Treatment Design

This Phase I study determined the MTD and DLT of Nab-docetaxel administered every 3 weeks. The starting dose of Nab-docetaxel was chosen based upon nonclinical data and the experience with solvent-based docetaxel.

Dosing escalation schedule (Nab-docetaxel administered on Day 1 of an every-3-week cycle): the dosages included were 30, 45, 60, 75, 100, 125, 150, 175, and 200 mg/m$^2$.

Three patients were enrolled at each dose level, starting at dose level 1. If no DLT was observed, 3 patients were enrolled at the next dose level. If 1 DLT was observed, the dose level was expanded to up to 6 patients. If 2 DLTs were observed at a given dose level, the MTD had been exceeded. The dose level below was expanded to a total of 6 patients, and if <1 out of 6 patients experience a DLT at this dose level, this was defined as the MTD. All patients at a given dose level completed one cycle of therapy before patients were enrolled at the next dose level. In the Phase II portion of the study, up to an additional 35 patients were enrolled at the MTD, for a maximum of 41 patients at that dose level (including 6 patients from the Phase I portion of the study). The maximum total number of patients treated in this study was 77 patients.

The Phase II MTD had established at 75 mg/m².

Patients continued on treatment until they experience progressive disease or unacceptable toxicity, withdraw consent, or their physician feels it was no longer in their best interest to continue on treatment. Each cohort received 1 cycle of treatment prior to dose escalation.

A DLT was defined in this study as any Grade 3 or 4 treatment-related non-hematological toxicity using the National Cancer Institute Common Terminology Criteria for Adverse Events (NCI CTCAE) (excluding nausea and vomiting); Grade 3 or 4 nausea or vomiting that occurs despite treatment; Grade 4 thrombocytopenia or anemia of any duration and Grade 4 uncomplicated neutropenia (i.e. without fever or infection) lasting >7 days. Neutropenia associated with fever or infection was considered to be a DLT, regardless of duration, or any Grade 3 hematologic toxicity requiring treatment delay beyond 3 weeks. DLTs were determined in Cycle 1 for the purposes of dose escalation and determining MTD.

The study consisted of the following phases (See Time and Events Schedule):

Baseline evaluations (imaging scans were performed within 28 days of the initiation of study drug dosing).

Treatment: Therapy continued in the absence of disease progression (based on PSA evaluation, tumor response, and radionuclide bone scans) and unacceptable toxicity.

PSA Evaluations: Patients had PSA evaluations done on Day 1 of each cycle. Caveolin-1 levels was measured on Day 1 of each cycle.

Tumor Response Assessments: Patients were evaluated for complete response (CR), partial response (PR), stable disease (SD), or progressive disease (PD) every 12 weeks or at the time of PSA progression or the development of new symptoms, until disease progression. Tumor response was evaluated using RECIST Criteria.

Pharmacokinetic Sampling—Cycle 1 of Phase I only. Parameters determined included volume of distribution, terminal half-life, $C_{max}$, $t_{max}$, $AUC_{inf}$ and plasma clearance.

End-of-Study (EOS) Evaluation: At the time patients were removed from study, laboratory and clinical evaluations to assess AEs were performed. Radiologic studies for antitumor response were repeated if they have not been done within the previous 28 days.

Adverse Event Collection and Follow-up—Any AE whose onset occurred between the first administration of study drug to 30 days after the last dose of study drug, whichever was later, were collected.

Disease Progression Follow-up: Patients who have not had progressive disease by the EOS evaluation continued to have PSA evaluations taken every 3 weeks and tumor response assessments conducted every 12 weeks until progressive disease (based on PSA evaluation or tumor response) was documented.

Table 1 Provided a Summary.

TABLE 1

| | | Time and Events Schedule | | | | | | |
|---|---|---|---|---|---|---|---|---|
| | | Each Cycle | | | Every 12 | | AE | PFS |
| Assessment | Baseline | Day 1 | Day 8 | Day 15 | weeks | EOS[A] | Resolution[B] | Follow-Up |
| Informed Consent | X | — | — | — | — | — | — | — |
| Medical History | X[N] | — | — | — | — | — | — | — |
| CT or MRI Scan of Chest/Pelvis/Abdomen[C] & any other studies required for tumor imaging | X | — | — | — | X[C] | X[D] | — | X |
| Chest X-Ray | X | — | — | — | X | — | — | — |
| Bone Scan | X | — | — | — | X | X[D] | — | — |
| CT Scan or MRI of Head (if clinically indicated)[E] | X | — | — | — | — | — | — | — |
| PSA and Caveolin-1 | X[N] | X[F] | — | — | — | X | — | X[G] |
| BSA Calculation and Height[H] | X[N] | — | — | — | — | — | — | — |
| Weight/Zubrod Performance Status | X[N] | X[F] | — | — | — | X | X | — |
| Physical Examination | X[N] | X[F] | — | — | — | X | X | — |
| Concomitant Medication Evaluation | X[N] | X | — | — | — | X | X | — |
| Concomitant Procedures Evaluation | — | X | — | — | — | X | X | — |
| Peripheral Neuropathy Assessment (physician and patient) | X[N] | X[F] | — | — | — | X | X | — |
| Vital Signs (Temperature, Pulse Rate, Respiratory Rate and Blood Pressure) | X[N] | X[I] | — | — | — | X | X | — |
| Adverse Event Evaluation[J] | — | X | — | — | — | X | X | — |
| CBC, Differential, Platelet Count[K] | X[N] | X[F] | X | X | — | X | X | — |
| Clinical Chemistry Panel | X[N] | X[F] | — | — | — | X | X | — |

TABLE 1-continued

Time and Events Schedule

| Assessment | Baseline | Each Cycle | | | Every 12 weeks | EOS[A] | AE Resolution[B] | PFS Follow-Up |
|---|---|---|---|---|---|---|---|---|
| | | Day 1 | Day 8 | Day 15 | | | | |
| Study Drug Administration[L] | — | X | — | — | — | — | — | — |

[A]EOS = End-of-Study. When patient comes off study the indicated tests were done. Repeat studies for tumor response only if not done within the previous 28 days.
[B]Follow-up for AEs and SAEs continued through 30 days after the patient discontinued the study drug. Any AEs/SAEs that begin during this time were followed until stable and no longer improving or until they have resolved. If there are no AEs or SAEs ongoing at the EOS visit, follow up may be by telephone to the patient weekly until 30 days from last dose of treatment.
[C]CT or MRI scan of the abdomen, and pelvis were performed at Baseline and every 12 weeks or at the time of PSA progression or the development of new symptoms, until disease progression. Whichever method was chosen at baseline to follow tumors remained consistent throughout study duration.
[D]Restaging studies were also to be done at the EOS visit if not done in the preceding 28 days, unless there was otherwise clear clinical evidence of progression.
[E]A CT scan of head could be performed if symptomology of brain metastasis existed (only if clinically indicated).
[F]If Baseline labs, physical exam, weight, Zubrod, and peripheral neuropathy assessment (physician and patient), PSA and Caveolin-1 had been completed within 72 hours prior to treatment, these assessments did not need to be repeated on Cycle 1, Day 1.
[G]PSA evaluations were collected every 3 week until disease progression.
[H]BSA calculated at Baseline and recalculated only if body weight changes by more than 10%.
[I]Pre and post Nab-docetaxel infusion.
[J]Completed prior to the first dose of each cycle.
[K]Study drug must not be administered at the start of a cycle until the ANC has returned to ≥1.5 × 10$^9$/l, and platelets have returned to ≥100 × 10$^9$/l, or any other toxicity resolves to Grade 1.
[L]Nab-docetaxel on Day 1 of each cycle, plus prednisone 5 mg orally twice daily (morning and evening).
[M]Prior to Cycle 2 only.
[N]Required within 10 days prior to the first dose of study drug.

Inclusion/Exclusion Criteria

A patient was eligible for inclusion in this study only if all of the following criteria were met: 1) patients must have had histologically or cytologically confirmed adenocarcinoma of the prostate that is clinically refractory to hormone therapy, 2) Zubrod Performance Status 0-1, 3) at the time of enrollment, patients must have had evidence of progressive metastatic disease, either: a) measurable disease with any level of serum PSA or b) non-measurable disease with PSA≥5 ng/ml. (Patients with PSA≥5 ng/ml only and no other radiographic evidence of metastatic prostate cancer were not eligible), 4) patients must have demonstrated evidence of progressive disease since the most recent change in therapy, 5) serum testosterone ≤50 ng/ml, determined within two weeks prior to starting treatment, 6) maintained castrate status (Patients who have not undergone surgical orchiectomy continued on medical therapies [e.g. gonadotropin releasing hormone analogs (GnRH analogs)] to maintain castrate levels of serum testosterone. Patients who were receiving an anti-androgen as part of their first-line hormonal therapy showed progression of disease off of the anti-androgen prior to enrollment (6 weeks withdrawal for Casodex; 4 weeks for flutamide)), 7) Megestrol acetate (Megace®) treatment could continue if patient had been on stable doses of the drug. If patients discontinued Megace, they showed progression of disease off of this medication, 8) age ≥18 years of age, 9) four weeks since major surgery, 10) the following restrictions on prior therapy for metastatic disease apply: a) no prior chemotherapy regimen for metastatic disease, b) no more than one prior course of palliative radiotherapy, c) up to one prior treatment with a non-chemotherapeutic agent (e.g., kinase inhibitors, immunotherapeutic agents, etc) was permitted as treatment for metastatic disease, d) no prior radioisotope therapy with Strontium-89, Samarium or similar agents, and e) one prior neo-adjuvant or adjuvant chemotherapy regimen was permitted if given over 3 years ago, 11) no limitation on prior hormonal therapy, 12) patients were off all therapy for at least 4 weeks prior to study drug administration, 13) life expectancy was ≥3 months, 14) patients signed an informed consent document stating that they understood the investigational nature of the proposed treatment, 15) required Initial Laboratory Data: a) WBC≥3,000 μl, b) ANC≥1,500 μl, c) platelet count≥100,000 μl, d) creatinine≤1.5×upper limits of normal, e) total Bilirubin-≤upper limit of normal (exceptions will be made for patients with Gilbert's Disease), f) SGOT (AST)≤1.5×upper limits of normal, and f) SGPT (ALT)≤1.5×upper limits of normal, 16) taxanes are considered to be teratogenic (For this reason men whose sexual partners were of child-bearing age agreed to use adequate contraception (hormonal or barrier method of birth control) for the duration of study participation.), and 17) if obese (weight >20% of ideal body weight) patient must be treated with doses calculated using adjusted body surface area (BSA) (based on calculated adjusted weight) or actual BSA.

Progressive disease in the inclusion criteria was defined as any one of the following (measurable disease, bone scan, or PSA progression): 1) measurable Disease Progression (Objective evidence of increase >20% in the sum of the longest diameters (LD) of target lesions from the time of maximal regression or the appearance of one or more new lesions.), 2) bone scan progression (Appearance of either of the following constituted progression: (a) two or more new lesions on bone scan attributable to prostate cancer; or (b) one new lesion on bone scan attributable to prostate cancer in conjunction with a rising PSA.), or 3) PSA Progression (In the presence of radiographic evidence of disease, an elevated PSA (≥5 ng/mL) which has risen serially from baseline on two occasions each at least one week apart. If the confirmatory PSA value was less than screening PSA value, then an additional test for rising PSA was required to document progression.).

A patient was ineligible for inclusion in this study if any of the following criteria applied: 1) patients could not be receiving any other investigational agents, 2) patients could continue on a daily Multi-Vitamin, low dose (≤400 IU qd) Vitamin D, Calcitrol (≤0.5 mcg qd), and calcium supplements, but all other herbal, alternative and food supplements (i.e. PC-Spes, Saw Palmetto, St John Wort, etc.) must be discontinued before start of treatment, 3) patients on stable doses of bisphosphonates, who develop subsequent tumor progression, could continue on this medication. (However, patients were not allowed to initiate bisphosphonate therapy immediately prior to or during the study because starting bisphosphonates could potentially confound the interpretation of adverse events.), 4) patients with known brain metastases were excluded from this clinical trial because they often developed progressive neurologic dysfunction that could confound the evaluation of neurologic and other adverse events, 5) patients with history of allergic reactions attributed to solvent-based docetaxel (Taxotere) were not eligible for the study, 6) patients with significant cardiovascular disease including congestive heart failure (New York Heart Association Class III or IV), active angina pectoris or recent myocardial infarction (within the last 6 months) were excluded, 7) patients with a "currently active" second malignancy other than non-melanoma skin cancers were not to be registered. (Patients were not considered to have a "currently active" malignancy if they completed therapy and were now considered (by their physician) to be at low risk for relapse.), 8) uncontrolled intercurrent illness including, but not limited to, ongoing or active infection, symptomatic congestive heart failure, unstable angina pectoris, cardiac arrhythmia, or psychiatric illness/social situations that limited compliance with study requirements, or 9) because patients with immune deficiency were at increased risk of lethal infections when treated with marrow-suppressive therapy, HIV-positive patients receiving combination anti-retroviral therapy were excluded from the study because of possible pharmacokinetic interactions with docetaxel.

Dosages and Administration

All patients were treated with Nab-docetaxel IV (60 minutes infusion ±5 minutes) administered every 3 weeks plus prednisone 5 mg orally administered twice daily (morning and evening). Cohorts of 3 patients each received 60, 75, 100, 125, 150, 175 or 200 mg/m² Nab-docetaxel as a 1-hour infusion on Day 1 of each cycle of Phase I. The dose of Nab-docetaxel was escalated depending on the toxicity profile observed in the previous 3-patient cohort.

Efficacy Endpoints

The primary efficacy endpoint was percentage of patients who achieved a confirmed prostate-specific antigen (PSA) response where PSA response was defined as either PSA normalization or a PSA decline. PSA normalization was defined as PSA<1.0 ng/ml for patients whose primary disease was treated with radiotherapy only and PSA undetectable for patients who have had a prostatectomy, for 2 successive evaluations at least 4 weeks apart. PSA decline was defined as a decrease in PSA value by ≥50% from pre-treatment for 2 successive evaluations at least 4 weeks apart. The pre-treatment PSA value was measured within 2 weeks before starting therapy.

Secondary efficacy endpoints included: a) percentage of patients with measurable disease who achieve an objective confirmed complete or partial overall tumor response using Response Evaluation Criteria in Solid Tumors (RECIST) Criteria, b) time to PSA Progression, c) progression-free survival based on tumor response using RECIST Criteria.

PSA Evaluation

In previous work others have shown the prognostic significance of post-therapy decline in PSA. Tahir S A et al. *Clin Cancer Res.* 2003; 9:3653-9. Based on this work a NCI consensus group proposed the following guidelines for the use of post-therapy PSA changes in androgen-independent disease. Kelly W K et al. *J Clin Oncol.* 1993; 11:607-615.

PSA normalization defined as PSA<1.0 ng/ml for patients whose primary disease was treated with radiotherapy only and PSA undetectable for patients who have had a prostatectomy, for 2 successive evaluations at least 4 weeks apart.

PSA decline defined as a decrease in PSA value by ≥50% from pre-treatment for 2 successive evaluations at least 4 weeks apart. The pre-treatment PSA value was measured within 2 weeks before starting therapy.

PSA progression defined as the date of PSA increase meeting the criteria of progression (i.e., not the date of confirmation).

In patients who have achieved a ≥50% decline in PSA, progression was defined by: 1) an increase in PSA by 50% above the nadir and 2) an increase in PSA by a minimum of 5 ng/mL, or an increase in PSA to the pretreatment PSA value, and 3) confirmation by a second consecutive rising PSA at least 2 weeks apart.

In patients whose PSA has not decreased by ≥50%, progression was defined by: 1) an increase in PSA by 25% above either the pre-treatment level, or the nadir PSA level (whichever is lowest) and 2) an increase in PSA by a minimum of 5 ng/mL and 3) confirmation by a second consecutive rising PSA at least 2 weeks apart.

Note: If confirmation was not observed because the patient began a new anti-cancer therapy following the initial observed PSA progression, then the patient was considered to have confirmed PSA progression.

Response

At baseline, tumor lesions were categorized as follows: measurable (lesions that could be accurately measured in at least 1 dimension [longest diameter to be recorded] as ≥20 mm with conventional techniques or as ≥10 mm with spiral CT scan) or nonmeasurable (all other lesions, including small lesions [longest diameter <20 mm with conventional techniques or <10 mm with spiral CT scan] and truly nonmeasurable lesions).

All measurable lesions up to a maximum of 5 lesions per organ and 10 lesions in total, representative of all involved organs, were identified as target lesions and recorded and measured at baseline. Target lesions were selected on the basis of their size (those with the longest diameter) and their suitability for accurate repeated measurements (either by imaging techniques or clinically). A sum of the longest diameter for all target lesions were calculated and reported as the baseline sum longest diameter. The baseline sum longest diameter was used as the reference by which to characterize the objective tumor response.

All other lesions (or sites of disease) were identified as nontarget lesions.

Antitumor activity will be evaluated in patients with measurable and/or nonmeasurable lesions according to RECIST guidelines.

The following definitions were used to evaluate response based on target lesions at each time point after baseline: Complete Response (CR): The disappearance of all known disease and no new sites or disease related symptoms confirmed at least 4 weeks after initial documentation. All sites were assessed, including non-measurable sites, such as effusions, or markers. Partial Response (PR): At least a 30% decrease in the sum of the longest diameters of target lesions, taking as a reference the baseline sum of the longest diameters confirmed at least 4 weeks after initial documentation. PR was also recorded when all measurable disease has completely disappeared, but a non-measurable component (i.e., ascites) was still present but not progressing. Stable Disease (SD): Neither sufficient shrinkage to qualify for partial response nor sufficient increase to qualify for progressive disease. Progressive Disease (PD): At least a 20% increase in the sum of the longest diameters of target lesions, taking as reference the smallest sum of the longest diameters recorded since the treatment started; or the appearance of one or more new lesions; or the unequivocal progression of a non-target lesion.

Response assessments of Non Target lesions were defined as follows: Complete Response (CR): Disappearance of all non-target lesions and the normalization of tumor marker level confirmed at least 4 weeks after initial documentation. Stable Disease (SD): Persistence of one or more non-target lesion(s) and/or the maintenance of tumor marker level above the normal limits Progressive Disease (PD): The appearance of one or more non-target lesions and/or unequivocal progression of existing non-target lesions. Unable to Evaluate (UE): No non-target lesion(s) documented at Baseline, or since treatment started.

Time to PSA Progression

Time to PSA progression was summarized using Kaplan-Meier methods. Time to PSA progression was defined as the time from first dose of study drug to the start of PSA progression. Patients who did not have PSA progression at the end of follow-up were censored at the time of their last PSA evaluation.

Progression-Free Survival Based on Tumor Response

Progression-free survival was summarized using Kaplan-Meier methods. Progression-free survival was defined as the time from first dose of study drug to the start of disease progression or patient death (any cause) whichever occurs first. Patients who did not have disease progression or have not died were censored at the last known time that the patient was progression free.

Safety/Tolerability Endpoints

The primary safety endpoint was determining the MTD and DLTs of Nab-docetaxel in patients with HRPC. Other secondary safety/tolerability endpoints include the incidence of treatment emergent adverse events (AEs) and serious adverse events (SAES), laboratory abnormalities and nadir of myelosuppression during study drug dosing, and percentage of patients experiencing dose modifications, dose interruptions, and/or premature discontinuation for each study drug.

AEs occurring during the study were graded according to the NCI Common Terminology Criteria for Adverse Events v3.0 (CTCAE) (see http://ctep.cancer.gov/reporting/ctc.html), where applicable. AEs that were not included on the toxicity scale were designated as Grade 1=mild, Grade 2=moderate, Grade 3=severe, Grade 4=life-threatening, and Grade 5=death. Non-serious AEs that were determined not to be possibly, probably, or definitely related to study drug did not require further evaluation but were recorded. Study medications could be interrupted for an AE at the discretion of the investigator. Patients requiring toxicity management were assessed and evaluated at least weekly as indicated by the severity of the event.

According to the NCI CTCAE system of adverse event grading, laboratory values of Grade 3 or 4 were described as "severe" or "life-threatening." For example, a neutrophils count <500/mm$^3$ would meet laboratory criteria as Grade 4 ("life-threatening"). This description was not always synonymous with the assessment of the "serious" criteria of an AE as "life threatening". Definition of AE and SAE are provided herein.

In order for AEs to be considered serious by "life-threatening" criteria, it was medically judged as possessing "an immediate risk of death from the event as it occurred," not because of the theoretical potential for life-threatening consequences. In the case of a neutrophil count <500/mm$^3$, the AE would be captured as an AE of Grade 4 neutropenia, but it was not automatically considered a SAE unless the investigational physician determined this represented an immediately life-threatening event for the patient. Specifically, uncomplicated Grade 4 neutropenia was not reported as a SAE. Neutropenia associated with fever, infection, or hospitalization was reported as a SAE.

Patients in the treated population were followed for the development of AEs from study drug initiation through the end of study or 30 days after the end of treatment, whichever was longer. Only patients with clear documentation that no study drug was administered could be excluded from the treated population.

Pharmacokinetic Endpoints

The pharmacokinetic endpoints include the elimination rate constant, elimination half-life, the volume of distribution ($V_z$), the maximum plasma drug concentration ($C_{max}$), $T_{max}$, the area under the plasma concentration versus time curve ($AUC_{inf}$), and plasma clearance.

Laboratory Assessments

Hematology Parameters—

To investigate the maximal degree of myelosuppression, the CTCAE grade for WBC, ANC, platelet count, and hemoglobin concentration were summarized by the most severe grade for the first treatment cycle and by the most severe grade anytime during therapy. The incidence of patients with CTCAE hematology values of Grade 3 or 4 that occurred after the first dose of study drug was presented for each group. Data for patients with Grade 3 or 4 hematology values were listed.

Clinical Chemistry—

Liver and renal functions were summarized using the CTCAE for ALT, AST, total bilirubin, and creatinine. The number and percentage of patients who have each CTCAE grade were summarized by the most severe grade for the first cycle of therapy and by the most severe grade anytime during therapy for each treatment regimen; testing of treatment regimen differences was performed using the CMH test. The incidence of patients with CTCAE chemistry values of Grade 3 or 4 that occurred after the first dose of study drug was presented for each group. Data for patients with Grade 3 or 4 chemistry values were listed.

Evaluation of Molecular Biomarkers

Expression levels of Caveolin-1 (Cav1) were evaluated.

Results

PSA (prostate specific antigen) response rate was measured in patients in 42 patients treated with a nanoparticle composition comprising albumin and docetaxel, namely, Nab-docetaxel (at a dose of 75 mg/m2 q3wk) or a combination of Nab-docetaxel and prednisone. In 13 patients treated with nab-docetaxel alone, a confirmed PSA response occurred in 3/13 (23%). In 29 patients treated with nab-docetaxel plus prednisone, a confirmed PSA response occurred in 13/29 (45%), almost double that seen with nab-docetaxel alone. Thus Nab based delivery of docetaxel allows for enhanced effect of prednisone on prostate cancer tumors.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating a cancer that is highly fibrotic and/or has a dense stroma in an individual, comprising administering to the individual an effective amount of a composition comprising nanoparticles comprising paclitaxel and an albumin, wherein a high stromal caveolin-1 level is used as a basis for selecting the individual to receive treatment, wherein the high stromal caveolin-1 level is a level that is higher than the median level in a patient population having the cancer, wherein the cancer is at an advanced stage, wherein the cancer is a lung cancer, wherein the nanoparticles in the composition have an average diameter of no greater than about 200 nm, and wherein the nanoparticles in the paclitaxel nanoparticle composition comprise paclitaxel coated with albumin.

2. The method of claim 1, wherein the cancer is a squamous cell carcinoma.

3. The method of claim 1, wherein the method comprises assessing one or more of the following in the individual prior to administering the paclitaxel nanoparticle composition: (a) the amount of tissue stroma, (b) tissue vascularization, (c) cell/vessel proximity, (d) density of tumor matrix, and (e) expression of stromal cell markers.

4. The method of claim 1, wherein the nanoparticles in the paclitaxel nanoparticle composition have an average particle size of less than 200 nm.

5. A method of treating a cancer in an individual, comprising administering to the individual:
(a) an effective amount of a composition comprising nanoparticles comprising albumin and paclitaxel, and
(b) an effective amount of a therapeutic agent,
wherein a high stromal caveolin-1 level is used as a basis for selecting the individual to receive treatment,
wherein the high stromal caveolin-1 level is a level that is higher than the median level in a patient population having the cancer,
wherein the cancer is at an advanced stage,
wherein the cancer is lung cancer,
wherein the nanoparticles in the composition have an average diameter of no greater than about 200 nm, and
wherein the nanoparticles in the paclitaxel nanoparticle composition comprise paclitaxel coated with albumin.

6. The method of claim 5, comprising determining the stromal caveolin-1 level in the individual prior to the administration of the paclitaxel nanoparticle composition.

7. The method of claim 5, wherein the cancer is a squamous cell carcinoma.

8. The method of claim 5, wherein the nanoparticles in the paclitaxel nanoparticle composition have an average particle size of less than 200 nm.

9. The method of claim 5, wherein the therapeutic agent is selected from the group consisting of: an antimetabolite, a platinum-based agent, and prednisone.

10. The method of claim 5, wherein the individual is not responsive to the treatment of the composition comprising nanoparticles comprising paclitaxel and the albumin when administered alone.

11. The method of claim 5, wherein the individual is not responsive to the treatment of the therapeutic agent when administered alone.

12. The method of claim 10, wherein the individual is not responsive to the treatment of the therapeutic agent when administered alone.

* * * * *

UNITED STATES PATENT AND TRADEMARK OFFICE
CERTIFICATE OF CORRECTION

PATENT NO. : 10,660,965 B2
APPLICATION NO. : 13/073861
DATED : May 26, 2020
INVENTOR(S) : Desai et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 119 days.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*